(12) United States Patent
Iizuka et al.

(10) Patent No.: US 7,029,436 B2
(45) Date of Patent: Apr. 18, 2006

(54) OPTICAL PROBE FOR PRODUCING TOMOGRAM OF SPECIMEN BY THE USE OF LOW-COHERENCE LIGHT

(75) Inventors: Shuhei Iizuka, Hachioji (JP); Akihiro Horii, Hachioji (JP); Mamoru Kaneko, Hanno (JP); Kenji Hirooka, Hachioji (JP); Hitoshi Mizuno, Koganei (JP)

(73) Assignee: Olympus Corporation, (JP)

( * ) Notice: Subject to any disclaimer, the term of this patent is extended or adjusted under 35 U.S.C. 154(b) by 639 days.

(21) Appl. No.: 10/095,225

(22) Filed: Mar. 8, 2002

(65) Prior Publication Data

US 2003/0013952 A1    Jan. 16, 2003

(30) Foreign Application Priority Data

Mar. 12, 2001    (JP)    .............................. 2001-069106

(51) Int. Cl.
*A61B 1/00*    (2006.01)
(52) U.S. Cl. ........................ 600/160; 600/121; 600/153
(58) Field of Classification Search ........ 600/121–125, 600/160, 139, 153
See application file for complete search history.

(56) References Cited

U.S. PATENT DOCUMENTS

| 5,321,501 | A | | 6/1994 | Swanson et al. ............ 356/345 |
| 5,556,367 | A | * | 9/1996 | Yabe et al. ................. 600/124 |

FOREIGN PATENT DOCUMENTS

| JP | 6-511312 | 12/1994 |
| JP | 11-56786 | 3/1999 |
| WO | 97/32182 | 9/1997 |

* cited by examiner

*Primary Examiner*—Beverly M. Flanagan
(74) *Attorney, Agent, or Firm*—Ostrolenk, Faber, Gerb & Soffen, LLP

(57) ABSTRACT

On the side at hand of an optical probe, a whole rotation transfer connector rotates while being supported by a ball bearing and a slide bearing and, therefore, rotation is transferred to a flexible shaft. The relative position between the flexible shaft and an optical sheath is changed in accordance with the amount of screwing of a sheath stopping member on the side at hand into an outer cylinder by an external thread portion and an internal thread portion. When the optical sheath is moved furthermore, the flexible shaft is elongated due to elastic deformation because the length of the flexible shaft is regulated by the interval between a locking part of a locking member at the tip and a shaft stopping member. A tip housing is made to contact with the locking member while tension is applied to the flexible shaft by the rear end surface in the direction of the side at hand. During the use of optical probe, even when the optical probe is curved and the inner surface of the flexible shaft is contacted with the inner surface of the optical sheath, moving of the tip housing is canceled by the elongation amount of the flexible shaft elongated in advance and, therefore, the tip housing rotates at a constant position relative to the probe longitudinal direction on all occasions.

51 Claims, 35 Drawing Sheets

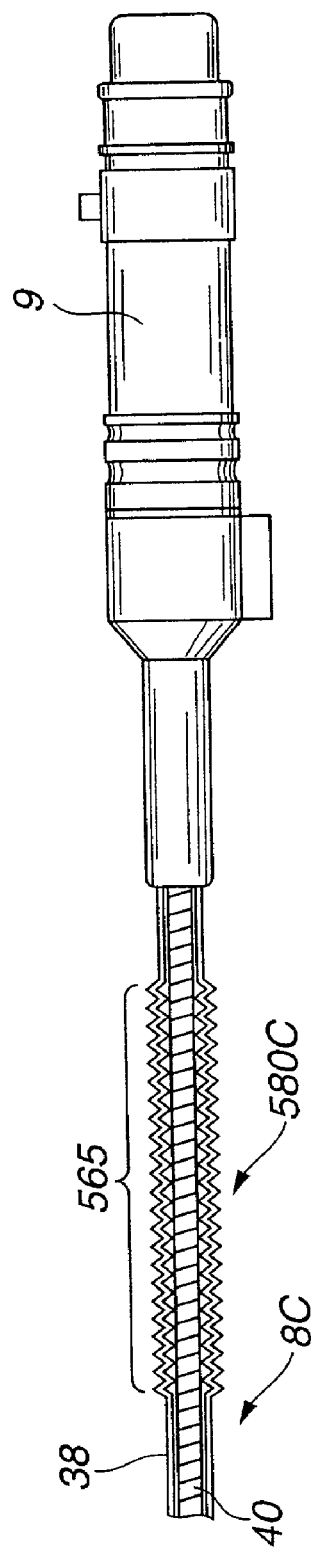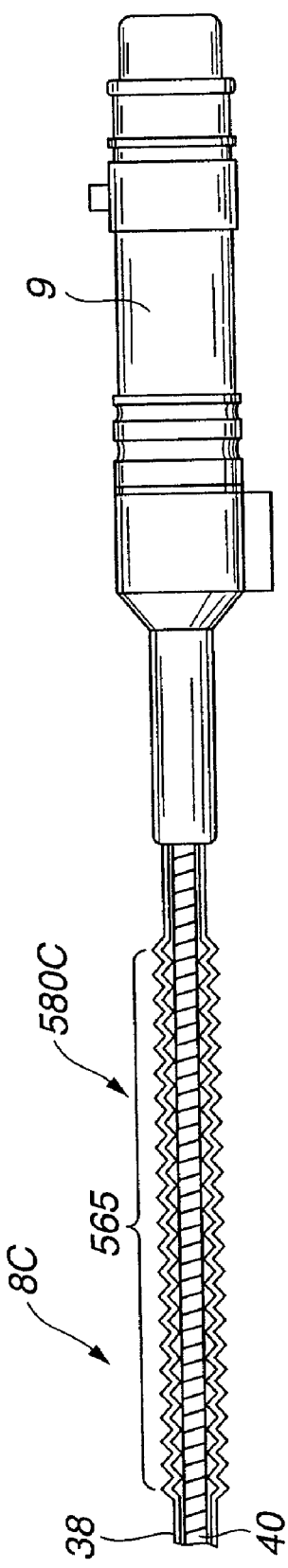
FIG.20A
FIG.20B

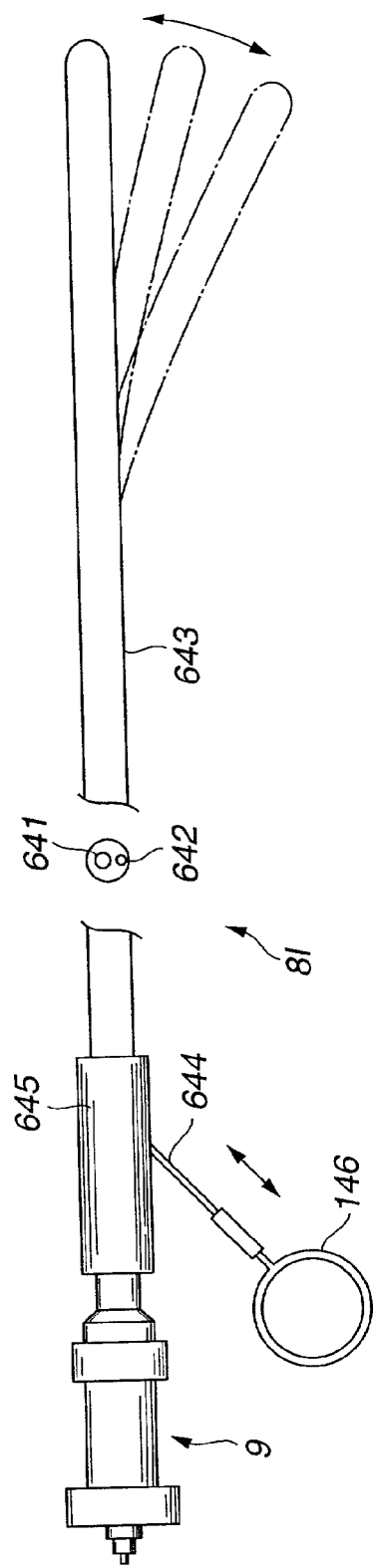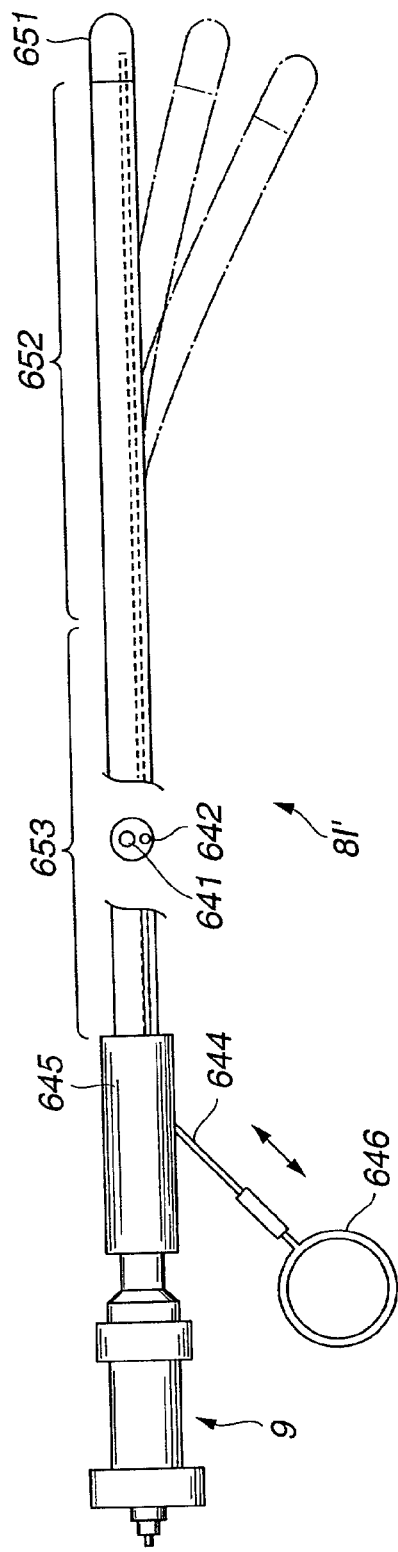

OPTICAL PROBE FOR PRODUCING TOMOGRAM OF SPECIMEN BY THE USE OF LOW-COHERENCE LIGHT

This application claims benefit of Japanese Application No. 2001-69106 filed in Japan on Mar. 12, 2001, Japanese Application No. Hei 11-264248 filed in Japan on Sep. 17, 1999, and Japanese Application No. Hei 11-259511 filed in Japan on Sep. 13, 1999, the contents of which are incorporated by this reference.

BACKGROUND OF THE INVENTION

1. Field of the Invention

The present invention relates to an optical probe for producing a tomogram of a specimen from the information of light scattered in the specimen by radiating the specimen with low-coherence light.

2. Related Art Statement

In recent years, in the case where living-body tissue is diagnosed, as a device which can gain optical information regarding the inside of the tissue, OCT (Optical•Coherence•Tomography) which produces a tomogram of a specimen by the use of low-coherence light has been disclosed in, for example, PCT Japanese Translation Patent Publication No. 6-511312.

However, regarding the conventional optical probe, there are disadvantages in that, for example, since when a tube-shaped sheath is curved, a flexible shaft is contacted with the inner surface of the tube-shaped sheath, the relative length between the tube-shaped sheath and the flexible shaft is changed, and consequently, when the tip clearance between the tip inner surface of the tube-shaped sheath and the tip surface of the tip unit is small, rotation performance is degraded due to butting of the sheath tip portion and the inside rotor and, therefore, a proper OCT image cannot be produced.

When this tip clearance (gap) is large, since the relative length between the tube-shaped sheath and the flexible shaft is changed as described above, the position of the light exit•entrance portion of the tip unit is changed. Consequently, there are problems in that, for example, it becomes difficult for an operator to ascertain the light exit position and, therefore, operating ease for the operator during observation is degraded.

Regarding the conventional optical probe, since the tip clearance which is the interval between the inner surface of the tip side seal portion and the tip portion of a member holding an optical element in the sheath lumen has been minimized, precision in sheath length has been required and, therefore, productivity has been degraded. The length of the sheath is changed depending on, for example, use with bending, change with time, and friction during insertion due to reuse.

There have been disadvantages in that, for example, when the tip clearance has been large, operating ease for the operator during observation has been degraded, and when the tip clearance has been small, rotation performance has been degraded due to butting of the sheath tip portion and the inside rotor and, therefore, it has not been possible to produce a proper OCT image.

Regarding the conventional optical probe, in the case where a probe is curved, for example, the probe is inserted through a channel for forceps of an endoscope and is inserted into a body cavity, a support portion of the optical element at the tip, etc., are rotated while being in contact with the inner side of a sheath and, therefore, the inner surface of the sheath may be damaged, or the sheath outer surface may be damaged due to friction between the channel for forceps inner surface and the sheath outer surface by insertion operation into the channel for forceps. Consequently, sometimes, optical characteristics of the part, where observation light has been made to exit or enter the optical element faced, have been degraded and, therefore, the optical performance of the sheath has been maintained by making the sheath exchangeable as disclosed in, for example, Japanese Patent Application No. Hei 10-266753.

However, since the lengths of the probe main bodies to be inserted into the sheath have varied depending on individual pieces, it has been necessary to produce while the lengths of the sheaths have been adjusted in accordance with probes on a piece basis, or to produce while the length tolerance of the probe main body is made to become closer. This has caused further reduction of productivity of the sheath.

OBJECTS AND SUMMARY OF THE INVENTION

It is an object of the present invention to provide an optical probe in which the tip clearance can be minimized and the light exit position can be kept at a proper position.

It is another object of the present invention to provide an optical probe in which the tip clearance can be adjusted•kept at a proper position even when the sheath length and the length of probe main body vary.

Furthermore, it is another object of the present invention to provide an optical probe in which the tip clearance can be minimized, the tip clearance can be adjusted•kept at a proper position, and a rotation axis of the light exit•entrance portion of the low-coherence light can be kept stably.

The configuration of an optical probe according to the present invention includes a sheath in which at least the tip side is transparent and flexible and the tip is blocked, a light exit•entrance portion provided in the lumen in the neighborhood of the aforementioned sheath tip, a housing for holding the aforementioned light exit•entrance portion, a flexible shaft which is connected to the rear end of the aforementioned housing and which transfers torque, and a base end portion, to which the rear end side of the aforementioned flexible shaft and the rear end side of the sheath are connected, wherein a relative distance adjustment mechanism capable of adjusting the relative distance between the aforementioned housing and the aforementioned sheath tip is provided at the aforementioned base end portion.

Other features and advantages of the present invention will become clear from the following description to a sufficient degree.

BRIEF DESCRIPTION OF THE DRAWINGS

FIG. 1 is a configurational diagram showing the whole configuration of an optical imaging device provided with an optical probe device, FIG. 2 is a diagram showing an endoscope through which the optical probe device shown in FIG. 1 is inserted, FIG. 3 is a configurational diagram showing the configuration of the tip of the optical probe device shown in FIG. 1, FIG. 4 is a configurational diagram showing the configuration of the base end of the optical probe device shown in FIG. 3, FIG. 5 is a sectional view showing the section indicated by line A—A in FIG. 4, FIG. 6 is a diagram for explaining connection of the optical probe device shown in FIG. 1 and a rotation drive device, FIG. 7 is a configurational diagram showing the configuration of a modified example of the tip of the optical probe device shown in FIG. 3, and FIG. 8 is a configurational diagram showing the configuration of a modified example of the base end of the optical probe device shown in FIG. 3.

FIG. 9 is a diagram showing the schematic configuration of an optical probe device and a rotation drive device, FIG. 10 is a diagram showing the whole of the optical probe device, FIG. 11 is a diagram showing the detailed configuration of a connector of an optical probe device, FIG. 12 is a diagram showing a sheath length adjustment mechanism, FIG. 13 is a configurational diagram showing the configuration of the key portion of the optical probe device shown in FIG. 9, and FIG. 14 is a diagram showing a modified example of the sheath length adjustment mechanism.

FIG. 15 is a diagram showing the configuration of a sheath length adjustment mechanism, FIG. 16 is a configurational diagram showing the configuration of the key portion of an optical probe, FIG. 17 is a configurational diagram showing the configuration of the key portion of a first modified example of the optical probe shown in FIG. 16, FIG. 18 is a configurational diagram showing the configuration of the key portion of a second modified example of the optical probe shown in FIG. 16, and FIG. 19 is a configurational diagram showing the configuration of the key portion of a third modified example of the optical probe shown in FIG. 16.

FIG. 20A to FIG. 21 relate to a fourth embodiment according to the present invention, FIG. 20A is a first diagram showing the configuration of a sheath length adjustment mechanism of an optical probe, FIG. 20B is a second diagram showing the configuration of a sheath length adjustment mechanism of the optical probe, and FIG. 21 is a configurational diagram showing the configuration of the key portion of an optical probe device.

FIG. 22 is a configurational diagram showing the configuration of the key portion of an optical probe, FIG. 23 is a first explanation diagram for explaining an action of the optical probe shown in FIG. 22, FIG. 24 is a second explanation diagram for explaining an action of the optical probe shown in FIG. 22, FIG. 25 is a configurational diagram showing the configuration of the key portion of a first modified example of the optical probe shown in FIG. 22, FIG. 26 is a configurational diagram showing the configuration of the key portion of a second modified example of the optical probe shown in FIG. 22, FIG. 27 is a configurational diagram showing the configuration of the key portion of a third modified example of the optical probe shown in FIG. 22, and FIG. 28 is a configurational diagram showing the configuration of the key portion of a fourth modified example of the optical probe shown in FIG. 22.

FIG. 29 is a configurational diagram showing the configuration of the key portion of an optical probe, and FIG. 30 is a diagram showing a modified example of the bearing shown in FIG. 29.

FIG. 31 is a configurational diagram showing the configuration of the key portion of an optical probe, FIG. 32 is an explanation diagram for explaining injection of a liquid for refractive index matching into an optical sheath shown in FIG. 31, FIG. 33 is a configurational diagram showing the configuration of a bubble trap shown in FIG. 31, FIG. 34 is a configurational diagram showing the configuration of the a first modified example of the bubble trap shown in FIG. 31, FIG. 35 is a configurational diagram showing the configuration of the a second modified example of the bubble trap shown in FIG. 31, FIG. 36 is a configurational diagram showing the configuration of a third modified example of the bubble trap shown in FIG. 31, FIG. 37 is a first explanation diagram for explaining an action of the optical probe shown in FIG. 31, FIG. 38 is a second explanation diagram for explaining an action of the optical probe shown in FIG. 31, FIG. 39 is a configurational diagram showing the configuration of the key portion of a modified example of the optical probe shown in FIG. 31, FIG. 40 is a first diagram for explaining a modified example of the injection of the liquid for refractive index matching into the optical sheath shown in FIG. 32, FIG. 41 is a second diagram for explaining the modified example of the injection of the liquid for refractive index matching into the optical sheath shown in FIG. 32, and FIG. 42 is a third diagram for explaining the modified example of the injection of the liquid for refractive index matching into the optical sheath shown in FIG. 32.

FIG. 43 is a configurational diagram showing the configuration of the key portion of an optical probe, FIG. 44 is an explanation diagram for explaining an action of the optical probe shown in FIG. 43, FIG. 45 is a configurational diagram showing the configuration of the key portion of a first modified example of the optical probe shown in FIG. 43, FIG. 46 is an explanation diagram for explaining an action of the optical probe shown in FIG. 45, and FIG. 47 is a configurational diagram showing the configuration of the key portion of a second modified example of the optical probe shown in FIG. 43.

FIG. 48 is a configurational diagram showing the configuration of the key portion of an optical probe, FIG. 49 is an explanation diagram for explaining a mesh ring shown in FIG. 48, and FIG. 50 is a configurational diagram showing the configuration of the key portion of a modified example of the optical probe shown in FIG. 48.

FIG. 51 is a diagram showing the configuration of the tip side of an optical probe device, and FIG. 52 is a diagram showing the configuration of the tip side of a modified example of the optical probe device.

FIG. 54A is a diagram showing the configuration of the tip side of an optical probe, and FIG. 54B is a diagram showing the configuration of the tip side of a modified example of the optical probe device.

FIG. 55 is a diagram showing the configuration of the tip side of an optical probe, FIG. 56 is a diagram showing an example of use, and FIG. 57 is a diagram showing the configuration of the tip side of a modified example of the optical probe.

FIG. 58 is a diagram showing the configuration of the tip side of an optical probe, FIG. 59 is a diagram showing an example of use, and FIG.

60 is a diagram showing the configuration of the tip side of a modified example of the optical probe.

FIG. 61 and FIG. 62 relate to a fifteenth embodiment according to the present invention, FIG. 61 is a diagram showing the configuration of an optical probe, and FIG. 62 is a diagram showing the configuration of a modified example of the optical probe.

Figure 63:
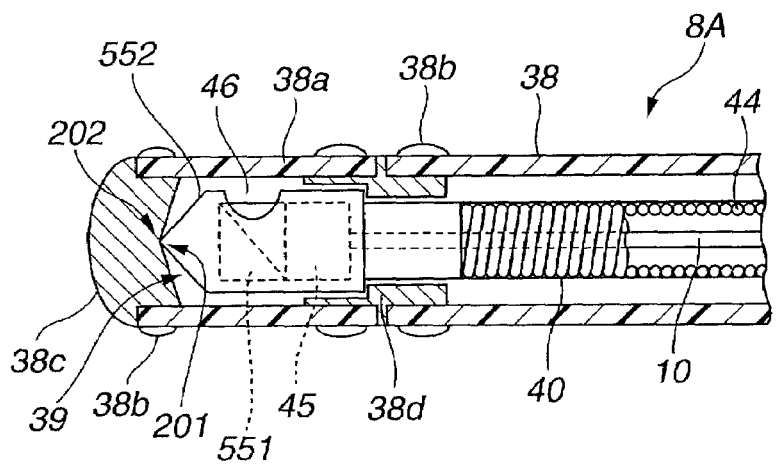
Figure 64:
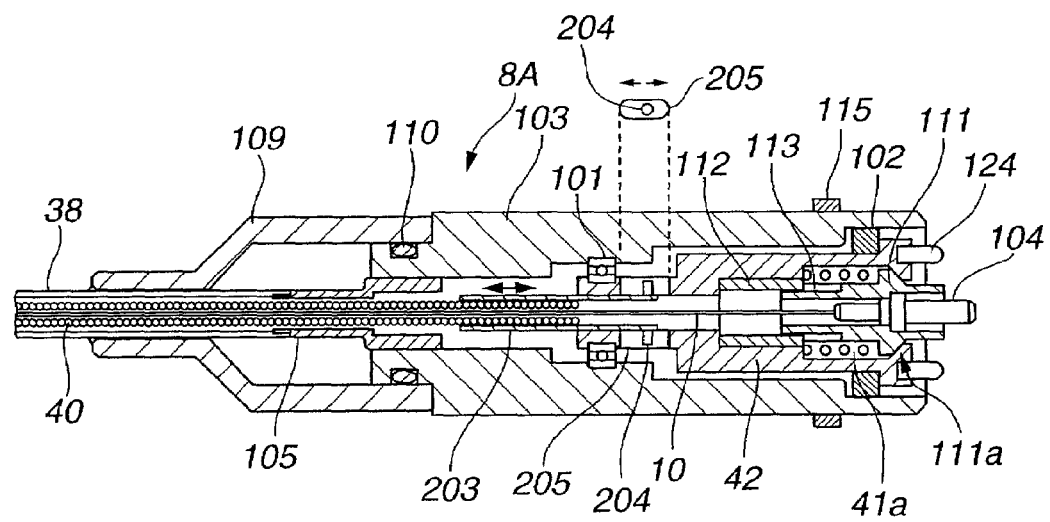

FIG. 63 and FIG. 64 relate to a sixteenth embodiment according to the present invention, FIG. 63 is a configurational diagram showing the configuration of the tip of an optical probe device, and FIG. 64 is a configurational diagram showing the configuration of the base end of the optical probe device shown in FIG. 63.

Figure 65:
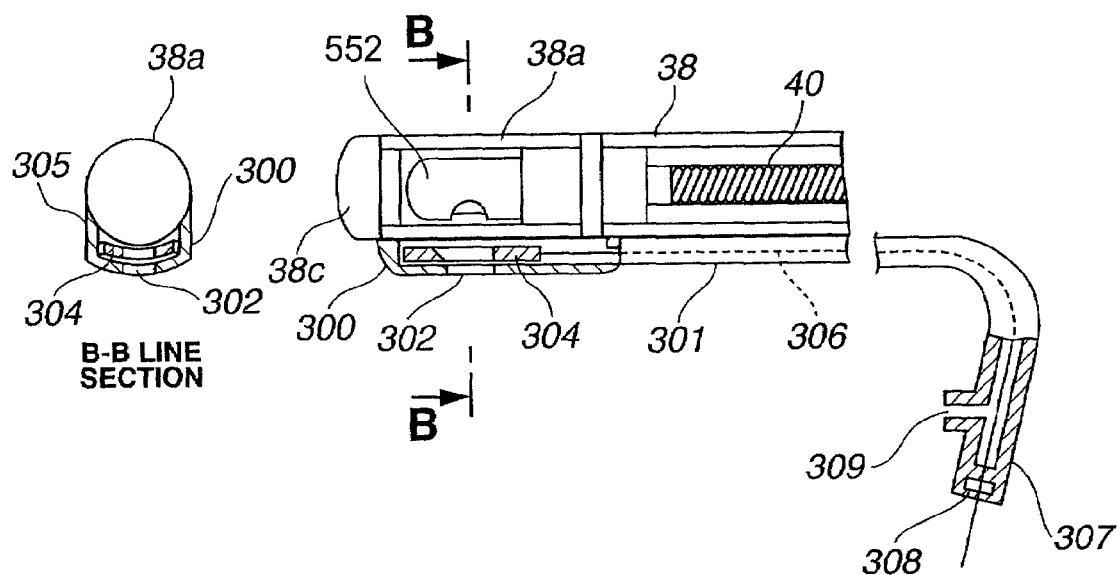
Figure 66:
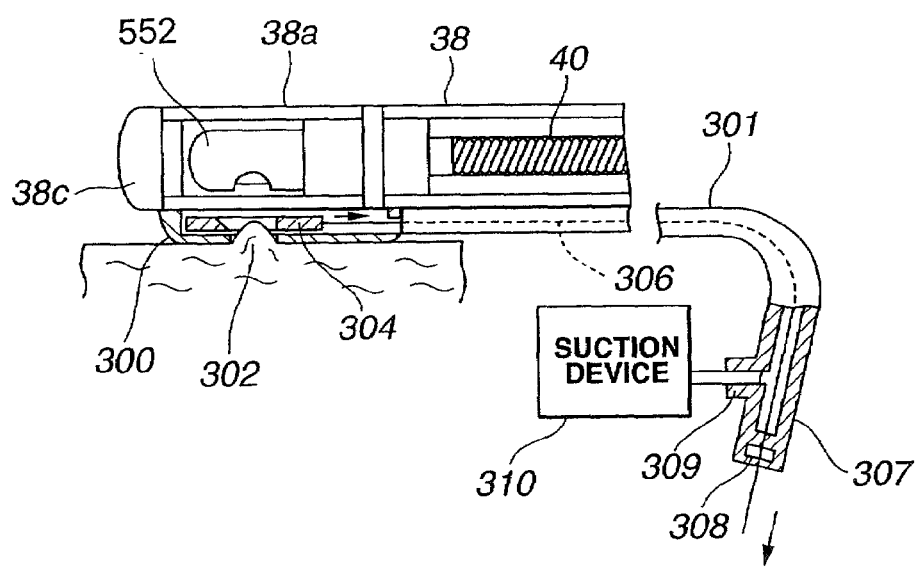

FIG. 65 and FIG. 66 relate to a seventeenth embodiment according to the present invention, FIG. 65 is a configurational diagram showing the configuration of the optical probe device, and FIG. 66 is a diagram for explaining an action of the optical probe device shown in FIG. 65.

DETAILED DESCRIPTION OF THE PREFERRED EMBODIMENTS

Embodiments according to the present invention will be described below with reference to the drawings.

Figure 1:
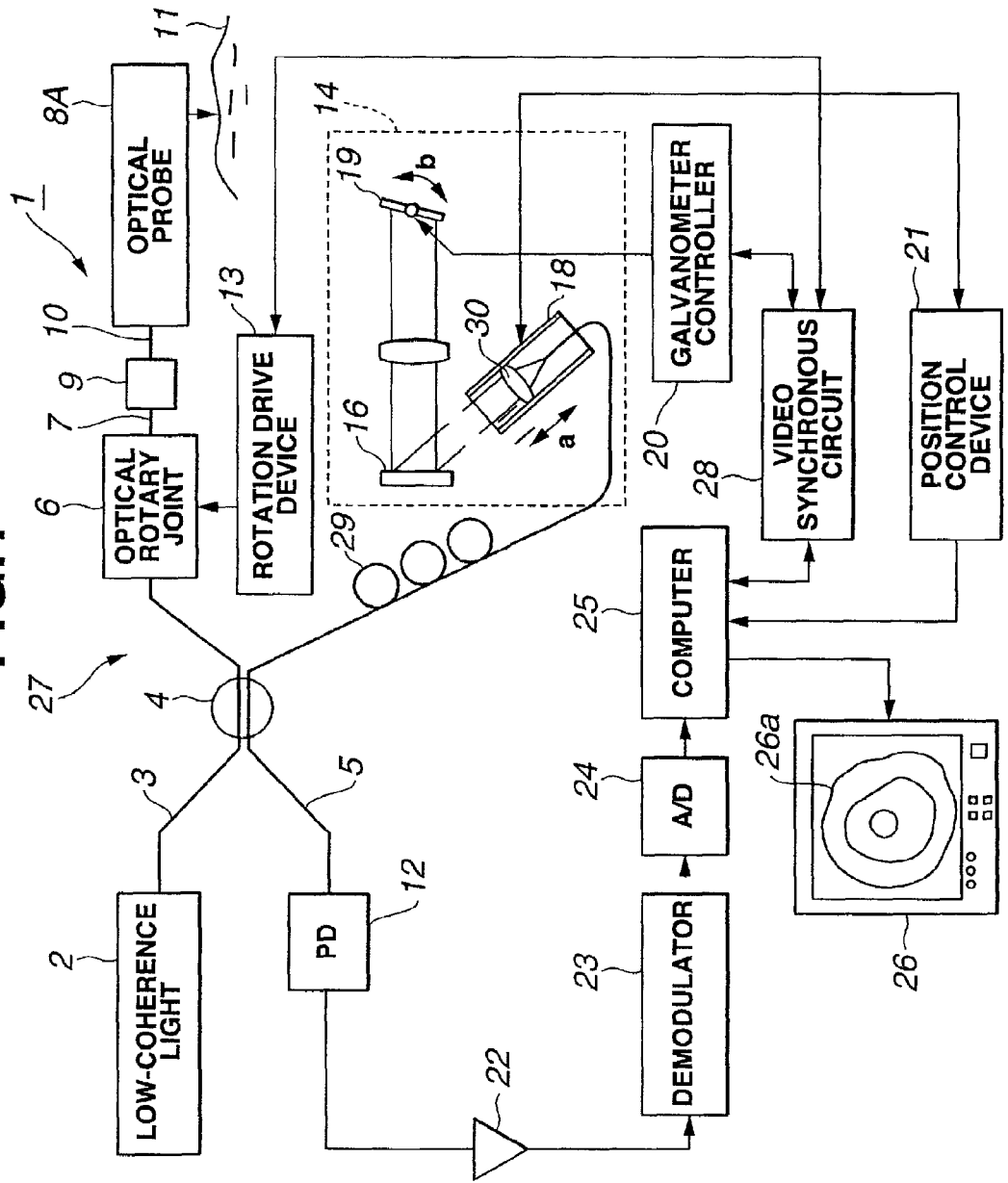
FIG. 1 to FIG. 8 relate to a first embodiment according to the present invention.

First Embodiment:

An optical imaging device (optical tomography device) 1 shown in FIG. 1 is provided with a low-coherence light source 2, for example, a super luminescence diode (hereafter abbreviated as SLD) in an observation device 27. This low-coherence light source 2 is provided with characteristics of low-coherence light exhibiting coherence only in a short-distance range in which the wavelength thereof is, for example, 1,300 nm and the coherence length is, for example, on the order of 17 μm.

That is, in the case where this light is divided into, for example, two portions and, thereafter, the two portions are mixed again, when the difference between two optical path lengths from the division point to the mixing point is within the short-distance range on the order of 17 mm, this light is detected as the light in which interference has occurred, and when the difference between the optical path lengths is larger than that, characteristics show no occurrence of interference.

The light from this low-coherence light source 2 is made to enter one end of a first single mode fiber 3, and is transmitted to the other end surface (tip surface) side. This first single mode fiber 3 is optically coupled to a second single mode fiber 5 in an optical coupler portion 4 on its way. Therefore, the light is divided into two portions in this optical coupler portion 4, and these are transmitted.

On the side nearer to the tip (than is the optical coupler portion 4) of the first single mode fiber 3, an optical rotary joint 6, which performs coupling capable of transmitting light between a non-rotary portion and a rotary portion, is interposed. A connector portion 9 of an optical probe device (hereafter may be abbreviated as optical probe) 8A according to the first embodiment is connected, while being free to attach or detach, to the tip of a third single mode fiber 7 in this optical rotary joint 6. The light from the low-coherence light source 2 is transmitted (guided) to a fourth single mode fiber 10 which is inserted through this optical probe 8A and which is driven to rotate.

The transmitted light is radiated to living-body tissue 11, as a specimen, side from the tip side of the optical probe 8A while being made to scan. A part of the reflected light which has been, for example, scattered on the surface or in the inside of the living-body tissue 11 side is captured, and is returned to the first single mode fiber 3 side through the optical paths in reverse order. A part thereof is transmitted to the second single mode fiber 5 side by the optical coupler portion 4, and is made to enter a photodiode 12 as an example of photodetectors from one end of the second single mode fiber 5. The rotor side of the optical rotary joint 6 is driven to rotate by a rotation drive device 13.

An optical path length-changeable mechanism 14 which changes the optical path length of the reference light is provided on the side nearer to the tip of the second single mode fiber 5 than is the optical coupler portion 4. This optical path length-changeable mechanism 14 is provided with a first optical path length change unit which, in accordance with the optical path length for scanning within a predetermined scanning range in the direction of the depth of the living-body tissue 11 with the optical probe 8A, brings about a high-speed change of optical path length within this scanning range, and a second optical path length change unit which can change the optical path length by on the order of variations in the lengths of the optical probes 8A in order that variations in the lengths can be absorbed when the optical probes 8A are used by exchange.

A grating 16 is placed facing the tip of the second single mode fiber 5 with a collimating lens 30 therebetween. The collimating lens 30 is fitted on a uniaxial stage 18 together with this tip and is free to move in the direction indicated by an arrow a. A galvanometer mirror 19 which can rotate at a minute angle is fitted as a first optical path length change unit interposing this grating (diffraction grating) 16, and this galvanometer mirror 19 is rotation-vibrated as indicated by a reference numeral b with a high speed by a galvanometer controller 20.

A grating 16 is placed facing the tip of the second single mode fiber 5 with a collimating lens 30 therebetween. The collimating lens 30 is fitted on a uniaxial stage 18 together with this tip and is free to move in the direction indicated by an arrow a. A galvanometer 19 which can rotate at a minute angle is fitted as a first optical path length change unit interposing this grating (diffraction grating) 16, and this galvanometer mirror 19 is rotation-vibrated as indicated by a reference numeral b with a high speed by a galvanometer controller 20.

This galvanometer mirror 19 is the one in which reflection is performed by a mirror of a galvanometer and is the one in which an alternating current driving signal is applied to the galvanometer and, therefore, the mirror fitted to the movable part thereof is rotation-vibrated with a high speed.

That is, the driving signal is applied by the galvanometer controller 20 in order that scanning can be performed over a predetermined distance in the direction of the depth of the living-body tissue 11 with a high speed by the optical probe 8A, and by this driving signal, high-speed rotation-vibration is brought about as indicated by reference numeral b.

By this rotation-vibration, the optical path length of the light, which is made to exit from the end surface of the second single mode fiber 5 and which is reflected by the galvanometer mirror 19 so as to return, is changed within the scanning range of a predetermined distance at which scanning is performed in the direction of the depth of the living-body tissue 11.

That is, the first optical path length change unit for producing a tomogram in the direction of the depth is formed by the galvanometer mirror 19. This optical path length change unit by the galvanometer mirror 19 is disclosed in SCIENCE VOL. 276, 1997, pp2037–2039.

The second single mode fiber 5 and the collimating lens 30 are provided on the uniaxial stage 18 which is free to move in the direction of the optical axis thereof as indicated by reference numeral a, and, therefore, become the second optical path length change unit.

On the second single mode fiber 5, fiber loops 29 for adjusting plane of polarization are provided in order to remove an effect of birefringence brought about due to bending of the fiber in a whole coherence system composed of the fiber and the optical probe 8A.

On the other hand, with respect to the case where the optical probe 18 is exchanged, the uniaxial stage 18 forms the second optical path length change unit having an optical path length change range which can absorb variations in the optical path lengths of the optical probes 8A. In addition, in the case where an image in the direction of the depth is produced through the optical path length by the galvanometer mirror 19, a function as an adjustment unit for adjusting offset is also provided in order to make it possible to image from a desired position (for example, the surface position, even when the tip of the optical probe 8A is not in close contact with the surface of the living-body tissue, by changing the optical path length due to the uniaxial stage 18 and, therefore, by adjusting the condition in order that interference occurs from the surface position of the living-body tissue 11).

This uniaxial stage 18 is provided with a motor for moving the stage, and the uniaxial stage 18 is moved in the direction indicated by reference numeral a by applying a driving signal to the motor from a position control device 21.

The light, the optical path length of which has been changed by this optical path length change unit 14, is mixed with the light leaked from the first single mode fiber 3 side in the optical coupler portion 4 provided on the way to the second single mode fiber 5, and both are received by the photodiode 12.

For example, the second single mode fiber 5 is adjusted in order that, in the condition in which the uniaxial stage 18 is adjusted in the neighborhood of the midpoint position in the range of variation, the optical path length from the optical coupler portion 4 to the living-body tissue 11 through the fourth single mode fiber 9, etc., and the tip of the optical probe 8A and the optical path length by way of the second single mode fiber 5 and reflection by the galvanometer mirror 19 on the uniaxial stage 18 become nearly the same length.

Variations in the lengths of (the fourth single mode fibers 10 in) the optical probes 8A are absorbed by adjusting variably the position of the uniaxial stage 18 in accordance with the optical probe to be connected for practical use. In addition to this, the optical path length of the reference light side thereof is changed periodically by high-speed rotation-vibration or high-speed vibration of the galvanometer mirror 19 and, therefore, interference can be brought about with the light reflected at the depth position of the living-body tissue 11, the value of which is equivalent to this optical path length, while the light reflected at the part of other depth can become incoherent.

A signal photoelectrically converted in the aforementioned photodiode 12 is amplified by an amplifier 22 and, thereafter, is input into a demodulator 23. In this demodulator 23, demodulation treatment is performed in order that only the part of the signal of the light having interfered is extracted. The output thereof is input into a computer 25 via an A/D converter 24. In this computer 25, image data corresponding to a tomogram are produced, and are output to a monitor 26 so as to display an OCT image 26a on the display surface thereof.

This computer 25 is connected to the position control device 21. The computer 25 performs the control of the position of the uniaxial stage 18 via the position control device 21. The computer 25 is connected to a video synchronous circuit 28 and, therefore, stores the tomogram data into the internal memory in synchronization with the video synchronizing signal during imaging.

The video synchronizing signal of this video synchronous circuit 28 is transferred to the galvanometer controller 20 and the rotation drive device 13, respectively. Subsequently, for example, the galvanometer controller 20 outputs a driving signal at a period in synchronization with the video synchronizing signal (more specifically, a high-speed first video synchronizing signal of two video synchronizing signals of high-speed and low-speed), the rotation drive device 13 outputs a driving signal in synchronization with the first video synchronizing signal at a period in synchronization with the video synchronizing signal (more specifically, a low-speed second video synchronizing signal), and the light is made to scan in the circumferential direction due to rotation by the rotation drive device 13.

Figure 2:
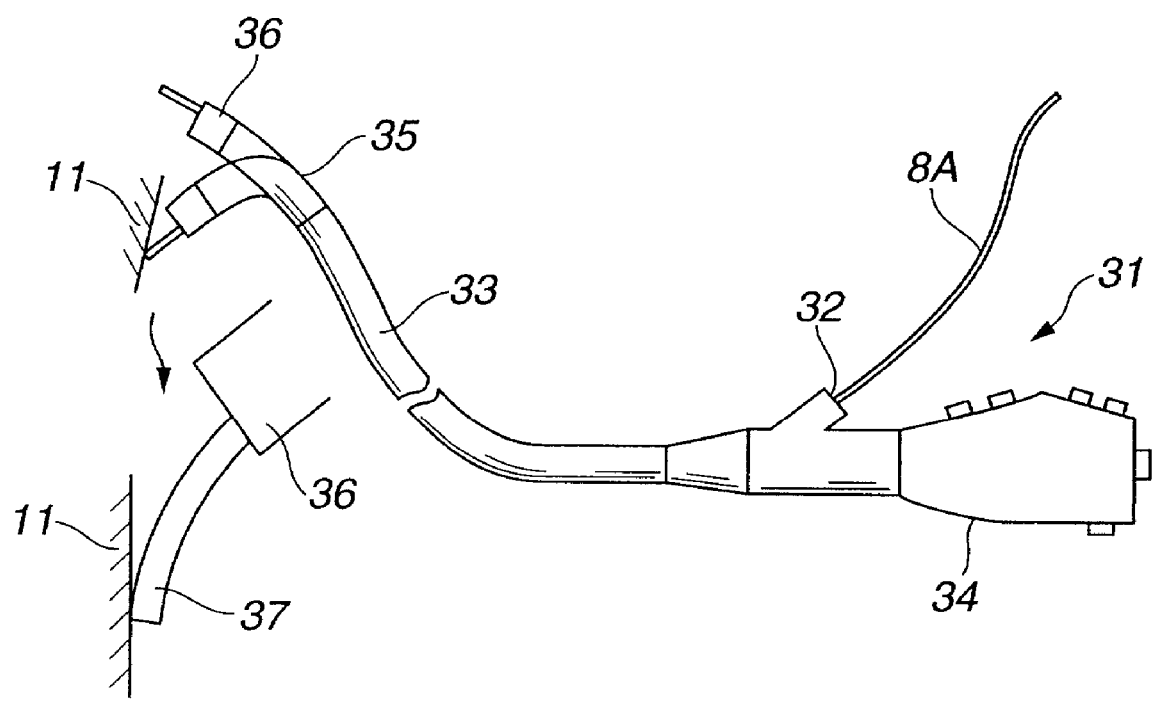

The optical probe 8A according to the first embodiment passes through a forceps insertion hole 32 of the endoscope 31 and a channel for forceps insertion, and the tip side of the optical probe 8A can be protruded from the tip opening thereof, as shown in FIG. 2.

This endoscope 31 includes a slender and pliable insertion portion 33 in order to be inserted into a body cavity with ease, and a wide control portion 34 is provided at the rear end of this insertion portion 33. The forceps insertion hole 32 is provided in the neighborhood of the rear end of this insertion portion 33, and this forceps insertion hole 32 is communicated with the channel for forceps insertion in the inside thereof.

A light guide, although not shown in the drawing, is inserted through the insertion portion 33. The entrance end of this light guide is connected to the light source device. Illumination light is transmitted and is made to exit from an illumination window provided at the tip portion of the insertion portion 33 so as to illuminate an affected area, etc. An observation window is provided adjacently to the illumination window, and an objective optical system is fitted to this observation window in order that the illuminated affected area, etc., can be observed with the optical system. Under observation with the optical observation system at the tip portion of the endoscope 31, the living-body tissue 11 side of the noted part, for example, an affected area, is radiated with low-coherence light by the optical probe 8A, tomogram data of the inside of the living-body tissue 11 are gained, and the OCT image 26a can be displayed on the display surface of the monitor 26.

A curved portion 35 and a (endoscope) tip portion 36 are provided at the tip portion of the insertion portion 33. When the optical probe 8A is inserted through the curved portion 35, or when the tip 37 of the optical probe 8A is protruded from the endoscope tip portion 36 and is contacted with the living-body tissue 11, as shown in FIG. 2, the tip portion 37 of the optical probe 8A is curved at a small curve radius.

Figure 3:
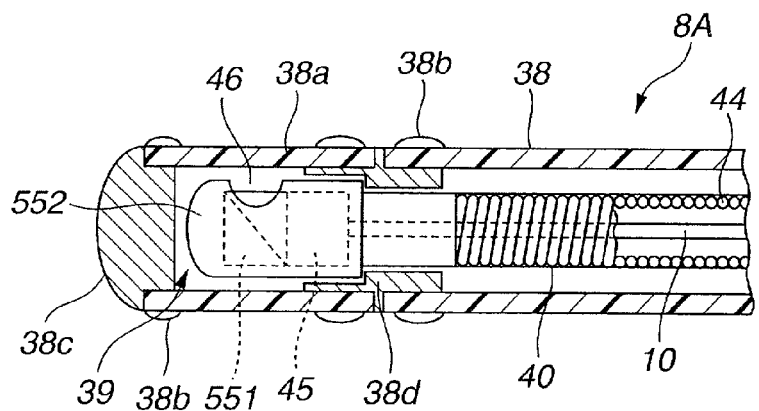
Figure 4:
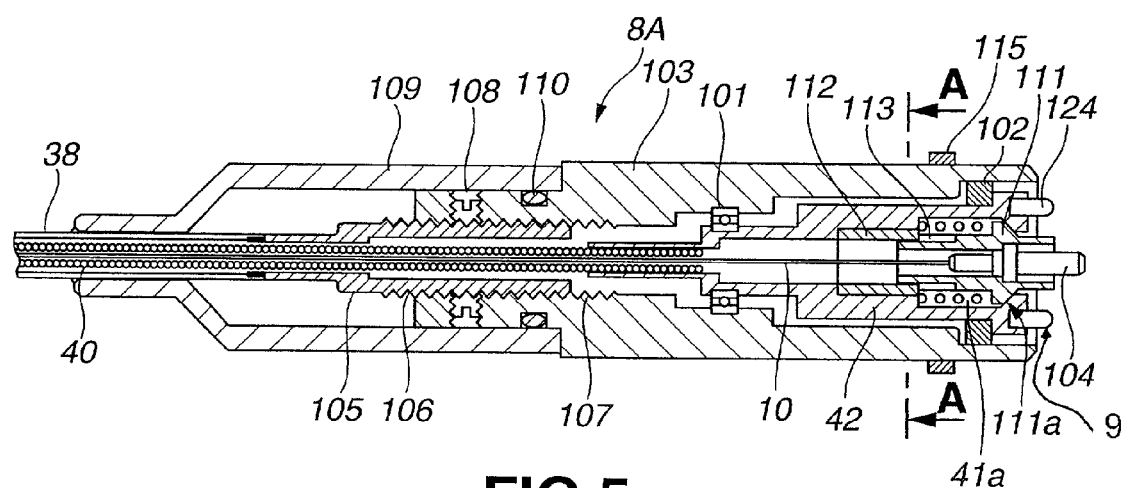
Figure 5:
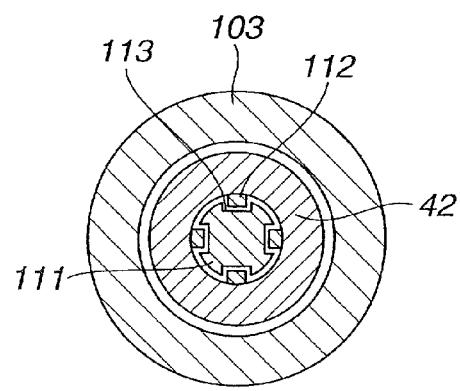

As shown in FIG. 3 to FIG. 5, the optical probe 8A includes an optical sheath 38 composed of a slender tube-shaped resin tube, to which a tip sheath 38a having at least a transparent outer perimeter surface is adhered and fixed by a string winding adhesion portion 38b with a locking member 38d therebetween, a connector potion 9 for connecting the rear end side of the optical sheath 38 to the rotation drive device 13 (constituting an observation device), a flexible shaft 40 which is provided inside the optical sheath 38, which is composed of a coil 44 wound spirally, and which rotates freely to transfer a torque, the fourth single mode fiber 10 provided in the lumen of the flexible shaft 40, a tip unit 39 which is connected to and held at the tip of the flexible shaft 40 and which becomes the light exit•entrance portion, and a rotation transfer connector 42 connected to the rear end of the flexible shaft 40 including a ferrule 104 connected to the rear end of the fourth single mode fiber 10.

In the tip unit 39 placed on the tip side of the optical sheath 38 while being free to rotate, a GRIN lens 45 for condensing the light from the end portion of the fourth single mode fiber 10 and a prism 551 for reflecting the condensed light at the inclined surface so as to exit in the perpendicular direction are provided. These are covered with a tip housing (may be abbreviated briefly as housing) 552 (fitted to the tip of the flexible shaft 40) including a window portion 46 to become the exit•entrance portion of the light from the prism 551.

A seal member 38c is fixed to the tip of the tip sheath 38a with the string winding adhesion portion 38b, and the tip is sealed watertight. The locking member 38d and the rear end surface of the tip housing 552 are in contact with each other.

The optical sheath 38 is not necessarily transparent except the tip sheath 38a as long as it is flexible. The locking member 38d performs joining of the tip of the optical sheath 38 and the tip sheath 38a as well.

The rotation transfer connector 42 connected to the rear end of the flexible shaft 40 is held by ball bearings 101 and slide bearings 102 while being free to rotate about the center of the outer cylinder member 103 of the connector potion 9. The rear end of the fourth single mode fiber 10 is inserted with high precision into the center of the ferrule 104 which is a member commonly used in optical communications as a connector for an optical fiber, and is optically polished with the rear end surface of the ferrule 104.

The rear end of the optical sheath 38 is fixed to a sheath stopping member 105, an external thread portion 106 formed on the outer perimeter surface of the sheath stopping member 105 and an internal thread portion 107 formed on the inner surface of the outer cylinder member 103 are thread-engaged. When the thread engagement position described below of the external thread portion 106 and the internal thread portion 107 is determined, the sheath stopping member 105 is fixed to the outer cylinder member 103 with setscrews 108 in order to prevent movement of the sheath stopping member 105. The tip of the outer cylinder member 103 is covered with a folding prevention member 109, and the outer cylinder member 103 and the folding prevention member 109 are connected watertight to each other with an O-ring 110.

The ferrule 104 is fixed to the ferrule retainer 111, and this ferrule retainer 111 is connected to the rotation transfer connector 42 with a spring 41a therebetween.

Figure 6:
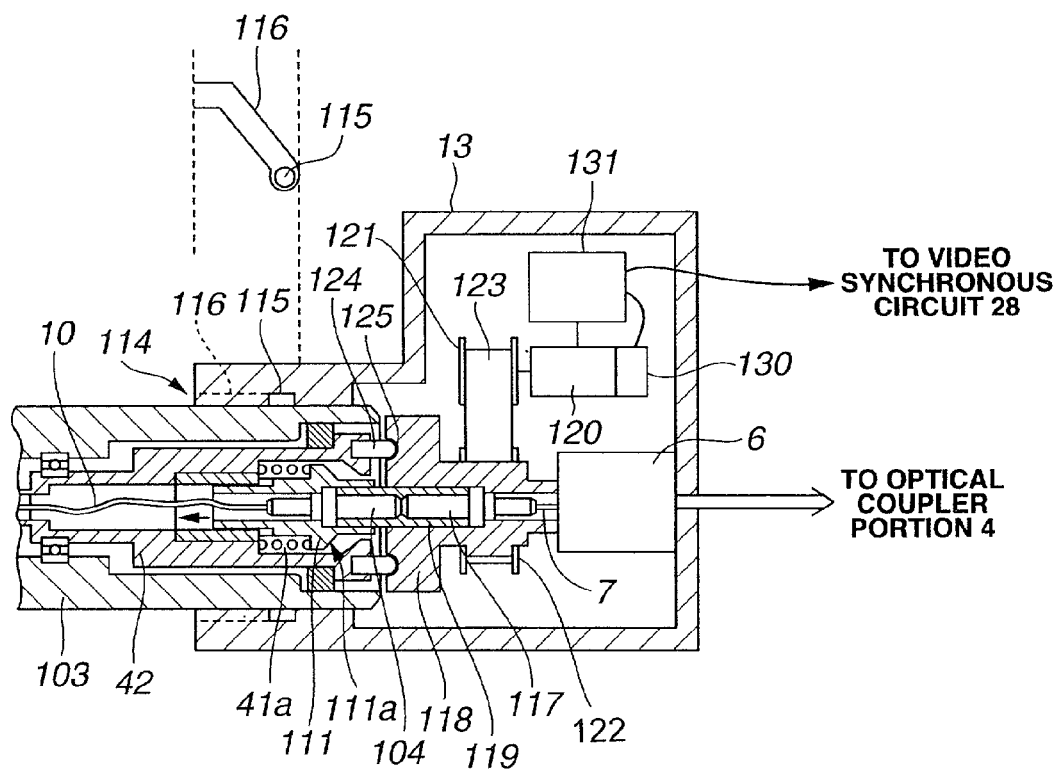

Regarding connection of the connector potion 9 and the rotation drive device 13, as shown in FIG. 6, when the outer cylinder member 103 is coupled to an insertion hole 114 of the rotation drive device 13, the insertion amount thereof is regulated by the distance in the longitudinal direction of a cam pin 115 formed on the outer perimeter surface of the outer cylinder member 103 and a cam groove 116 formed on the inner surface of the insertion hole 114.

On the other hand, the tip of the third single mode fiber 7 in the optical rotary joint 6 is inserted into the center of the ferrule 117 with high precision, and is optically polished with the tip surface of the ferrule 117.

The ferrule 117 is fixed to a sleeve 119 formed at the center axis of the connection member 118 connected to the rotation transfer connector 42, and the connection member 118 is driven to rotate by a motor 120. This will be described in detail. A pulley 121 provided on the rotation axis of the motor 120 and a pulley portion 122 provided on the outer perimeter surface of the connection member 118 are connected by a toothed belt 123 and, therefore, rotation of the motor 120 is transferred to the connection member 118. The rotation of the motor 120 is controlled by a rotation control circuit 131 which detects the condition of rotation with an encoder 130 provided at the rotation axis of the motor 120.

When the outer cylinder member 103 is inserted at the predetermined position of the insertion hole 114 of the rotation drive device 13, a rotation transfer pin 124 provided at the rear end of the rotation transfer connector 42 is fitted into a transfer groove 125 formed at the tip of the connection member 118 and, therefore, the torque is transferred to the rotation transfer connector 42.

Under this condition, the ferrule 104 and the ferrule 117 are connected with each other in the sleeve 119, and optical connection is performed. At this time, the ferrule 104 and the ferrule retainer 111 are moved toward the tip, and the spring 41a is compressed. The ferrules are pressed and fixed to each other by reaction force of this spring 41a. At this time, the ferrule retainer 111 is supported only by the spring 41a and, therefore, is in a floated state in the rotation transfer connector 42. The rotation center of the probe and the rotation center of the drive portion may deviate from each other due to precision in processing and assembling. When rotation is performed under this condition, stress is applied to the sleeve 119 and the ferrule 104 and, therefore, optical connection may be affected adversely.

In the present embodiment, since the ferrule retainer 111 is in the floated state in the rotation transfer connector 42 while being supported by the spring 41a, this deviation of the rotation centers can be absorbed.

Since the inclined portion 111a is provided in the ferrule retainer 111, when the probe is removed, the ferrule retainer 111 returns to the original position while being centered and, therefore, at the time of subsequent attachment or detachment, connection can be performed smoothly without deviation in the positional relation between the ferrule 104 and the sleeve 119.

As shown in FIG. 5 which is a sectional view of the section indicated by line A—A in FIG. 4, rotation stoppers 112 formed in the rotation transfer connector 42 are fitted into notch portions 113 provided on the outer perimeter surface of the ferrule retainer 111 and, therefore, rotation of the ferrule 104, which has been inserted into the sleeve 119 under a condition that the rotation transfer connector 42 has not rotated due to inadequate fitting of the rotation transfer pin 124 and the transfer groove 125, can be prevented.

The rotation transfer connector 42 is held watertight in the connector potion 9 while being free to rotate, the connector potion 9 has a watertight structure as well and, therefore, the whole optical probe 8A has a watertight structure. By filling the inside thereof with refractive index matching water for preventing reflection and is subjected to use (regarding the refractive indices of the prism 551 in the optical unit 39 and the sheath which are in a condition that the difference in the refractive indices is large due to the small refractive index of air present therebetween, since the refractive indices are made to be nearly the same by the refractive index matching water), reflection at the boundary surface therebetween is reduced and, therefore, an OCT image having excellent image quality can be produced. In addition, (because of the watertight structure) the optical probe 8A can be easily disinfected with a disinfectant solution, etc., be inserted (directly or through the cannel of the endoscope) in a body cavity, and be subjected to use.

The light transmitted with the third single mode fiber 7 is transmitted to the fourth single mode fiber 10 with the optical connector. The rotation by the rotation drive device 13 is transferred to the flexible shaft 40 with the rotation transfer connector 42.

The transmitted light of the fourth single mode fiber 10 is transmitted to the tip unit 39, is totally reflected by the prism 551 of the tip unit 39 at the inclined surface thereof in order that the exit direction is changed to the perpendicular direction, and is made to exit to the outside as inspection light via the window portion 46 through the optical sheath 38. Subsequently, the reflected light from the living-body tissue is received, and is transmitted to the fourth single mode fiber 10 again. Since the tip of the flexible shaft 40 is connected to the tip unit 39, the flexible shaft 40, the tip unit 39, and the fourth single mode fiber 10 are rotated integrally.

On the side at hand of the optical probe 8A thus configured according to the present embodiment, the whole rotation transfer connector 42 is rotated while being supported by the ball bearings 101 and the slide bearings 102 and, therefore, transfers rotation to the flexible shaft 40. The relative position between the flexible shaft 40 and the optical sheath 38 is changed by the amount of screwing of the sheath stopping member 105 on the side at hand into the outer cylinder member 103 using the external thread portion 106 and the internal thread portion 107. When the amount of screwing is changed in order that the optical sheath 38 is moved in the direction toward the tip relative to the main body, finally, the rear end surface of the tip housing 552 is contacted with the locking member 38d.

When the optical sheath 38 is moved furthermore, since the length of the flexible shaft 40 is regulated by the interval between the locking part of the locking member 38d at the tip and the shaft stopping member 105, the flexible shaft 40 is elongated by elastic deformation.

Consequently, the tip housing 552 is contacted with the locking member 38d while, at the rear end surface, the flexible shaft 40 is applied with tension in the direction toward the side at hand.

Therefore, during the use of the optical probe 8A, when the optical probe 8A is curved and the inner surface of the flexible shaft 40 is contacted with the inner surface of the optical sheath 38, the movement of the tip housing 552 is canceled by the amount of elongation of the flexible shaft elongated in advance, and the tip housing 552 is rotated at the same position relative to the probe longitudinal direction on all occasions.

As described above, in the present embodiment, since the tip housing 552 is not moved, a dead space at the tip can be reduced and, therefore, operating ease for the operator during observation is improved. Since the tip housing 552 is not moved, the beam exit portion is not changed and, therefore, the operator can grasp the beam exit portion with ease.

Since optical connection between the ferrule 104 and the ferrule 117 can be performed stably, optical loss can be reduced, improvement of image quality is brought about and, in addition, attachment and detachment of the ferrule 104 can be performed with reliability.

Figure 7:
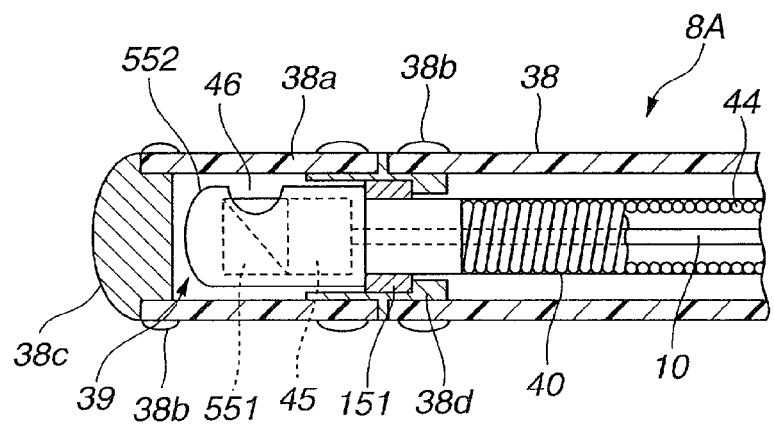

As shown in FIG. 7, the tip bearings 151 made of a rigid resin, for example, Derlin and polycarbonate, may be interposed between the rear end surface of the tip housing 552 and the locking member 38d. According to such a configuration, friction between the tip housing 552 and the locking member 38d is reduced by the tip bearings 151, and, therefore, the rotation of the flexible shaft 40 is transferred smoothly.

Figure 8:
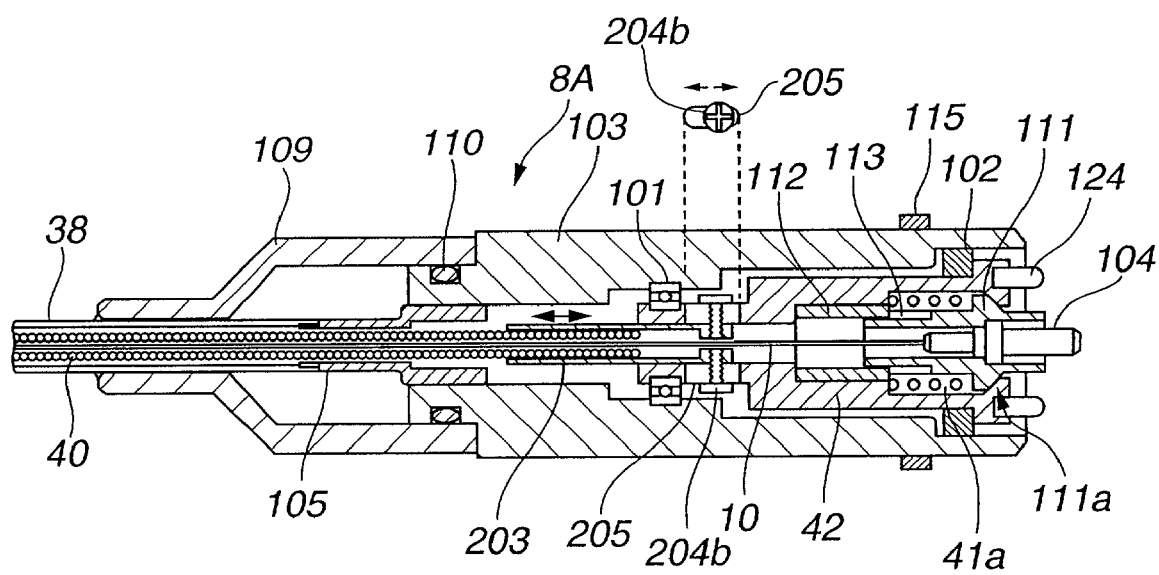

As shown in FIG. 8, regarding the configuration at the rear end of the optical probe 8A, a shaft stopping member 203, to which the rear end of the flexible shaft 40 is connected, may be provided, the setscrew 204b provided on the outer perimeter surface of the shaft stopping member 203 may be fitted into a rectangular hole 205 formed on the rotation transfer connector 42 while being capable of sliding and, therefore, the rotation may be transferred to the flexible shaft 40, and at the same time, the movement distance of the shaft stopping member 203 in the longitudinal axis direction may be regulated.

In case the configuration of the proximal end of the optical probe 8A is provided as shown in FIG. 8 and the configuration of the distal end of the optical probe 8A is provided as shown in FIG. 63, the length of the flexible shaft 40 can be adjusted and the position thereof can be fixed within the range of the major axis distance of the rectangular hole 205. When the flexible shaft 40 is adjusted to be somewhat short, a tensile tension can be applied to the flexible shaft 40 while the rear end surface of the tip housing 552 and the locking member 38d are always in contact with each other. The movement of the tip housing 552 in the longitudinal direction can be regulated by this tensile tension. Conversely, when the flexible shaft 40 is adjusted to be somewhat long, a compressive tension can be applied to the flexible shaft 40 while a pointed portion 201 and a dent portion 202 are always in contact with each other. The movement of the tip housing 552 in the longitudinal direction can be regulated by this compressive tension.

Second Embodiment:

Only the part different from that in the first embodiment will be described with reference to FIG. 9 to FIG. 14.

Figure 9:
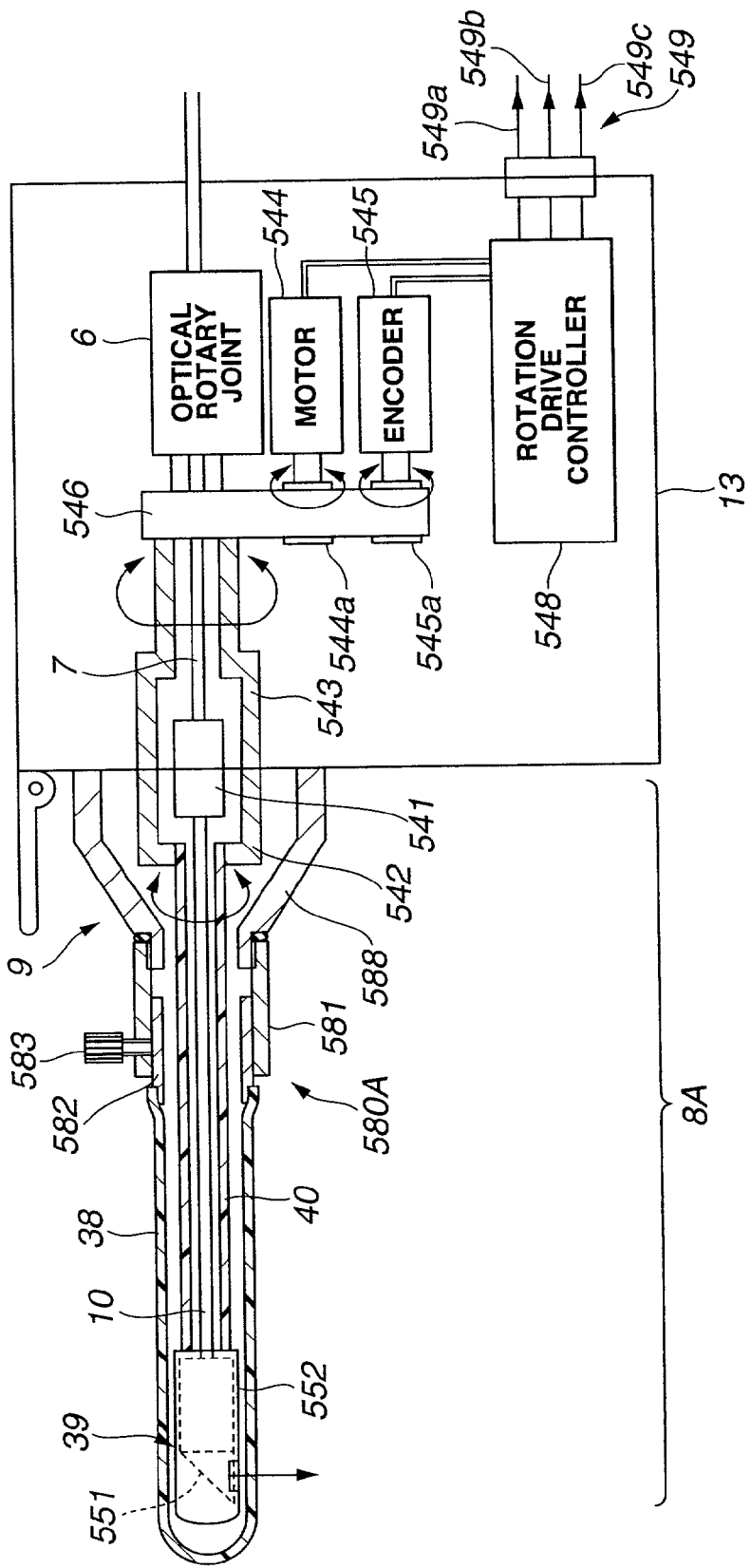
FIG. 9 to FIG. 14 relate to a second embodiment according to the present invention.
Figure 10:
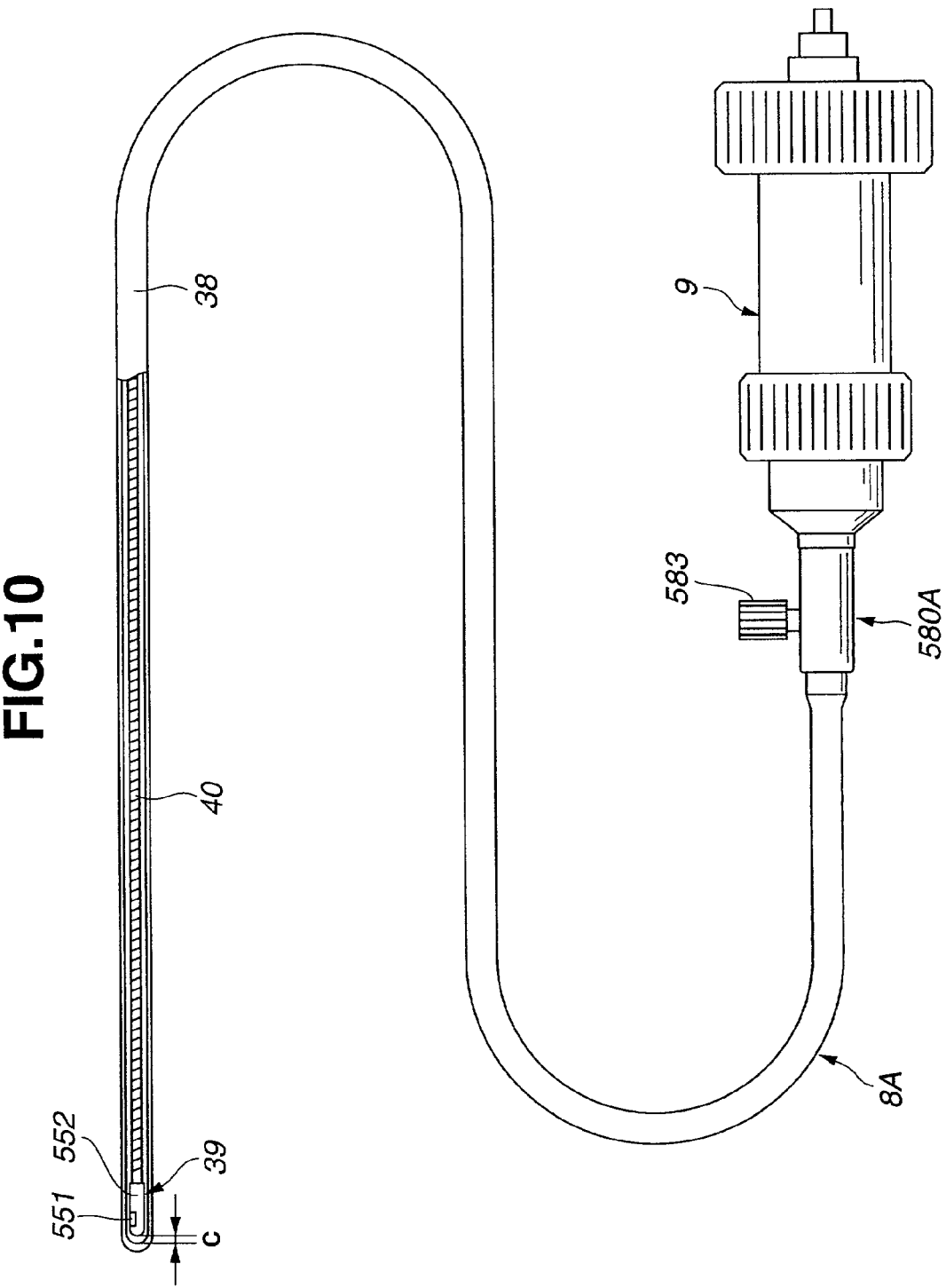

FIG. 9 shows schematic configurations of an optical probe 8A and a rotation drive device 13 according to the present embodiment. FIG. 10 shows the whole of the optical probe 8A.

As shown in FIG. 9 and FIG. 10, the optical probe 8A includes an optical sheath 38 composed of a slender tube-shaped resin tube, a connector potion 9 for connecting the base end side of the optical sheath 38 to the rotation drive device 13 (constituting an observation device), a flexible shaft 40 which is provided inside the optical sheath 38 and which rotates freely to transfer a torque, a fourth single mode fiber 10 provided in the lumen of the flexible shaft 40, a tip unit 39 which is connected to and held at the tip of the flexible shaft 40 and which becomes a light exit•entrance portion, and a rotation transfer connector 542 connected to the rear end of the flexible shaft 40, and a connector potion 9 provided with an optical connector 541 connected to the rear end of the fourth single mode fiber 10. The rear end of the sheath 38 is connected to the connector potion 9 with a sheath length adjustment mechanism 580A therebetween as described below with reference to FIG. 11 or FIG. 12.

The tip of the optical sheath 38 is blocked watertight with a seal portion. In the tip unit 39 placed on the tip side of this optical sheath 38 while being free to rotate, for example, a GRIN lens for condensing the light from the tip portion of the fourth single mode fiber 10, although not shown in the drawing, and a prism 551 for reflecting the condensed light at the inclined surface so as to exit in the perpendicular direction, are provided. These are covered with a tip housing (may be abbreviated briefly as housing) 552 (fitted to the tip of the flexible shaft 40) except a window portion for exit from the prism 551.

As described below, the connector potion 9 has a watertight structure as well and, therefore, the whole optical probe 8A has a watertight structure. By filling the inside thereof with refractive index matching water for preventing reflection and is subjected to use (regarding the refractive indices of the prism 551 in the optical unit 39 and the sheath which are in a condition that the difference in the refractive indices is large due to the small refractive index of air present therebetween, since the refractive indices are made to be nearly the same by the refractive index matching water), reflection at the boundary surface therebetween is reduced and, therefore, an OCT image having excellent image quality can be produced. In addition, (because of the watertight structure) the optical probe 8A can be easily disinfected with a disinfectant solution, etc., be inserted (directly or through the cannel of the endoscope) in a body cavity, and be subjected to use.

The rotation drive device 13, to which the connector potion 9 at the rear end of this optical probe 8A is attached while being freely detachable, includes a hollow rotating shaft 543 and an optical rotary joint 6 connected to the rear end of this rotating shaft 543. An optical connector 541 is provided at the tip portion of the rotating shaft 543, and this optical connector 541 and the optical rotary joint 6 are connected by a third single mode fiber 7 placed in the hollow portion of the rotating shaft 543.

The rotation drive device 13 includes a motor 544 for rotating the rotating shaft 543 and an encoder 545 for detecting rotation of the rotating shaft 543. A belt 546 is looped over a motor pulley 544a fitted to the rotating shaft of the motor 544, an encoder pulley 545a fitted to the rotating shaft of the encoder 545, and the rotating shaft 543.

The motor 544 and the encoder 545 are connected to a rotation drive controller 548.

Next, actions of this rotation drive device 13 will be described. The rotation of the motor 544 is transferred to the motor pulley 544a, and is transferred to the rotating shaft 543 and the encoder pulley 545a by the belt 546. The encoder 545 detects the rotation speed of the rotating shaft 543, and controls the driving current of the motor 544 with the rotation drive controller 548 in order that the rotation speed becomes a designated speed. Accordingly, the rotating shaft 543 is rotated constantly at a designated speed. The rotation angle of the rotating shaft 543 is detected with the encoder 545, and a signal 549 is transferred to the video synchronous circuit 28 side via the rotation drive controller 548.

This signal 549 is composed of an A-phase signal 549a which is an A-phase pulse wherein one rotation has been divided into 256 pulses, a B-phase signal 549b of B-phase which has a 45 degrees phase shift relative to the A-phase, and a one-rotation signal 549c wherein one pulse corresponds to one rotation.

Actions of the optical probe 8A will be described except the sheath length adjustment mechanism 580A. The light transmitted with the third single mode fiber 7 is transmitted to the fourth single mode fiber 10 with the optical connector 541. The rotation of the rotating shaft 543 is transferred to the flexible shaft 40 with the rotation transfer connector 542.

The transmitted light of the fourth single mode fiber 10 is transmitted to the tip unit 39, is totally reflected by the prism 551 of the tip unit 39 at the inclined surface thereof in order that the exit direction is changed to the perpendicular direction, and is made to exit to the outside as inspection light through the transparent optical sheath 38. Subsequently, the reflected light from the living-body tissue is received, and is transmitted to the fourth single mode fiber 10 again. Since the tip of the flexible shaft 40 is connected to the tip unit 39, the flexible shaft 40, the tip unit 39, and the fourth single mode fiber 10 are rotated integrally.

Figure 11:
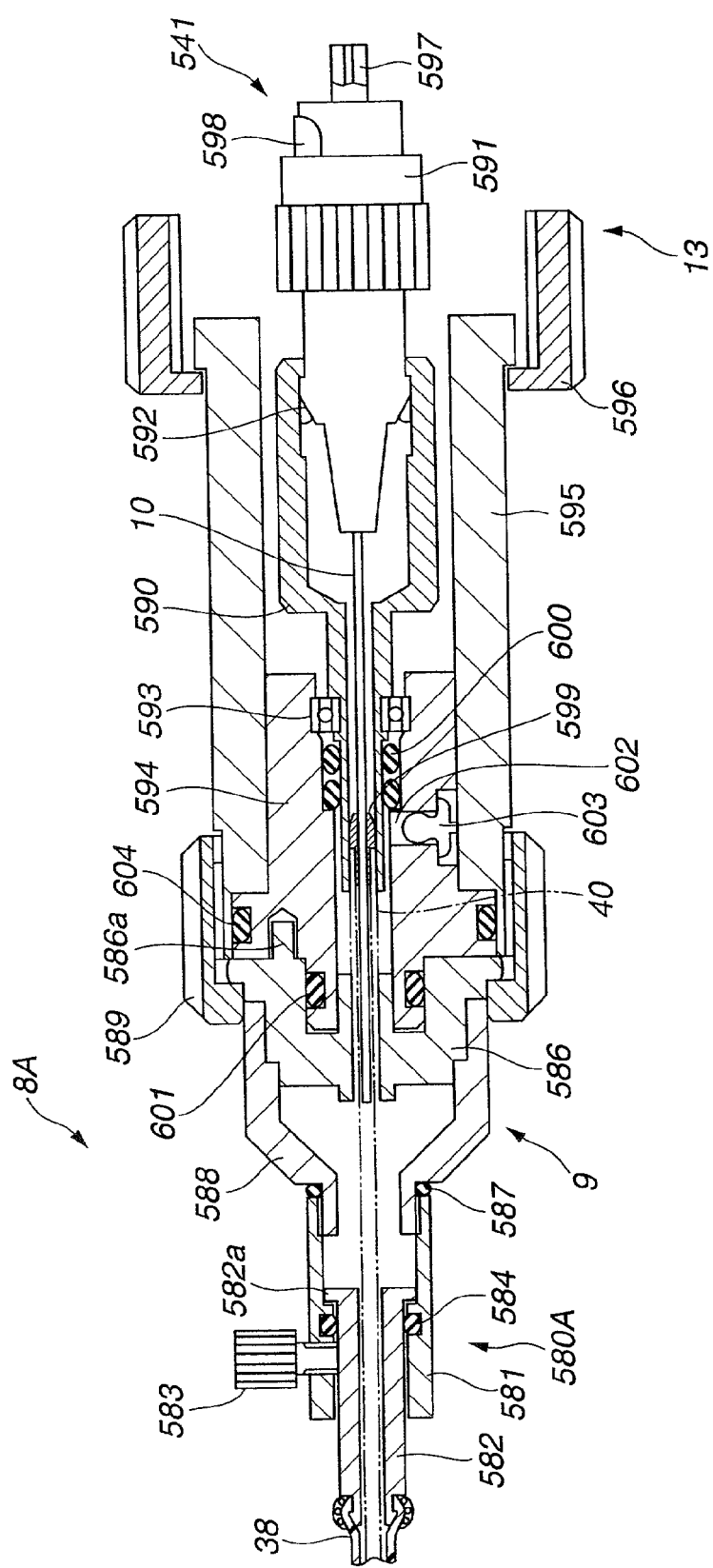

FIG. 11 shows the detailed configuration of the connector potion 9 connected to the rotation drive device 13 while being free to attach or detach. In the present embodiment, the sheath length adjustment mechanism 580A is provided at the front part of this connector potion 9.

The rear end of the optical sheath 38 is fitted to a pipe 581 for fixing and is fixed to the tip of a sheath base 582 which is free to slide with an adhesive, etc., for ensuring watertightness. This sheath base 582 is pressed and fixed by a setscrew 583 thread-engaged with a threaded hole of the pipe 581 for fixing (connected and fixed to the connector potion 9).

The rear end of the pipe 581 for fixing is fixed to the tip of a cover 588 by thread engagement, the rear end of this cover 588 is fixed to a junction block 586, and this junction block 586 is connected and fixed to a connector case 595 with a retaining ring 589 by thread engagement.

The flexible shaft 40 protruding from the rear end portion of the optical sheath 38 is passed through the hole in the center portion of the junction block 586 and through the hollow portion of a pedestal 594, and is fitted to a connector stopper 590, the tip of which is placed in the pedestal 594. This connector stopper 590 is coupled to the optical connector 541 with an adhesion portion 592.

The connector stopper 590 is held by the pedestal 594 with bearings 593 therebetween while being free to rotate. The pedestal 594 is fitted to the rotation drive device 13 with the connector case 595 and a clamp ring 596 while being free to attach or detach.

The rear end surface of the junction block 586 is pressed against the front end surface of the pedestal 594, and the junction block 586 is fixed to the connector case 595 with the retaining ring 589 while being free to attach or detach.

In this case, a protrusion 586a for preventing rotation provided at the rear end surface of the junction block 586 is fitted into a concave portion provided at the end surface of the pedestal 594 in order that the junction block 586 is prevented from rotating accidentally.

The optical connector 541 includes a ferrule 597 for connecting the fourth single mode fiber 10 and the rotation drive device 13 and a rotation stopper 598 for regulating the direction of connection of the optical connector 541.

By rotating the optical connector 541, the connector stopper 590 is rotated, and the rotation is transferred to the flexible shaft 40. The connector stopper 590, the flexible shaft 40, and the single mode fiber 10 are adhered with watertight adhesion portion 599 while watertightness is ensured.

O-rings 600 are provided as watertight seals between the connector stopper 590 and the pedestal 594. An O-ring 601 having a function as a watertight seal is also provided between the junction block 586 and the pedestal 594.

By these watertight seals, refractive index matching water put between the optical sheath 38 and the flexible shaft 40 does not leak out, and the refractive index matching water can be encapsulated from an injection hole 602 provided in the pedestal 594.

The water infiltrated into the inside through the gap of the flexible shaft 40 does not leak out as well. Usually, the injection hole 602 is blocked with an injection water cover 603.

An O-ring 604 is interposed between the pedestal 594 and the connector case 595 and, therefore, watertightness is ensured.

Figure 12:
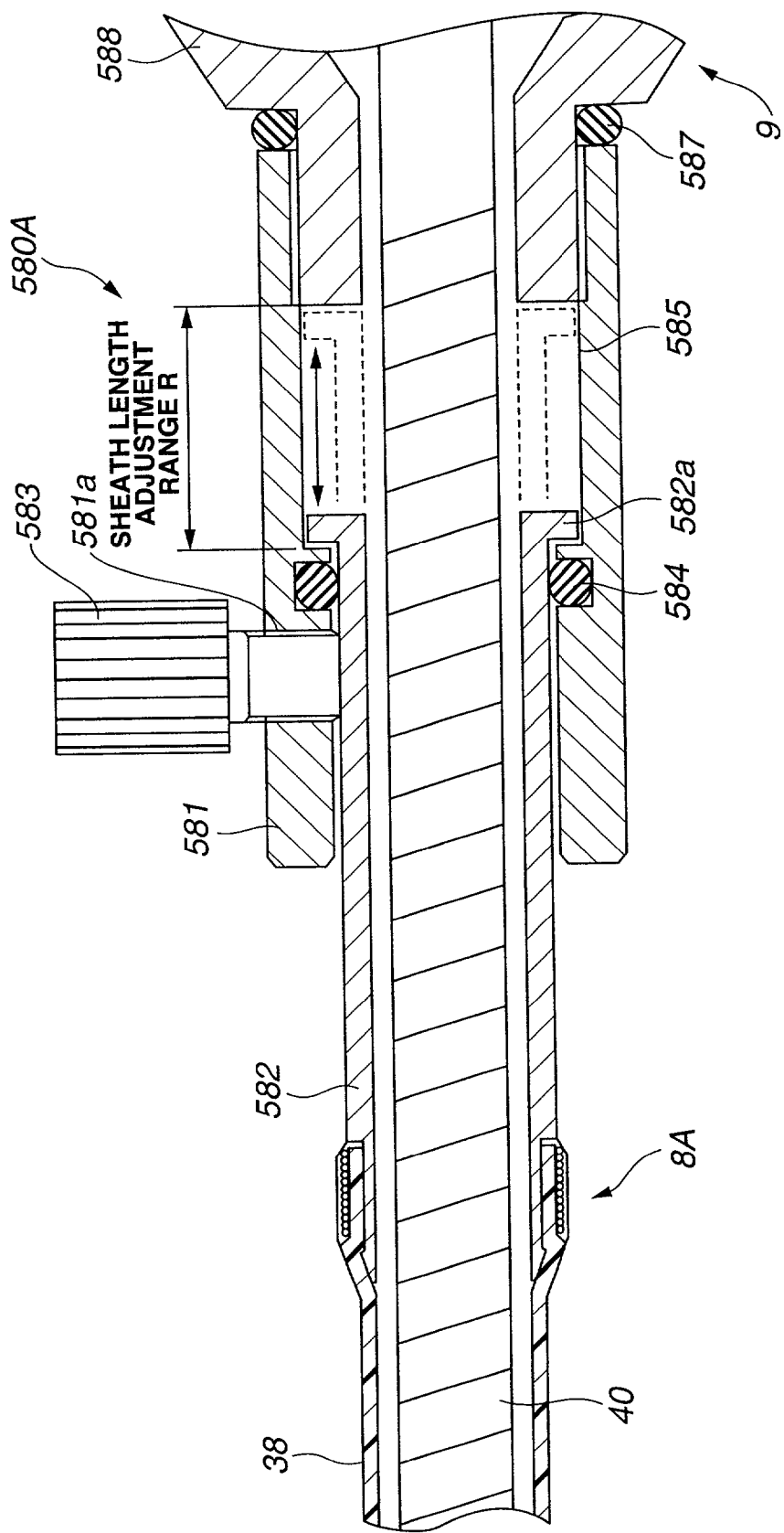

FIG. 12 shows the detailed configuration of the sheath length adjustment mechanism 580A provided at the front part of the connector potion 9 shown in FIG. 11.

The base end portion of the sheath 38 is fixed watertight to the sheath base 582 with string winding and adhesion. The outer perimeter surface of this sheath base 582 is a slide surface which is free to slide over the inner perimeter surface on the tip side of the pipe 581 for fixing and which can slide relatively in the direction of the axis.

An O-ring 584 is provided on the inner perimeter surface near to the tip of the pipe 581 for fixing while being in press contact with the sheath base 582 and, therefore, watertightness of this slide surface is ensured. At the position on the side nearer to the tip of the pipe 581 for fixing than is the O-ring 584, a thread hole 581a penetrating in the direction perpendicular to the probe axis is provided, and a setscrew 583 is screwed into this thread hole 581a.

A sheath length adjustment groove 585 having a length adequate for adjusting the sheath length is provided on the side nearer to the base end of the pipe 581 for fixing than is the O-ring of the inner perimeter surface.

That is, the position at which the sheath base 582 is fixed to the pipe 581 for fixing is changed within the sheath length adjustment range R (shown in FIG. 12) from the forward end to the rearward end of the sheath length adjustment groove 585 and, therefore, the sheath length adjustment mechanism 580A capable of changing the length of the sheath length is formed.

On the other hand, relative to the sheath length adjustment groove 585, a flange 582a is provided at the base end of the sheath base 582. The outer diameter of the flange 582a is specified to be smaller than the inner diameter of the sheath length adjustment groove 585, and be larger than the inner diameter of the tip of the pipe 581 for fixing. Consequently, the sheath base 582 cannot be pulled out.

An O-ring 587 is interposed between the rear end of the pipe 581 for fixing and a height difference portion of the cover 588, to which this is fitted by thread engagement, and, therefore, watertightness with respect to the thread engagement portion adjacent thereto is ensured.

Figure 13:
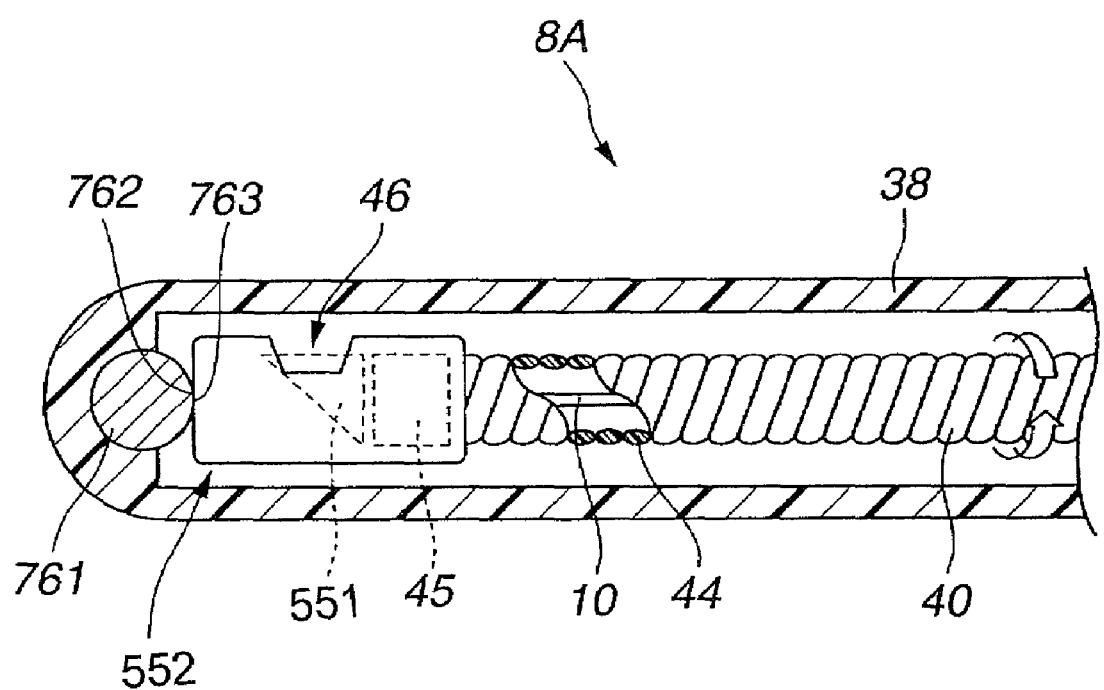

As shown in FIG. 13, a part of a metal ball 761 is embedded in the inner surface tip of the optical sheath 38 according to the present embodiment, and the contact point 762 of the metal ball 761 is in point contact with the tip surface 763 of the tip housing 552.

According to the aforementioned configuration, since the part of the metal ball 761 exposed from the inner surface tip of the optical sheath 38 is in point contact with the tip smooth surface of the housing 552, frictional resistance of the housing 552 is low and rotation is performed about the line bonding the point of point contact with the metal ball 761 and the center. Consequently, the rotation of the housing 552 can be stabilized without variations while the clearance between the tip of the housing 552 and the inner surface tip of the optical sheath 38 can be minimized.

When the insertion length of the sheath base 582, to which the rear end of the sheath 38 is fixed, into the pipe 581 for fixing is controlled by the watertight sheath length adjustment mechanism 580A so as to adjust the sheath length, and the contact point 762 of the metal ball 761 and the tip surface 763 of the tip housing 552 are made to contact and are fixed with the setscrew 583 in order that the tip clearance C (refer to FIG. 10) becomes zero, even in the case of the optical probe 8A having a different sheath length, the contact point 762 of the metal ball 761 and the tip surface 763 of the tip housing 552 can be contacted properly. If necessary, the sheath length can be adjusted in order that the contact point 762 and the tip surface 763 may be press-contacted as well. Furthermore, even when the probe does not include the metal ball 761 at the tip of the sheath 38, by adjusting the sheath length in a manner similar to that described above, the tip clearance C (refer to FIG. 10) can be set at minimum value in order that the tip unit 39 does not contact with the seal portion at the sheath tip.

That is, even when there are variations in the sheath lengths as in the case where manufacture is performed without precise control of the sheath length, since the tip clearance C can be set and kept at a proper value by the sheath length adjustment mechanism 580A, the yield can be increased, the productivity can be improved, and the manufacturing cost can be reduced.

By variably setting the value of the tip clearance C, it is possible to respond flexibly in accordance with operational environments, for example, the case where insertion is performed by bending. For example, when the tip clearance C is set to be large, the tip portion of the probe becomes flexible and likely to curve and, therefore, it becomes easy to insert into a narrow and sharply curved lumen.

Furthermore, by removing the pipe 581 for fixing from the cover 588, the sheath 38 and the sheath base can be removed as one unit from the pipe 581 for fixing and, therefore, the sheath 38 can be exchanged. Consequently, in the case where optical performances may be degraded during the use of the probe due to, for example, damage to the part of the inner surface•outer surface of the sheath 38 facing the prism 551, the optical performances can recover the original conditions by only exchanging one unit composed of the sheath 38 and the sheath base 582.

Since the metal ball 761 can be a target of X-ray photography of the tip, it is possible to detect precisely the tip position of the optical sheath 38 by taking a radiograph.

According to the aforementioned present embodiment, since the metal ball 761 embedded in the inner surface tip of the optical sheath 38 is in point contact with the tip surface of the tip housing 552, the rotation of the housing 552 can be stabilized without variations and, therefore, a proper OCT image can be produced. In addition, since even when the sheath lengths vary, the window 46, which is a light exit•entrance portion, can be brought close to the tip of the optical sheath 38 at a minimum clearance, operating ease for the operator during observation is improved.

By setting•keepng the tip clearance C to be large, it is easy to insert into a curved small diameter portion during insertion operation and, therefore, operating ease is improved.

In manufacture of the sheath, since it is not necessary to tightly control the precision of the length thereof, productivity is improved.

Even when the optical performances are degraded due to, for example, damage to the sheath, since a proper optical tomogram can be produced only by exchanging the sheath, outlay of the user can be reduced.

The housing 552 can be radiographed, while the optical sheath 38 portion forward thereof cannot be radiographed. However, the metal ball 761 provided at the optical sheath 38 tip can be radiographed, operating ease during insertion into a fine lumen organ under radioscopy is improved.

(Modified Example of the Second Embodiment)

Figure 14:
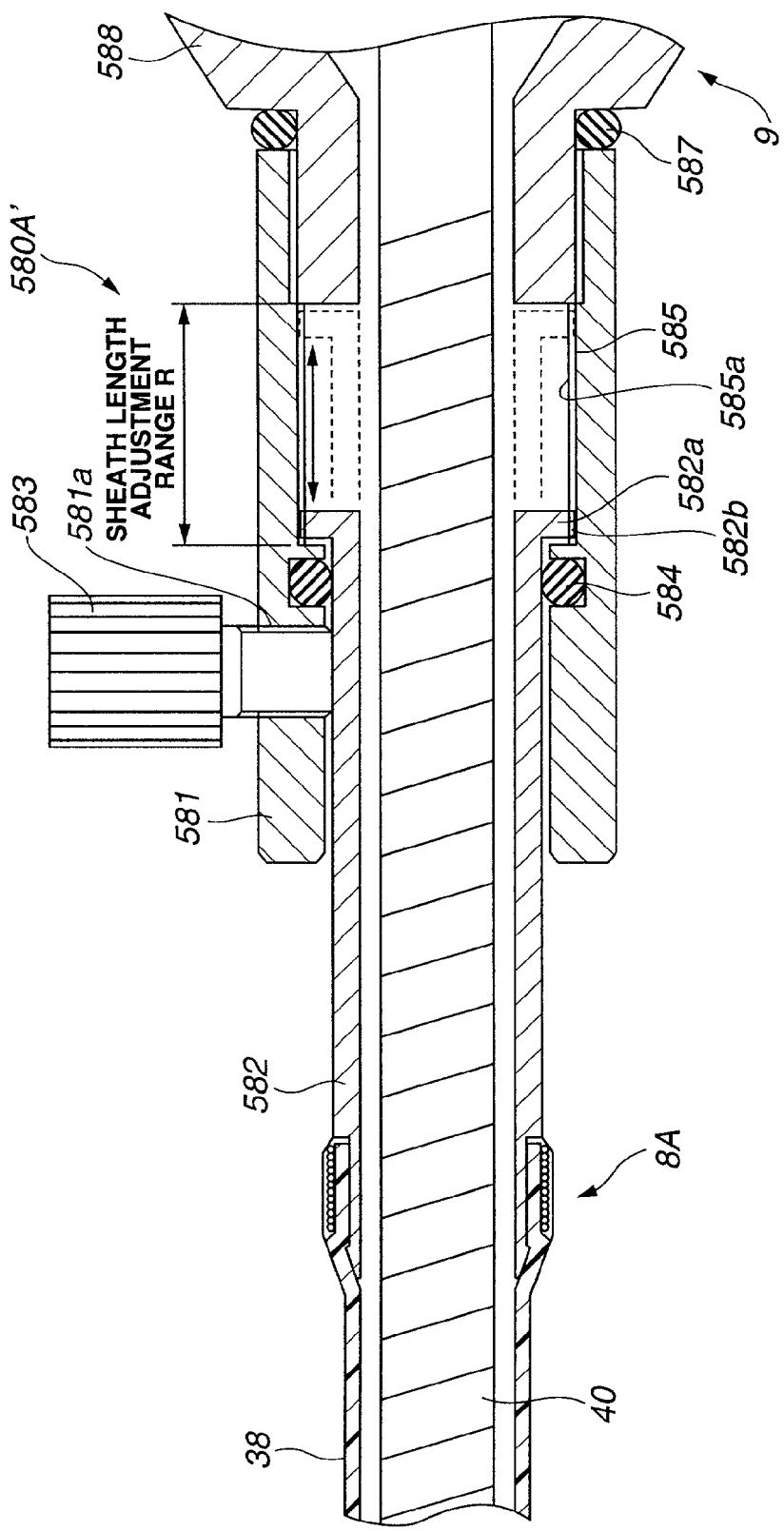

A modified example of the second embodiment according to the present invention will be described with reference to FIG. 14. FIG. 14 shows the configuration of a sheath length adjustment mechanism 580A' in the modified example of the second embodiment. Only the part different from that in the second embodiment will be described with reference to FIG. 14.

Regarding the sheath length adjustment mechanism 580A', an adjusting screw portion 585a is provided on the inner surface thereof in the longitudinal direction, and a flange screw portion 582b, which is a screw formed on the outer side surface of the flange 582a in order to engage with the aforementioned adjusting screw portion 585a, is provided. Other configuration is similar to that in the fourth embodiment.

According to such a configuration, the position of the flange screw portion 582b screwed relative to the adjusting screw portion 585a is changed by rotating the sheath base 582 about the axis in the longitudinal direction relative to the pipe 581 for fixing. Consequently, the sheath length can be adjusted by controlling the insertion length of the sheath base 582 into the pipe 581 for fixing, and actions similar to those in the second embodiment can be exhibited.

The present modified example has the following effects.

Effects similar to those in the second embodiment can be achieved and, in addition, since the length of the sheath can be adjusted finely by rotational motion of the screw, fine adjustment of the sheath length can be performed with ease and, therefore, operating ease is further improved.

Third Embodiment:

Regarding the third embodiment, only the part different from that in the second embodiment will be described with reference to FIG. 15 to FIG. 19.

Figure 15:
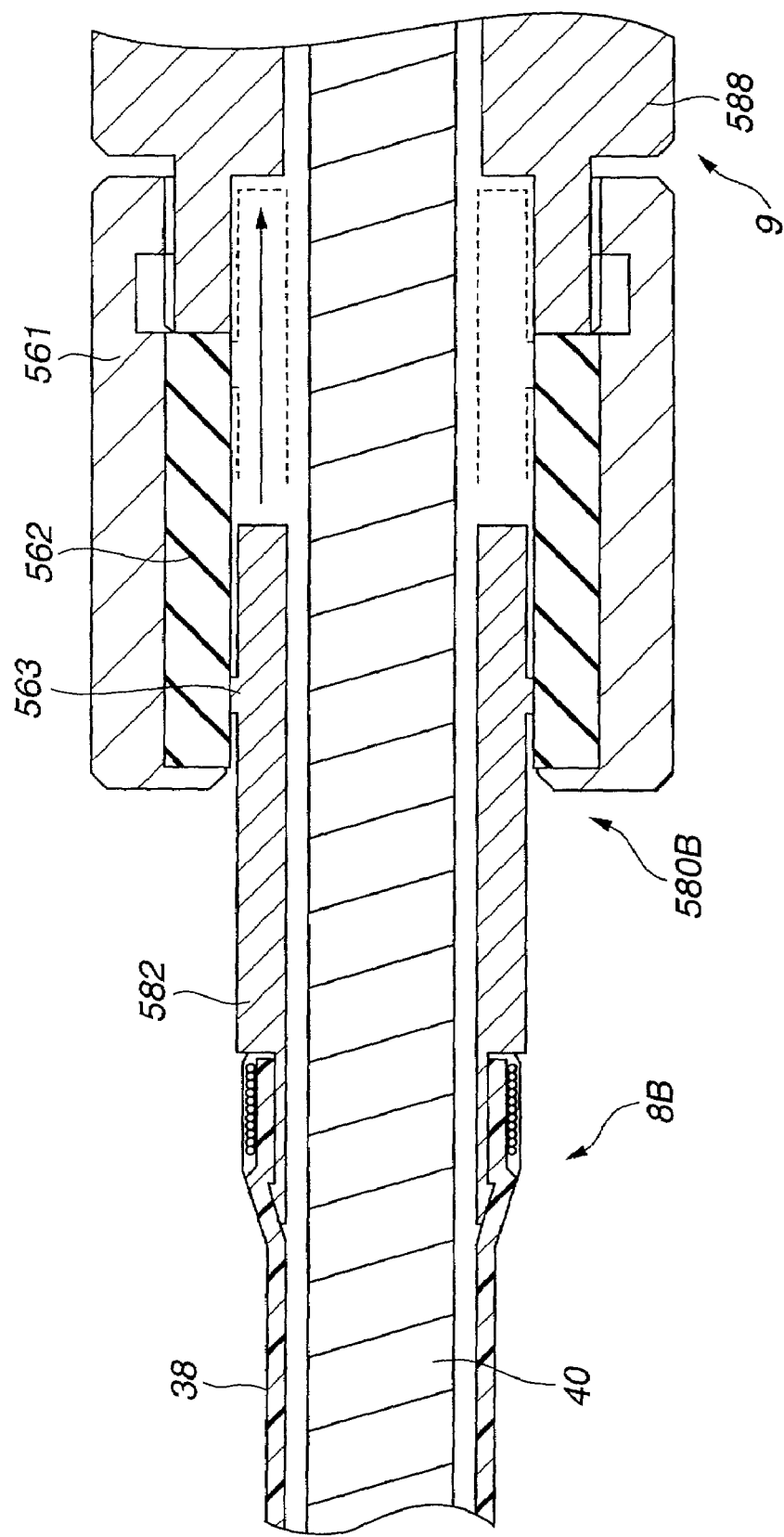
FIG. 15 to FIG. 19 relate to a third embodiment according to the present invention.

As shown in FIG. 15, a sheath retaining ring 561 is thread-engaged with the tip of a folding prevention cover 588. A ring rubber 562 is fitted on the inner perimeter surface of the sheath retaining ring 561.

On the other hand, the base end of a sheath 38 is fixed to a sheath base 582 with string winding and adhesion. A convex portion 563 is provided on the outer perimeter surface of the sheath base 582, and by tightening the sheath retaining ring 561, the ring rubber 562 is protruded toward the inner diameter side and is press-contacted and fixed to the convex portion 563 of the sheath base 582.

Under the condition that the sheath retaining ring 561 is loosened, the sheath base 582 can be moved along the inner perimeter of the ring rubber 562 in the direction of the axis thereof. The fixing position of the sheath base 582 can be changed (relative to the connector potion 9 side) from the position where the convex portion 563 is located at the front end of the inner perimeter surface of the ring rubber 562 to the neighborhood of the position where the convex portion 563 is located at the rear end of the inner perimeter surface of the ring rubber 562 and, therefore, a sheath length adjustment portion 580B is formed.

The sheath retaining ring 561 is loosened, and the sheath base 582 is inserted into the ring rubber 562. In a manner similar to that in the second embodiment, after the tip clearance C between the tip surface of the tip unit 39 in the sheath 38 and the sheath seal portion is set at a proper value, for example, a minimum value, the sheath retaining ring 561 is tightened.

When this sheath retaining ring 561 is tightened, the ring rubber 562 is applied with compression force from both the front end and the rear end and, therefore, is contracted in the direction of the axis and, at the same time, the inner diameter is reduced (is protruded toward the inside in the radius direction). Consequently, the sheath base 582 is tightened and fixed by a frictional force.

The convex portion 563 provided on the outer perimeter of the sheath base 582 especially serves a function of preventing the sheath 38 from pulling out due to an external force. When the sheath retaining ring 561 is loosened and the frictional force applied to the convex portion 563 is reduced, the sheath base 582 can be pulled out and, therefore, the sheath can be exchanged with ease. Furthermore, by the press contact of the front end surface of the folding prevention cover 588 at the rear end of this ring rubber 562 and the convex portion 563 of the sheath base 582, a function of making the inside a watertight structure is achieved.

Figure 16:
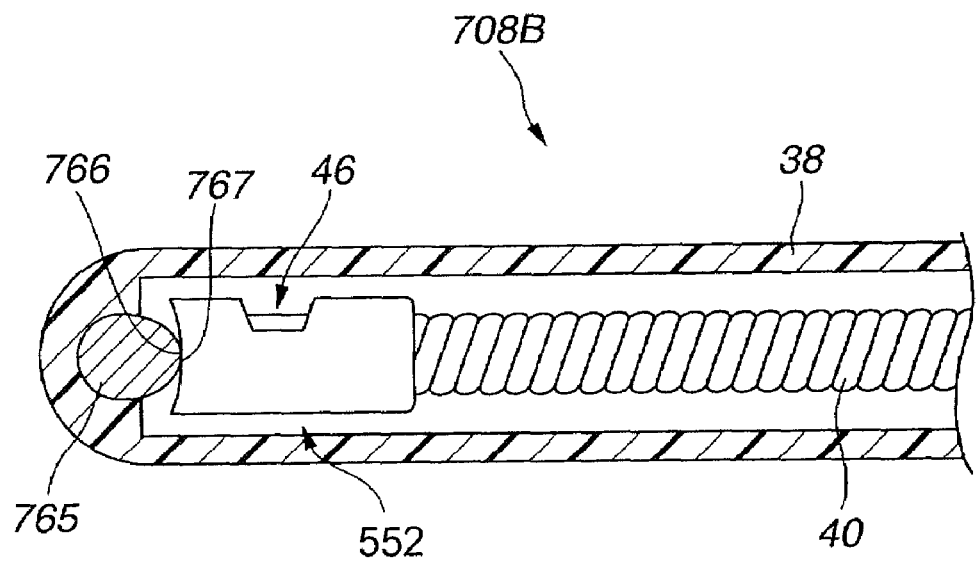

As shown in FIG. 16, regarding an optical probe 708B according to the present embodiment, a part of a friction prevention member 765 is embedded in the sheath at the inner surface tip of the optical sheath 38, and regarding this friction prevention member 765, the curved surface exposed in the optical sheath 38 is the convex portion 766. The tip surface of the housing 552 is made to be a concave portion 767.

The curvature radius of the convex portion 766 of the friction prevention member 765 is made smaller than the curvature radius of the concave portion 767 of the tip surface of the housing 552. Consequently, besides the actions similar to those in the first embodiment, the fitting of the concave and convex surfaces constitutes the bearing and, therefore, shake of the housing 552 during rotation can be reduced. Other configuration is similar to that in the second embodiment.

According to the aforementioned present embodiment, in addition to the effects described in the second embodiment, since the rotation axis of the housing 552 is further stabilized, the perimeter surface of the housing 552 can be reliably prevented from contacting with the inner surface of the optical sheath 38 and, therefore, a further proper OCT image can be produced. Since the sheath length can be easily adjusted•exchanged compared to that in the second embodiment, operating ease is improved.

Figure 17:
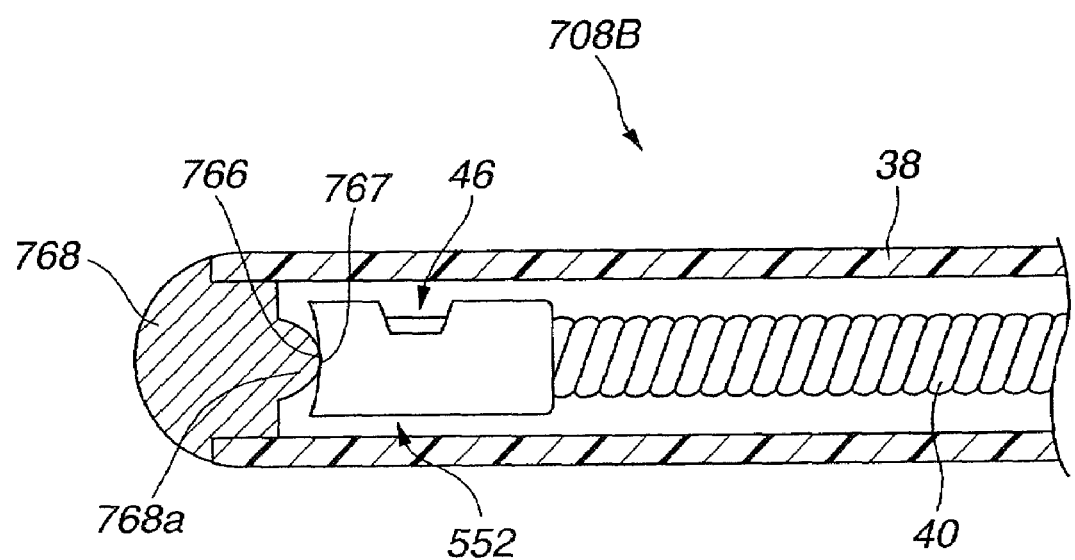

As a first modified example of the optical probe 708B, a convex surface 766 of the friction prevention member 765 may be integrally formed at a protuberance portion 768a of a seal cap 768 for sealing watertight the tip of the optical sheath 38, as shown in FIG. 17. By making the concave surface 767 at the tip surface of the housing 552 point-contact with the convex surface 766 on the seal cap 768, similar actions•effects can be achieved.

Figure 18:
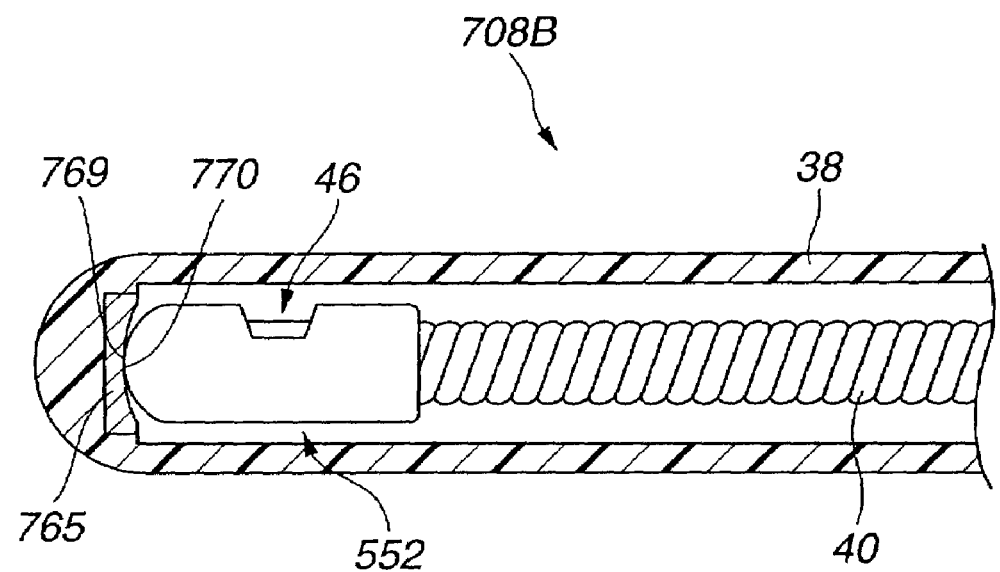

As a second modified example of the optical probe 708B, the configuration may includes the curved surface of the friction prevention member 765, a part of which is embedded in the inner surface tip of the optical sheath 38, exposed in the optical sheath 38 as a concave surface 769, and the tip surface of the housing 552 as a concave portion 770, wherein the curvature radius of the concave portion 769 of the friction prevention member 765 may be specified to be larger than the curvature radius of the convex surface 770 at the tip surface of the housing 552, as shown in FIG. 18. By making the concave surface 769 at the tip surface of the housing 552 point-contact with the convex surface 770 of the friction prevention member 765, similar actions•effects can be achieved.

Figure 19:
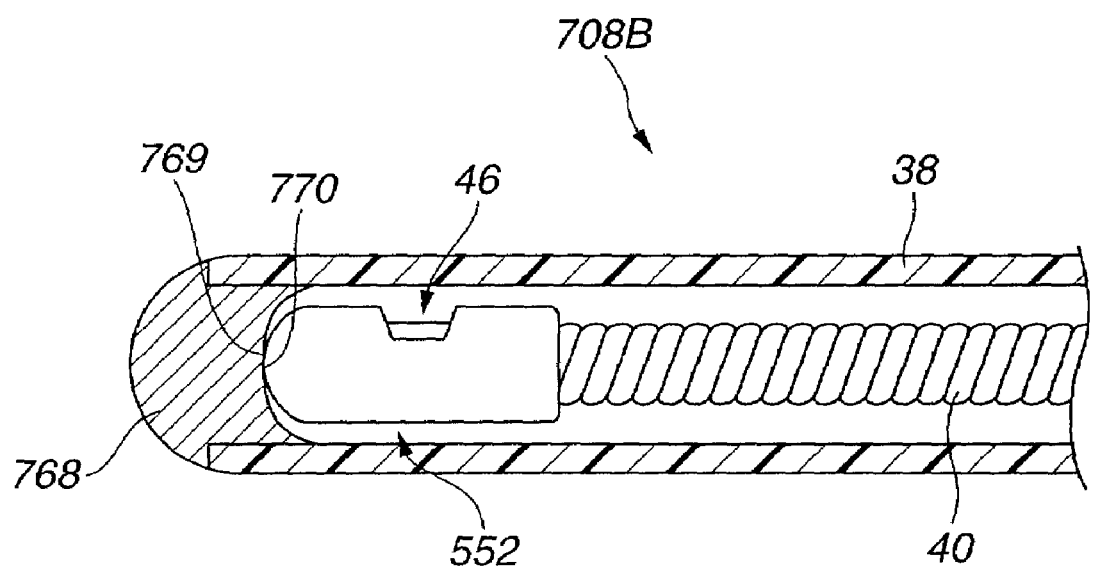

As a third modified example of the optical probe 708B, a concave surface 769 of the friction prevention member 765 may be integrally formed at the seal cap 768 for sealing watertight the tip of the optical sheath 38, as shown in FIG. 19. By making the concave surface 769 at the tip surface of the housing 552 point-contact with the convex surface 770 on the seal cap 768, similar actions•effects can be achieved.

Fourth Embodiment:

Since the present embodiment is nearly the same as the second embodiment, only different points will be described.

The fourth embodiment according to the present invention will be described below with reference to FIG. 20A, FIG. 20B, and FIG. 21. FIG. 20A and FIG. 20B show the configuration of a sheath length adjustment mechanism 580C of an optical probe 8C according to the fourth embodiment.

In the present embodiment, no sheath length adjustment mechanism is provided in the connector potion 9, a bellows portion 565 is provided, for example, in the neighborhood of the base end of the sheath 38 and, therefore, has a function as a sheath length adjustment mechanism 580C.

In the present embodiment, the length of the sheath 38 can be adjusted and kept by adjusting the length of the bellows portion 565.

Figure 21:
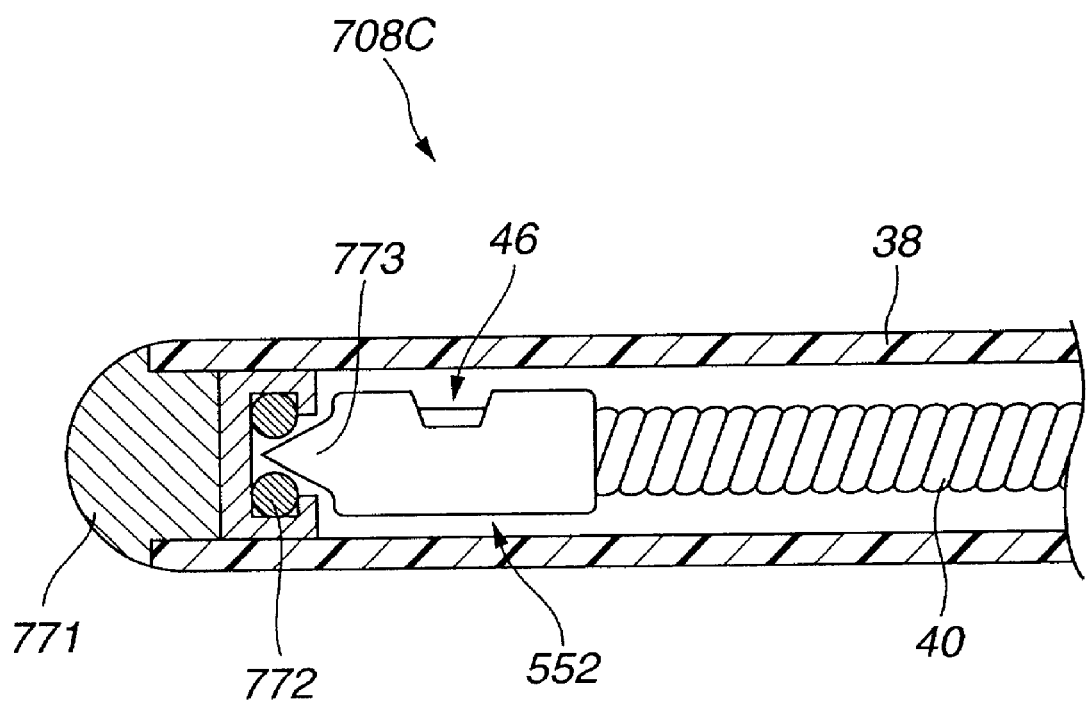

As shown in FIG. 21, regarding the configuration of the optical probe 708C according to the present embodiment, angular contact ball bearings 772 are provided on the optical sheath 38 inner surface side of a tip cap 771 for sealing watertight the tip of the optical sheath 38, and a convex portion 773 is provided at the tip surface of the housing 552. Other configuration is similar to that in the second embodiment.

According to such a configuration, since rotation is performed while the outer perimeter surface is in point contact with each of the angular contact ball bearings 772, the convex portion 773 at the tip surface of the housing 552 is applied with further reduced friction, rotation is stabilized, variations in rotation are reduced and, therefore, a further proper OCT image can be produced.

According to the aforementioned present embodiment, in addition to the effects described in the second embodiment, since the rotation axis of the housing 552 is further stabilized, the perimeter surface of the housing 552 can be reliably prevented from contacting with the inner surface of the optical sheath 38 and, therefore, a further proper OCT image can be produced.

Effects similar to those in the second embodiment are achieved and, in addition, since adjustment of the sheath length is simplified compared to those in the second and third embodiments, operating ease is improved.

Since no new mechanical design is required for the connector potion 9, conventional components can be diverted and, therefore, productivity is improved.

Fifth Embodiment:

Since the present embodiment is nearly the same as the second embodiment, only the part different from that of the second embodiment will be described.

Figure 22:
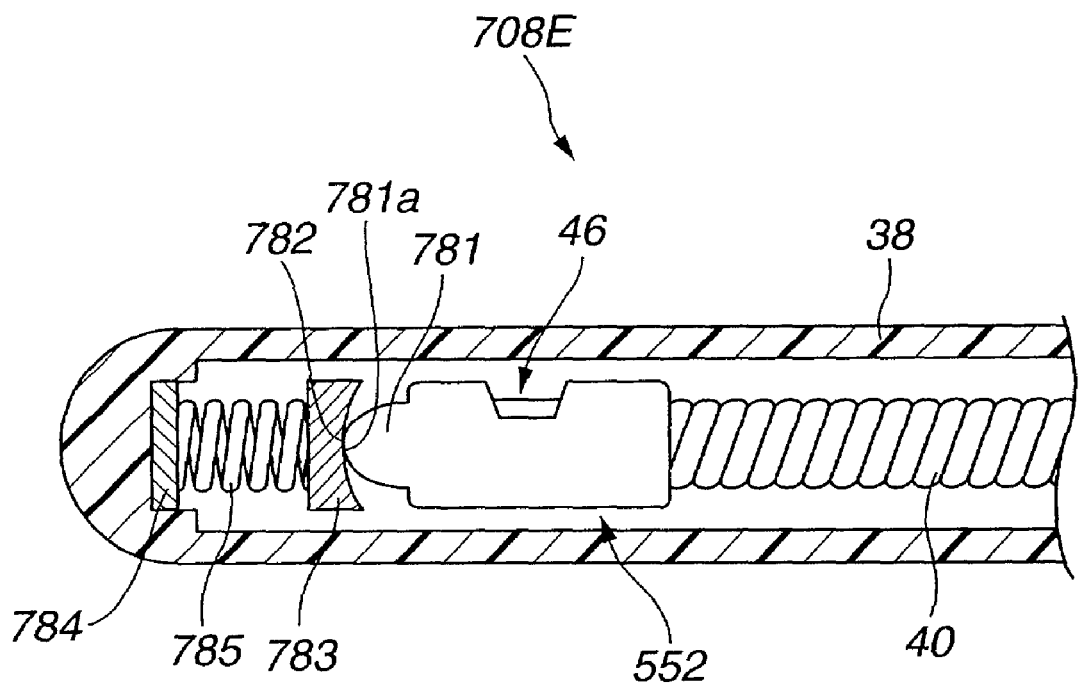
FIG. 22 to FIG. 28 relate to a fifth embodiment according to the present invention.

As shown in FIG. 22, the configuration of an optical probe 708E according to the present embodiment includes a bearing portion 783 which is in contact with a convex surface 781a of a tip portion 781 provided at the tip surface of the housing 552 and which has a concave surface 782 to become a bearing of the convex surface 781a of the tip portion 781 during rotation, an elastic body holding portion 784 embedded in the tip inner surface of the sheath 38, and a spring 785 which is an elastic body for joining the elastic body holding portion 784 and the bearing portion 783. Other configuration is similar to that in a thirteenth embodiment.

In the present embodiment, since the convex surface 781a of the tip portion 781 and the concave portion 782 of the bearing portion 783 are made to be in contact with each other at a constant pressure by the spring 785, the shake during rotation can be further reduced.

Figure 23:
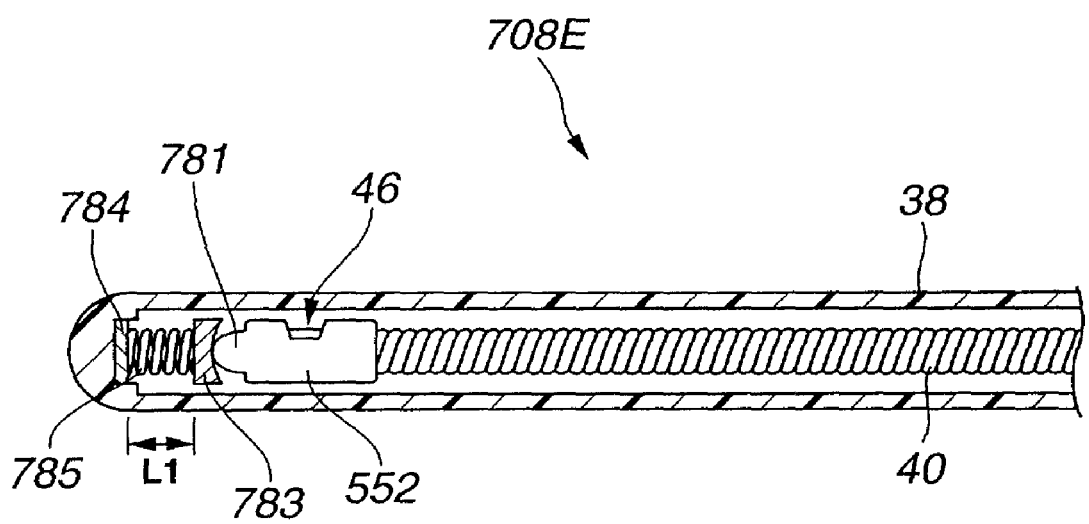
Figure 24:
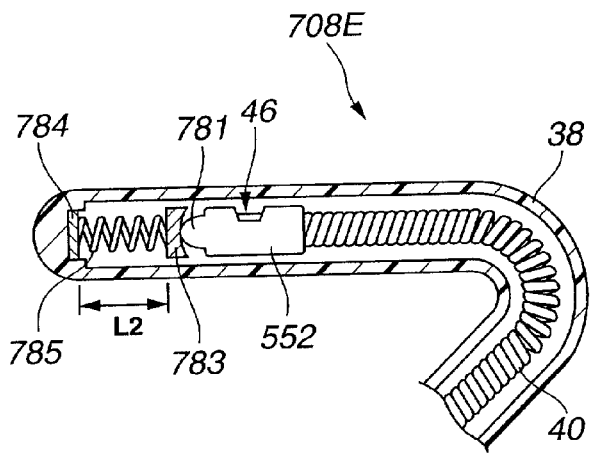

In the optical probe 708E, regarding the distance L1, shown in FIG. 23, between the elastic body holding portion 784 and the housing 552 in the longitudinal axis direction during no curving and the distance L2, shown in FIG. 24, between the elastic body holding portion 784 and the housing 552 in the longitudinal axis direction during curving generally fall into L1<L2 because of difference in elasticity between the flexible shaft 40 and the sheath 38 and, therefore, the housing 552 is moved farther from the tip of the optical sheath 38 in the longitudinal axis direction by a small degree. However, even in such a case, since (the concave surface 782 of) the bearing portion 783 is in contact with the convex surface 781a at the tip portion 781 of the housing 552 due to the elasticity of the spring 785, the shake during rotation can be reduced.

According to the aforementioned present embodiment, in addition to the effects described in the second embodiment, since the rotation axis of the housing 552 is further stabilized, the shake and variations in rotation of the housing 552 are reduced and, therefore, a further proper OCT image can be produced.

When the optical probe 708E is curved, since (the concave surface 782 of) the bearing portion 783 is in contact with the tip convex surface 781 of the housing 552 due to the elasticity of the spring 785, the rotation axis can be maintained, the shake during rotation can be reduced and, therefore, a proper OCT image can be produced.

Figure 25:
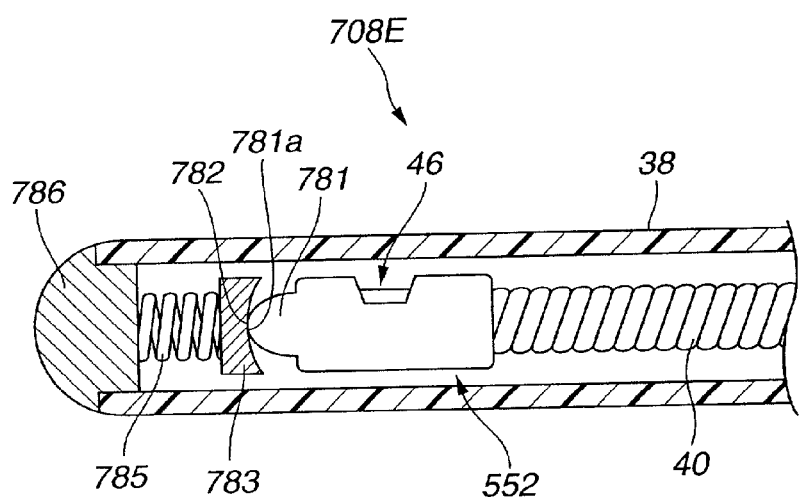

As a first modified example of the optical probe 708E, in the configuration, the spring 785 may be held at the seal cap 786 for sealing watertight the tip of the optical sheath 38, as shown in FIG. 25. By making (the concave surface 782 of) the bearing portion 783 point-contact with the tip convex surface 781 of the housing 552 due to the elasticity of the spring 785, similar actions•effects can be achieved.

Figure 26:
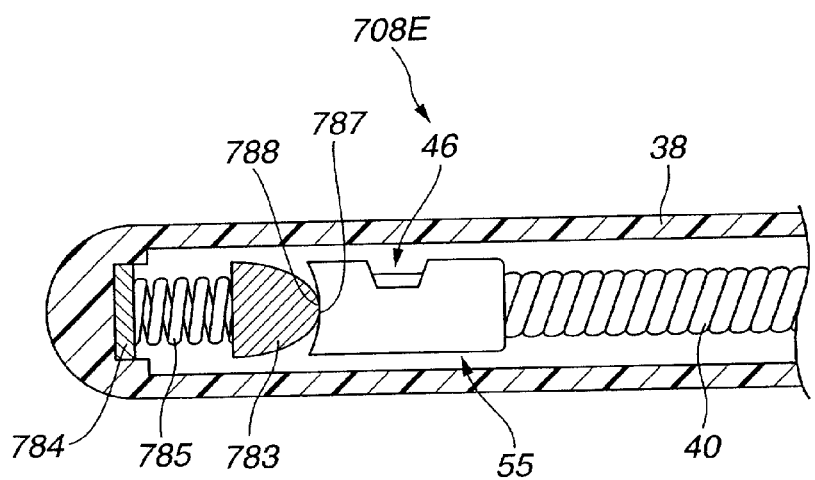

As a second modified example of the optical probe 708E, in the configuration, a tip concave surface 787 may be provided at the tip surface of the housing 552, and a convex surface 788 to be point-contacted with the tip concave surface 787 of the housing 552 may be provided on the bearing portion, 783, as shown in FIG. 26. By making (the convex surface 788 of) the bearing portion 783 point-contact with the tip concave surface 787 of the housing 552 due to the elasticity of the spring 785, similar actions•effects can be achieved.

Figure 27:
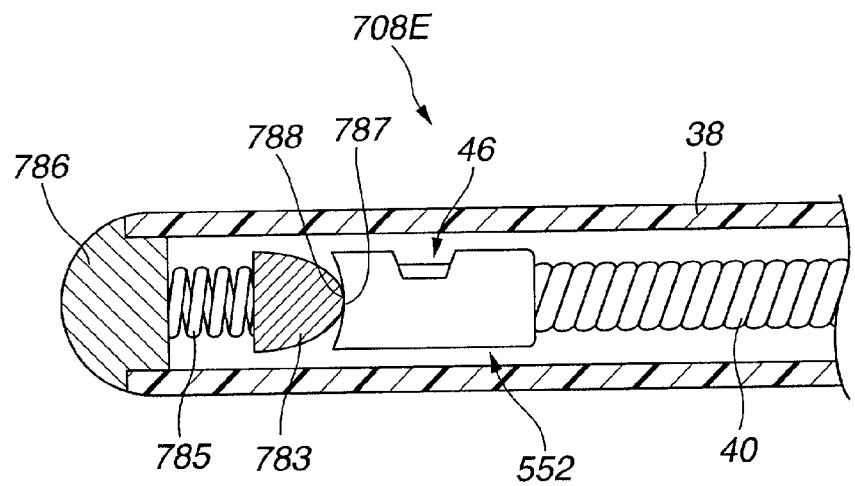

As a third modified example of the optical probe 708E, in the configuration, the spring 785 may be held at the seal cap 786 for sealing watertight the tip of the optical sheath 38, and in a manner similar to that in the second modified example, the tip concave surface 787 may be provided at the tip surface of the housing 552, and a convex surface 788 to be point-contacted with the tip concave surface 787 of the housing 552 may be provided on the bearing portion 783, as shown in FIG. 27. By making (the convex surface 788 of) the bearing portion 783 point-contact with the tip concave surface 787 of the housing 552 due to the elasticity of the spring 785, similar actions•effects can be achieved.

Figure 28:
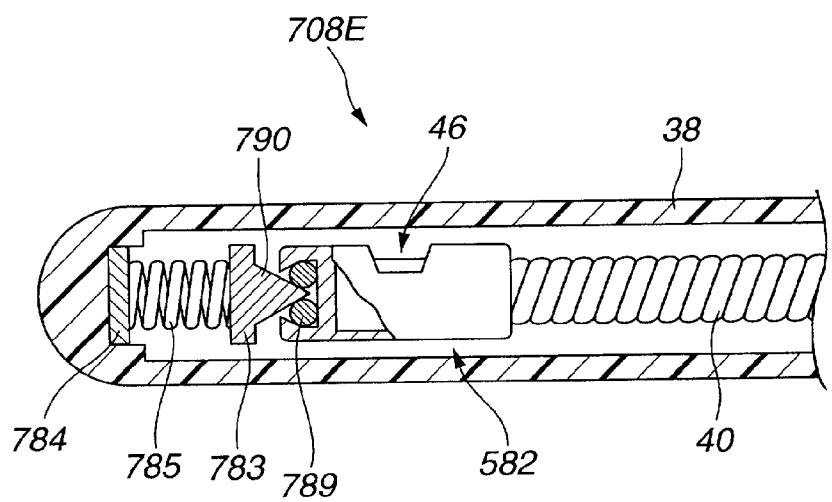

As a fourth modified example of the optical probe 708E, in the configuration, angular contact ball bearings 789 may be provided at the tip surface of the housing 552 and, in addition, a convex surface 790 may be provided on the bearing portion 783 in order that the outer perimeter surface of the convex portion 790 is contacted with each of the angular contact ball bearings 789, as shown in FIG. 28. By making (the outer perimeter surface of the convex surface 790) the bearing portion 783 point-contact with each of the angular contact ball bearings 789 due to the elasticity of the spring 785, similar actions•effects can be achieved.

As a fourth modified example of the optical probe 708E, in the configuration, angular contact ball bearings 789 may be provided at the tip surface of the housing 552 and, in addition, a convex surface 790 may be provided on the bearing portion 783 in order that the outer perimeter surface of the convex portion 790 is contacted with each of the angular contact ball bearings 789, as shown in FIG. 28. By making (the outer perimeter surface of the convex surface 790) the bearing portion 783 point-contact with each of the angular contact ball bearings 788 due to the elasticity of the spring 785, similar actions•effects can be achieved.

Sixth Embodiment:

Since the present embodiment is nearly the same as the second embodiment, only the part different from that of the second embodiment will be described.

Figure 29:
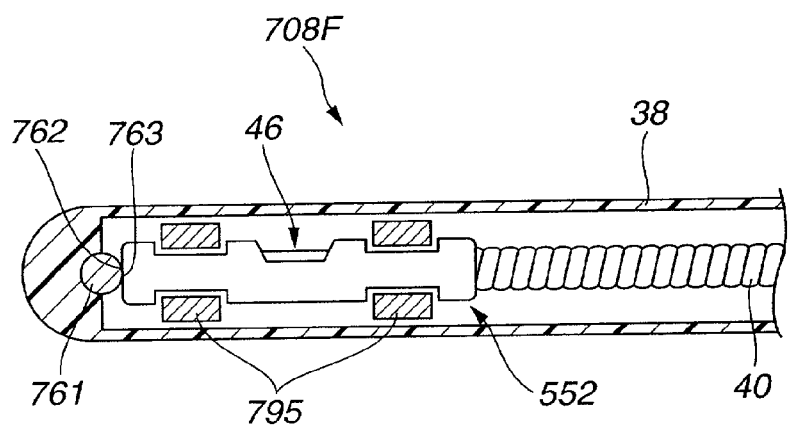
FIG. 29 and FIG. 30 relate to a sixth embodiment according to the present invention.

As shown in FIG. 29, in the configuration of an optical probe 708F according to the present embodiment, bearings 795 are provided on both the tip side and the rear end side of the housing 552 in the condition that they are not fixed. Other configuration is similar to that in the thirteenth embodiment.

Regarding the present embodiment, in addition to the effects in the second embodiment, the rotation of the housing 552 becomes smooth by the bearings 795 and, therefore, jounce can be prevented. Furthermore, contact of the housing 552 and the optical sheath 38 is prevented by the bearings 795 and, therefore, damaging or breakage of the inner surface of the optical sheath 38 can be prevented.

Figure 30:
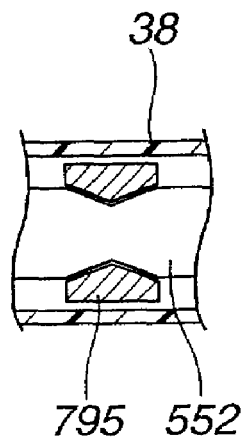

The bearing 795 may have the shape as shown in FIG. 30. By having such a shape, friction can be further prevented and, in addition, the axis position can be stabilized.

Seventh Embodiment:

Regarding the conventional configuration of the optical probe, in the case where a liquid, for example, for refractive index matching, has been put into the optical sheath 38, when a bubble has adhered to the light exit•entrance surface, it has been difficult to remove and, therefore, there has been a disadvantage in that it has not been possible to produce a proper OCT image.

Accordingly, regarding the optical probe in which a liquid has been put into the optical sheath, an optical probe, in which a bubble generated on the light exit•entrance surface can be removed with ease and which can produce a proper OCT image, will be described.

Since the present embodiment is nearly the same as the second embodiment, only the part different from that in the second embodiment will be described.

Figure 31:
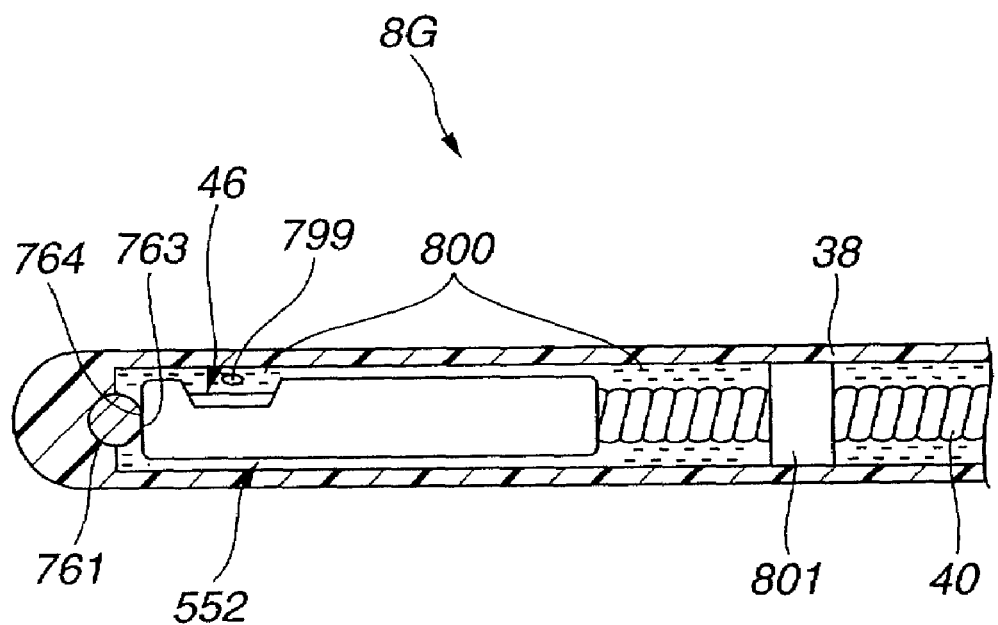
FIG. 31 to FIG. 42 relate to a seventh embodiment according to the present invention.

As shown in FIG. 31, in the configuration of an optical probe 708G according to the present embodiment, the optical sheath 38 is filled with a liquid 800 for refractive index matching, a bubble trap 801 made of stainless steel is provided as a bubble passage limitation unit on the outer perimeter of the flexible shaft 40. The fixing position of the bubble trap is set at the position, for example, on the order of 5 mm away from the side end portion of the flexible shaft 40 of the housing 552, and the width is set to be on the order of 1 mm.

Figure 32:
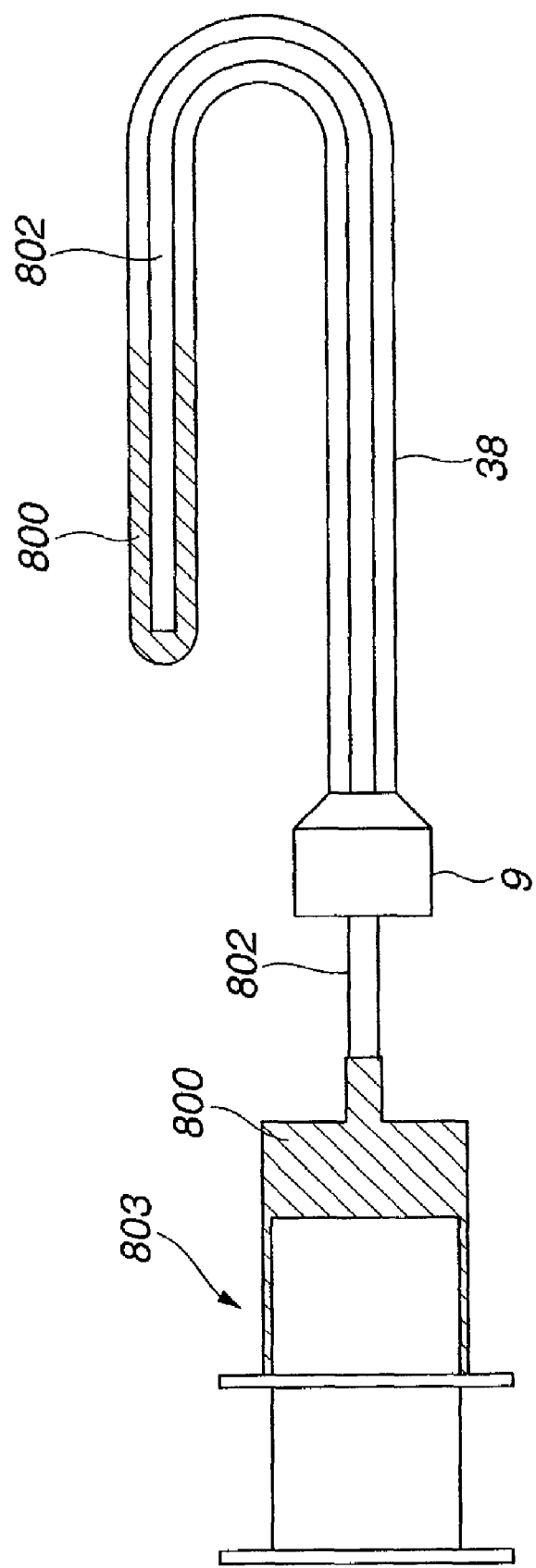

Herein, injection of the liquid 800 for refractive index matching into the optical sheath 38 will be described. As shown in FIG. 32, a tube 802 for filling is inserted into the optical sheath 38. The tube 802 for filling is inserted until the tip thereof contacts with the inside of the optical sheath 38 tip. Subsequently, a refractive index matching medium 800, for example, water, is gradually put into the optical sheath 38 with a syringe 803 through the tube 802 for filling. At this time, air is purged from the gap between the tube 802 for filling and the optical sheath 38, and the liquid 800 is accumulated from the inside tip of the optical sheath 38. Consequently, regarding even a highly viscous liquid such as water, air does not remain in the optical sheath 38. After the tube 802 for filling is pulled out, a probe assembly composed of the housing 552, flexible shaft 40, etc. may be inserted until the tip. When the refractive index matching medium 800 is removed, suction may be performed with the tube 802 for filling.

Figure 33:

Regarding the bubble trap 801, as shown in FIG. 33, a circular tube-shaped stainless steel is formed into the shape of a letter C, and is fitted to the outer perimeter of the flexible shaft 40. Metals other than stainless steel, plastics, silicone rubbers, heat-shrinkable tubes, etc., may be used as the material thereof. Other configuration is similar to that in the second embodiment.

Figure 34:
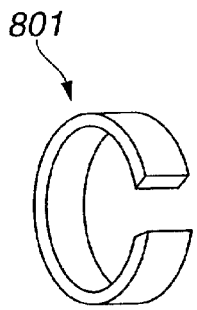
Figure 35:
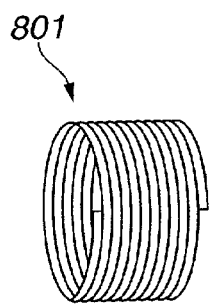
Figure 36:
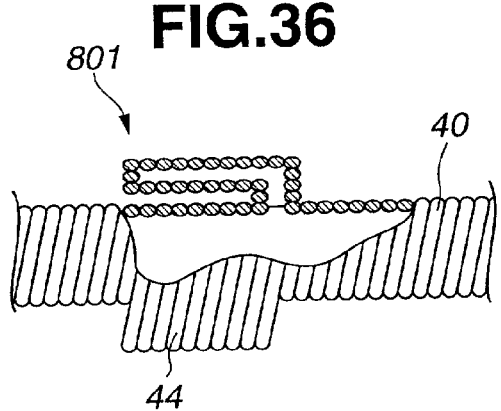

The bubble trap 801 may be configured by forming a flat-shaped stainless steel into the shape of a letter C as shown in FIG. 34, or be configured by forming a circular tube-shaped stainless steel into the shape of a coil as shown in FIG. 35. Furthermore, the bubble trap 801 may be formed by multiplex winding of a coil 44 constituting the flexible shaft 40 at a predetermined position as shown in FIG. 36.

Figure 37:
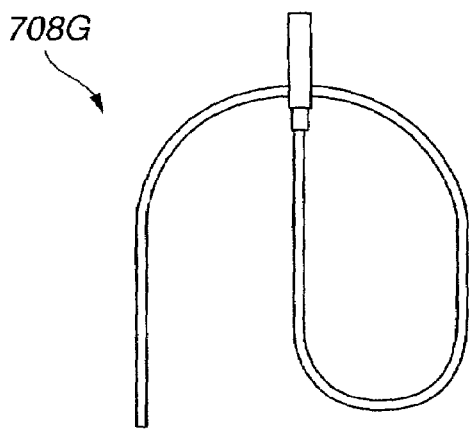
Figure 38:
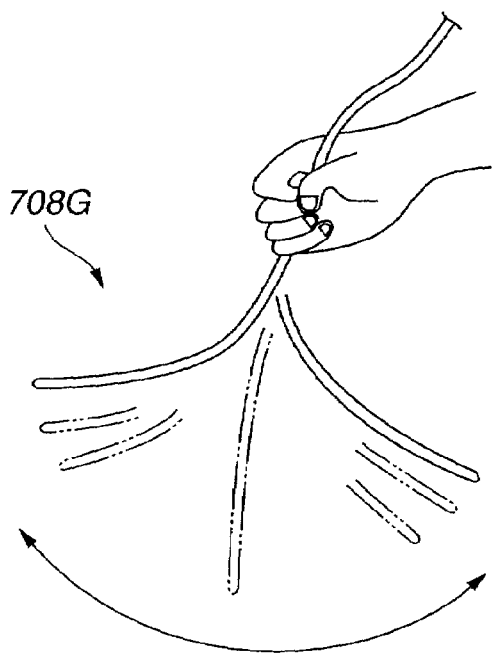

In the present embodiment, when a bubble 799 is generated between the window portion 46 of the housing 552 and the optical sheath 38 (refer to FIG. 31), as shown in FIG. 37, the tip portion of the optical probe 708G is made to point downward and is stood for some time. Thereafter, as shown in FIG. 38, the optical probe 708G is grasped at the position on the order of 15 cm apart from the tip side, and is shaken from side to side by a large amount. Consequently, the bubble 799 generated between the window portion 46 of the housing 552 and the optical sheath 38 is broken finely, and is moved to the bubble trap 801 side due to action of centrifugal force because the specific gravity is smaller than that of the refractive index matching medium 800. Furthermore, the finely broken bubbles 799 move to the side at hand of the optical probe 708G through the gap between the bubble trap 801 and the optical sheath 38. The finely broken bubbles 799 moved to the side at hand of the optical probe 708G coalesce again. However, the coalesced bubbles cannot pass through the gap between the bubble trap 801 and the optical sheath 38 again because of surface tension and, therefore, movement to the tip side of the optical probe 708G is prevented.

According to the aforementioned present embodiment, in addition to the effects described in the second embodiment, since the bubble 799 generated between the window portion 46 of the light exit•entrance surface and the optical sheath 38 can be removed with ease and, furthermore, movement of the removed bubble 799 to the tip side of the optical probe 708G is prevented by the bubble trap 801, a proper OCT image can be produced.

Figure 39:
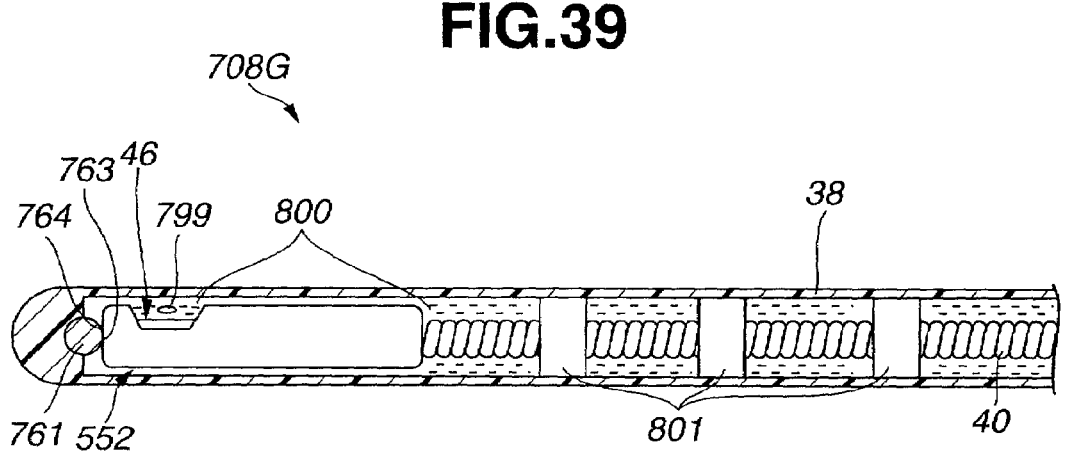

As shown in FIG. 39, in the configuration, a plurality of bubble traps 801 may be provided on the outer perimeter of the flexible shaft 40 at a predetermined interval, and the inside of the optical sheath 38 to be filled with the liquid 800 for refractive index matching may be divided into a plurality of partitions.

According to such a configuration, the bubbles generated between the optical sheath 38 and the flexible shaft 40 are trapped on a partition between a plurality of bubble traps 801 basis.

Consequently, the bubble 799 generated at the rear end of the probe is unlikely to enter the tip side of the probe. Since the bubble trap 801 serves as a slip ring, rotation and movement of the flexible shaft 40 becomes smooth and, in addition, insertion of the housing 552 and flexible shaft 40 into the optical sheath 38 becomes smooth. Since movement of the housing 552 and flexible shaft 40 in the optical sheath 38 becomes easy, linear scan and spiral scan become possible.

Figure 40:
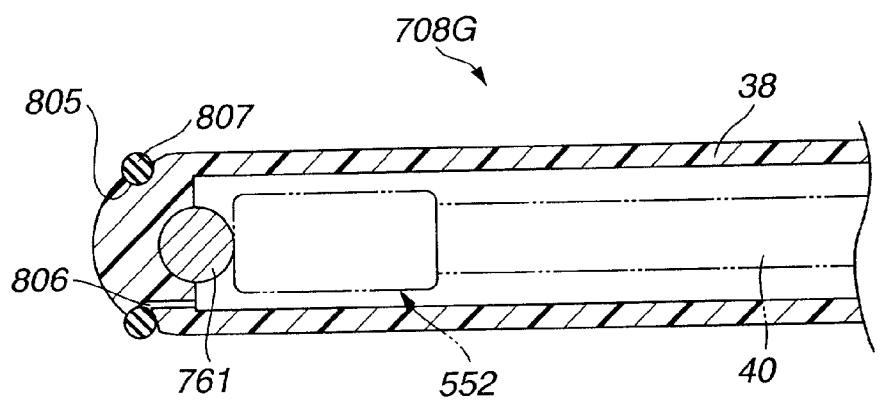
Figure 41:
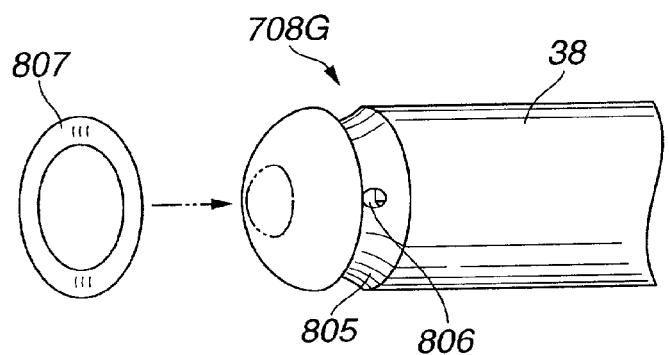

It has been described that injection of the liquid 800 for refractive index matching into the optical sheath 38 has been performed by the method as shown in FIG. 32. However, not limited to this, for example, a concave groove 805 is provided on the optical sheath 38 tip portion in the circumferential direction as shown in FIG. 40, and a communication path 806 communicating the inside and outside of the optical sheath 38 is formed as shown in FIG. 41. An elastic ring 807 is fitted into the concave groove 805.

Figure 42:
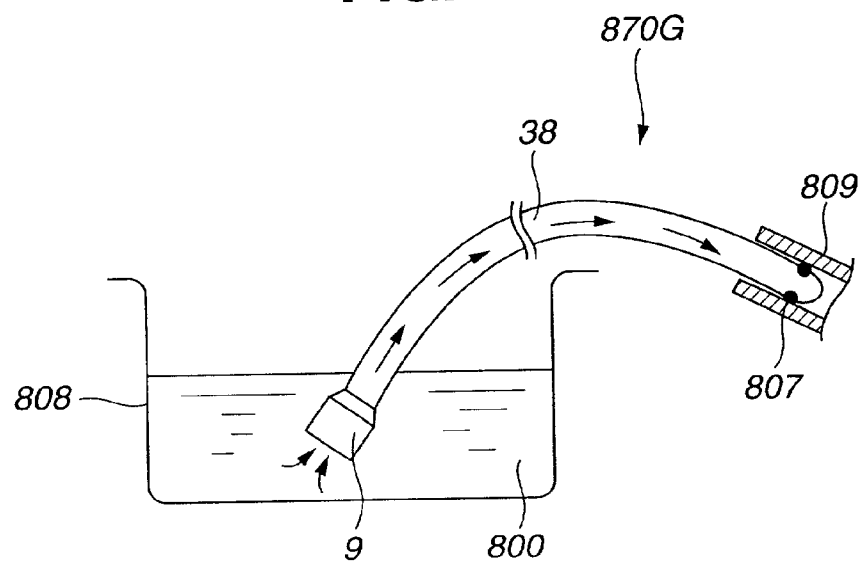

Subsequently, as shown in FIG. 42, the connection portion 9 at the rear end portion of the optical sheath 38 is entered into a container 808 filled with the refractive index matching medium 800, a suction base 809 of a vacuum suction device (not shown in the drawing) is connected to the tip portion of the optical sheath 38. The outside of the optical sheath 38 tip is made to have a negative pressure by the vacuum suction device. Consequently, the diameter of the elastic ring is enlarged, communication path 806 is opened and, therefore, the refractive index matching medium 800 is put in with no remaining bubble. After the refractive index matching medium 800 is put into, the probe assembly composed of the housing 552, flexible shaft 40, etc., may be inserted until the tip of the optical sheath 38.

When the elastic ring 807 is removed, or the tip portion of the optical sheath 38 is applied with a negative pressure as described above in the condition that the rear end portion of the optical sheath 38 is opened in air, the refractive index matching medium 800 can be removed with ease.

Eighth Embodiment:

Regarding the conventional optical probe, since the coil constituting the flexible shaft has been a simplex winding over the whole length, a follow-up property with respect to rotation and back-and-forth motion has been poor, and variations have occurred in motions. Consequently, there has been a disadvantage in that a proper OCT image has not been produced. Furthermore, change in the length of the flexible shaft has been large during bending and, therefore, (since a large clearance of the sheath tip has been required) operating ease has been degraded.

In the present embodiment, an optical probe which has an excellent follow-up property with respect to rotation•back-and-forth motion transferred to the tip portion and which can produce a proper OCT image will be described.

Since the present embodiment is nearly the same as the second embodiment, only the part different from that in the second embodiment will be described.

Figure 43:
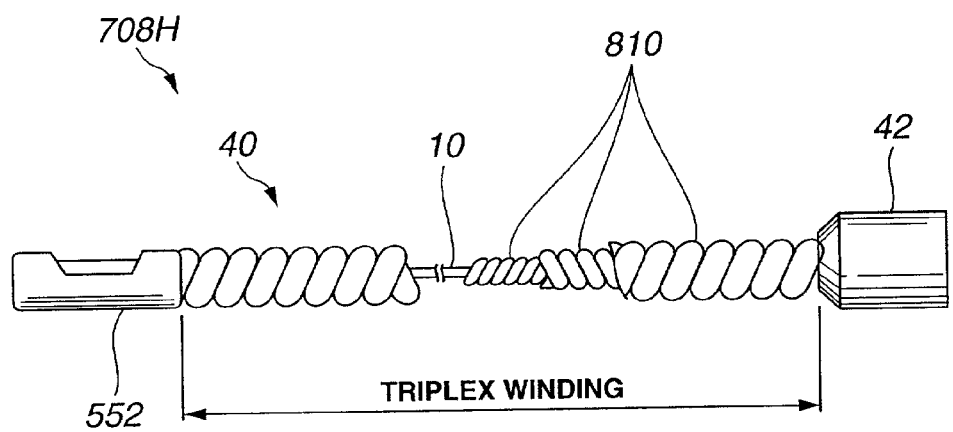
FIG. 43 to FIG. 47 relate to an eighth embodiment according to the present invention.

As shown in FIG. 43, a flexible shaft 40 of an optical probe 708H according to the present embodiment is configured by triply winding a coil 810 while the direction of winding is changed alternately. Other configuration is similar to that in the second embodiment.

Figure 44:
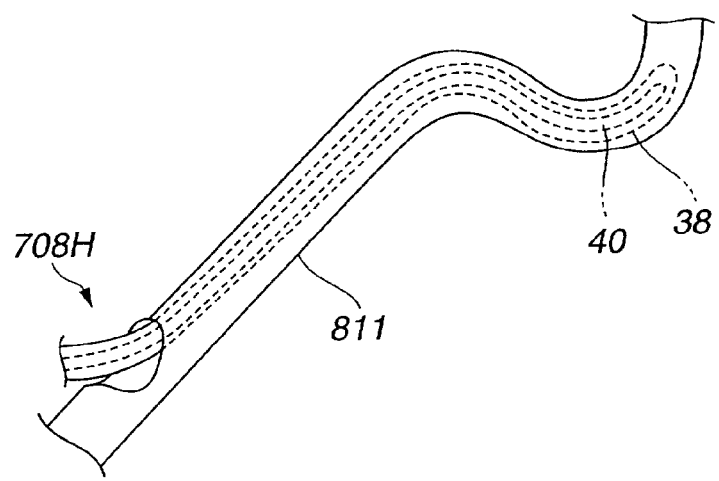

According to the present embodiment, in addition to the effects described in the second embodiment, as shown in FIG. 44, even when the inside of a curved lumen organ 811 is observed, the rotation•back-and-forth motion is transferred to the tip portion with excellent follow-up property by the flexible shaft 40 in which the coil 810 has been triply wound alternately. In addition, variations in the whole length of the flexible shaft 40 due to curve is reduced.

Accordingly, since the follow-up property with respect to rotation•back-and-forth motion of the probe tip is excellent, there is no variation in motion and, therefore, a proper OCT image can be produced. Since expansion and contraction are reduced, the optical fiber can be protected.

Figure 45:
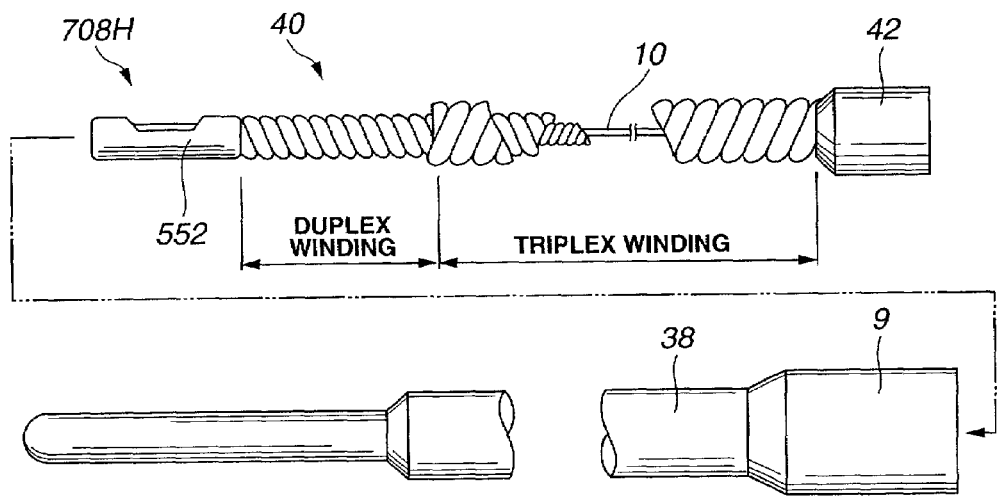

It has been described that the flexible shaft 40 has been configured by triply winding the coil 810 while the direction of winding has been changed alternately. However, as a first modified example, in the configuration, the coil 810 of the flexible shaft 40 may be a duplex winding in the neighborhood of the tip portion, be a triplex winding on the base end side, and the diameter of the housing 552 may be matched with the duplex winding, as shown in FIG. 45.

The small diameter portion of duplex winding is minimized in accordance with the requirement of the part into which insertion is performed. At this time, the diameter of the optical sheath 38 is made into the shape in which the tip side is small as well.

As described above, the tip portion has a small diameter and reduced rigidity, the rear end portion has a large diameter and can maintain rigidity. Consequently, the follow-up property with respect to rotation•back-and-forth motion can be ensured.

Figure 46:
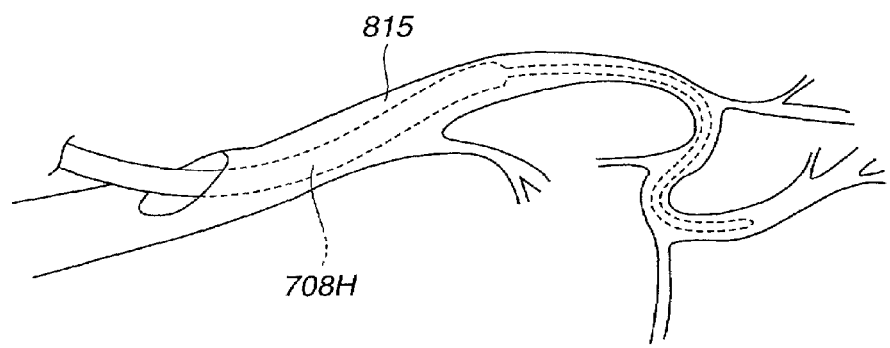

That is, since the tip portion is thin and the tip portion has reduced rigidity, it is possible to deform freely in blood vessels having many curved portions and, therefore, as shown in FIG. 46, the optical probe 708H can be inserted into coronary arteries, blood vessels in the deep recesses of body, and narrow lumen organs 815, for example, bile duct and pancreatic duct. Since rigidity is maintained in the rear end portion, undesirable deformation does not occur and, therefore, operation is performed with ease. In addition, since the small diameter portion is minimized, follow-up property is excellent and a further proper OCT image can be produced.

Figure 47:
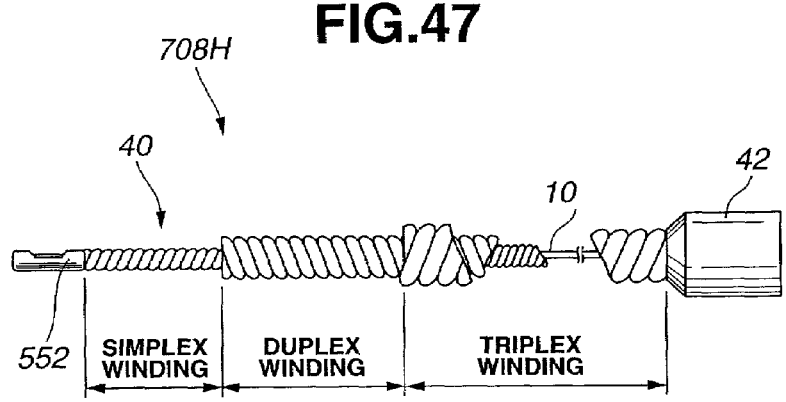

It has been described that the flexible shaft 40 has been configured by triply winding the coil 810 while the direction of winding has been changed alternately. However, as a second modified example, in the configuration, the coil 810 of the flexible shaft 40 may be a simplex winding, duplex winding, and triplex winding in that order, the nearest one to the tip portion first, the small diameter portions of simplex and duplex windings are minimized in accordance with the requirement of the part into which insertion is performed, and the diameter of the housing 552 may be matched with the simplex winding, as shown in FIG. 47.

As described above, the tip portion has a further reduced diameter and reduced rigidity. Therefore, since the tip portion is thinner, it is possible to insert into blood vessels, narrow lumen organs, etc., on further peripheral side in the body.

Ninth Embodiment:

Regarding the conventional optical probe, there has been an disadvantage in that when the tip portion has been curved, a perfect circle of the sheath cross section has not been maintained, friction has been increased because the rotor and the sheath have been contacted with each other, variations in rotation have occurred and, therefore, a proper OCT image has not been produced.

In the present embodiment, an optical probe, in which even when the tip portion is curved, the tip portion rotor is rotated smoothly in the optical sheath lumen and, therefore, a proper OCT image can be produced, will be described.

Although the present embodiment can be configured in a manner similar to that in the second embodiment, description will be made based on the configuration example of the second modified example of the optical probe 708B according to the third embodiment. That is, the present embodiment has the same basic configuration as the second embodiment and, therefore, can be applied to other embodiments having other configurations. Since the present embodiment is nearly the same as the second modified example of the optical probe 708B according to the third embodiment, only the part different from that in the second modified example of the optical probe 708B according to the third embodiment will be described.

Figure 48:
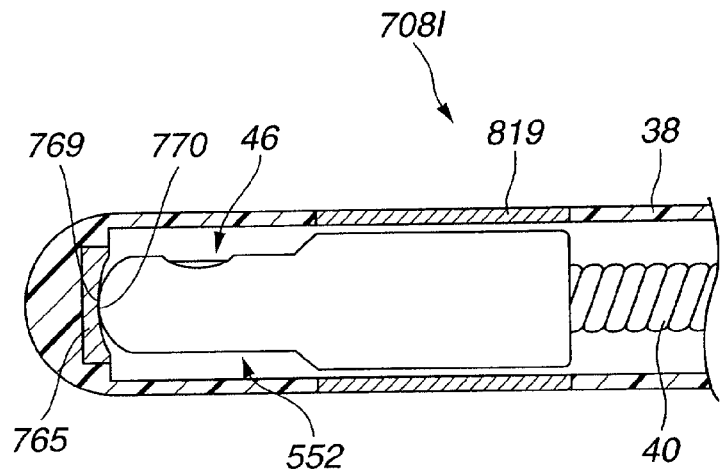
FIG. 48 to FIG. 50 relate to a ninth embodiment according to the present invention.
Figure 49:
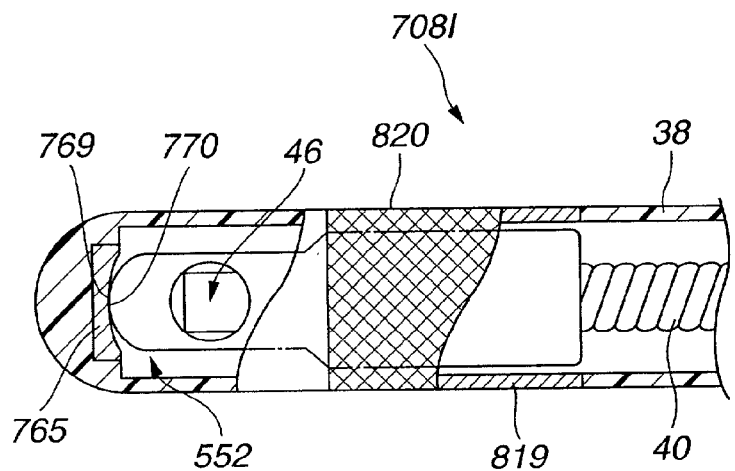

As shown in FIG. 48 and FIG. 49, in an optical probe 708I according to the present embodiment, a contact portion 819, at which the housing 552 is contacted with the sheath 38 inner wall, is applied with a mesh and, therefore, a stainless steel mesh ring 820 is provided. This mesh ring 820 is provided on the contact portion 819 by adhesion or welding, and is provided in a region other than the region (window portion 46) from which the observation beam exits in order that the observation beam is not hindered. Other configuration is the same as that in the second modified example of the optical probe 708B according to the third embodiment.

When the optical probe 708I is used while being inserted into a body cavity, even if the use is in the condition that the tip portion is bended, the perfect circle of the part provided with the mesh ring 820 is maintained and, therefore, the contact portion of the housing 552 and the optical sheath 38 lumen can be rotated smoothly. Since the mesh ring 820 is limitedly provided on the contact portion of the housing 552 and the optical sheath 38 lumen, the flexibility of the whole optical probe 708I is not degraded.

According to the present embodiment, in addition to the effects described in the second embodiment, since the perfect circle of the part provided with the mesh ring 820 is maintained, smoothing of the rotation of the probe tip portion can be performed and, therefore, a proper OCT image can be produced.

Figure 50:
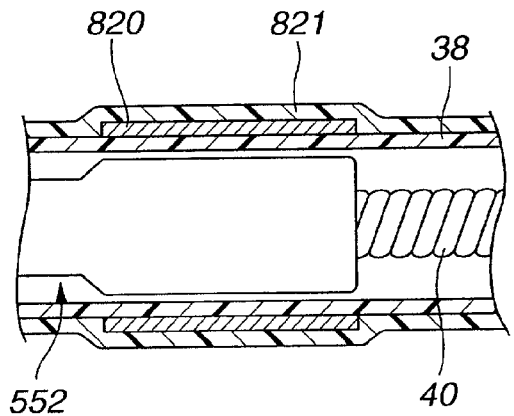

As shown in FIG. 50, the mesh ring 820 may be provided by getting caught in somewhat thin tube 821, and in this case, the mesh ring 820 can be prevented from directly contacting with a living body.

Figure 51:
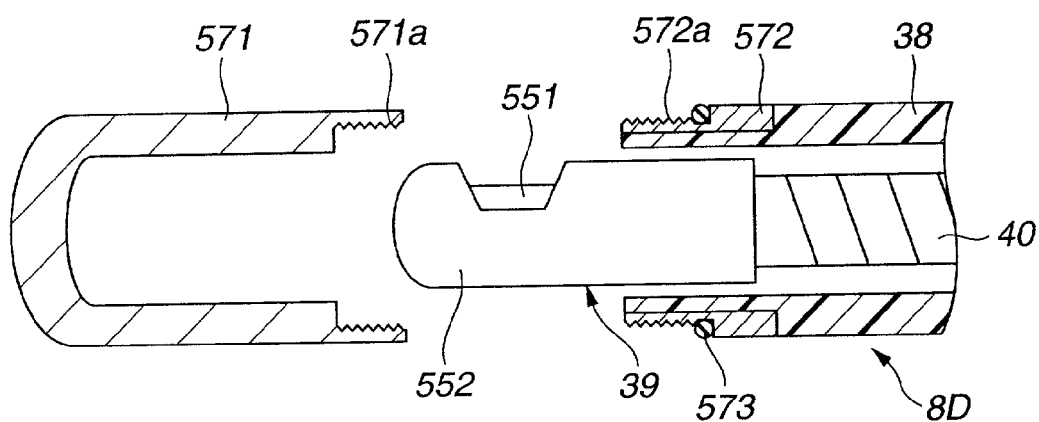
FIG. 51 and FIG. 52 relate to a tenth embodiment according to the present invention.

Tenth Embodiment:

The tenth embodiment according to the present invention will be described below with reference to FIG. 51. FIG. 51 shows the configuration of the tip side of an optical probe device 8D according to the tenth embodiment of the present invention.

As shown in FIG. 51, the neighborhood of the tip of the sheath 38 includes a housing 552 of a tip unit 39 in which a prism 551 is fixed in the inside, a flexible shaft 40, the tip of which is connected to the base end of the housing 552 and which transfers rotation from the base end portion thereof, a tip cap 571 which covers the housing 552 and which is formed from a raw material having excellent light transparency, and a flexible sheath 38 provided with a joint ring 572, to which the rear end of the tip cap 571 is connected while being free to attach or detach, at the tip.

A thread portion 572a is provided on the joint ring 572 fitted to the tip of the sheath 38 with adhesive, etc., and is thread-engaged with a thread portion 571a provided on the rear end of the cap 571 and, therefore, the cap 571 can be fitted while being free to attach or detach.

The prism 551 is positioned in order that the light exit•entrance can be performed through the side surface of the cap 571 under the condition in which the cap 571 is fitted to the sheath 38. Furthermore, in the configuration, an O-ring 573 is interposed at the height difference portion of the joint ring 572, and under the condition in which the cap 571 is fitted to the tip of the sheath 38, the O-ring 573 is pressed by the rear end of the cap 571 and, therefore, the inside can be kept watertight.

Other configuration is similar to that in, for example, the second embodiment.

According to such a configuration, when the cap outer surface is damaged by, for example, insertion of the endoscope into the channel for forceps, or the housing 552 is contacted with the cap 571 inner surface, the cap 571 inner surface is damaged by friction due to rotation and, therefore, optical characteristics are degraded, the cap can be removed by rotating, a new one can be fitted by rotating in the reverse direction and, therefore, predetermined optical characteristics can be maintained.

The present embodiment has the following effects.

Since the optical characteristics can be maintained only by exchanging the cap 571 without the need for exchanging the whole sheath, outlay of the user can be reduced.

Regarding the selection of the sheath raw material, a raw material suitable for the usage conditions can be used not depending on the optical performances. Other effects are similar to those in the fourth embodiment.

Figure 52:
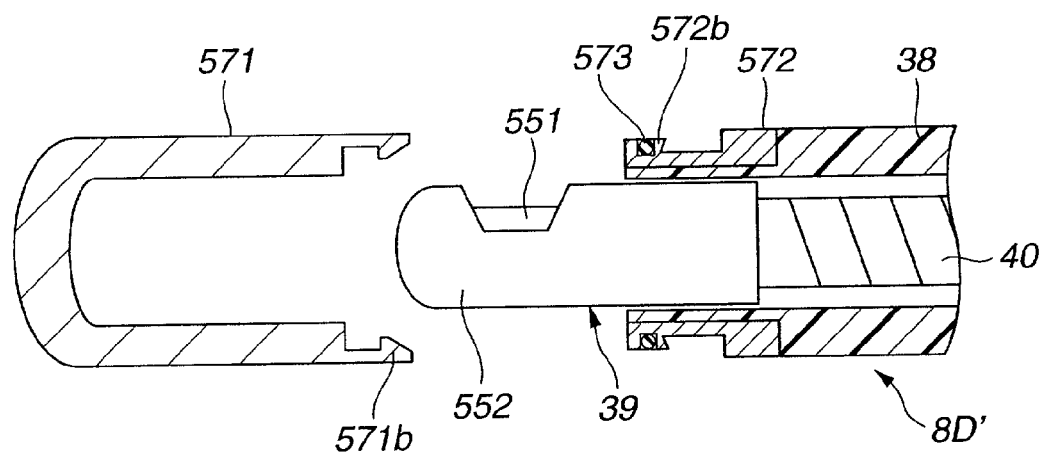

FIG. 52 shows the configuration of the tip side of an optical probe device 8D' of a modified example. In this modified example, an attachment and detachment mechanism due to a click mechanism is adopted instead of the attachment and detachment mechanism due to thread engagement in FIG. 51.

For example, on a joint ring 572 fitted to the tip of the sheath 38, a convex portion 572b is provided while the front end thereof is protruded toward the outside in the radius direction, and a concave portion is formed at the part adjacent thereto. On the other hand, regarding the cap 571, a convex portion 571b which is fitted into the aforementioned concave portion is provided at the rear end thereof, and at the part adjacent thereto, an concave portion, to which the aforementioned convex portion 572b is fitted, is provided. This cap 571 has light transparency, and (at least) the rear end side thereof is formed from a resin, etc., which can be elastically deformed in moderation.

For example, the diameter of the rear end of the cap is enlarged to have the shape of a taper in order to fit into the joint ring 572 with ease. An O-ring 573 for watertightness is interposed in the convex portion 572b.

In the present modified example, by performing the operation of putting the rear end side of the cap 571 into the joint ring 572 side, the convex portion 571b at the rear end of the cap 571 hits the convex portion 572b of the joint ring 572, deforms, gets over, fits into the concave portion adjacent to the convex portion 572b and, therefore, fitting can be conducted.

When this cap 571 is exchanged, the cap 571 can be removed by pulling toward the tip side in a manner opposite to that in the case of fitting.

In the present modified example, attachment and detachment of the cap 571 is easier than that in the tenth embodiment. The rotary scan system of the probe may be changed to a sector scan in which sector-shaped reciprocating motion is performed. In the case where such a scan is performed, when the direction of attachment and detachment of the cap 571 is specified, only the part facing the light exit•entrance surface of the prism 551 is configured from a member having excellent light transparency, and other parts need not take this into consideration and, therefore, the flexibility in selection of material and configuration of the cap 571 is increased. Other effects are similar to those in the tenth embodiment.

Figure 53:
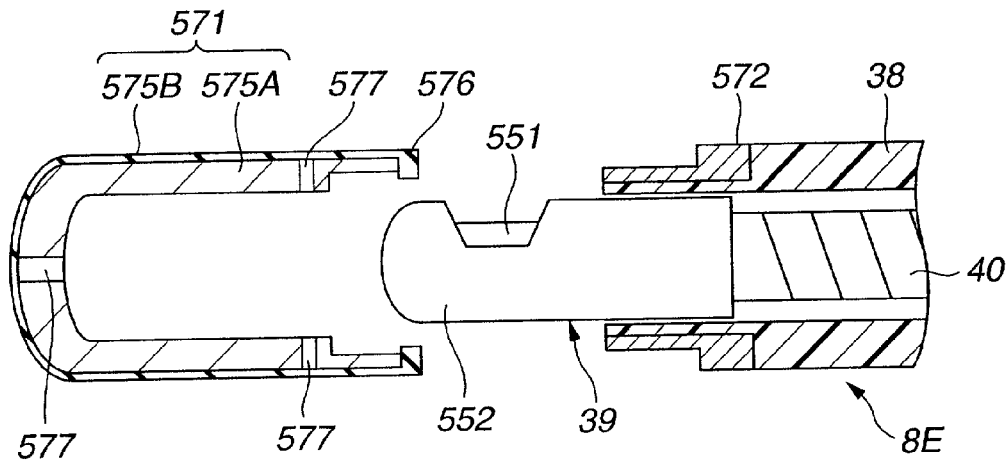
FIG. 53 is a diagram showing the configuration of the tip side of an optical probe device of an eleventh embodiment according to the present invention.

Eleventh Embodiment:

The eleventh embodiment according to the present invention will be described below with reference to FIG. 53. FIG. 53 shows the configuration of the tip side of an optical probe device 8E according to the eleventh embodiment of the present invention.

The tip side of this optical probe device 8E is similar to that in FIG. 52.

As shown in FIG. 53, a joint ring 572 is provided at the tip of the sheath 38, and a cap 571 formed from a cap main body 575A and a balloon 575B is fitted to this joint ring 572 while being free to attach or detach.

The balloon 575B to become a pliable film portion, in which the outer surface of the cap main body 575A and an annular ring-shaped fixing portion 576 covering the rear end thereof are integrally formed, is provided on the cap main body 575A, and a communication path 577 communicating the cap inner surface and the pliable film inner surface is provided at the part other than the position facing the prism 551 of the cap main body 575A.

The inner diameter of the fixing portion 576 is smaller than the outer diameter of the tip side of the joint ring 572. During fitting, this fixing portion 576 is pushed and deformed to enlarge the diameter and is arranged at the position in contact with the height difference portion of the joint ring 572 and, therefore, can be fixed watertight due to frictional force thereof. By applying a force that pulls the cap 571 toward the tip side against this frictional force, removal can be performed.

Other configuration is nearly similar to that shown in FIG. 52.

According to such a configuration, actions similar to those in the tenth embodiment can be achieved and, in addition, when the inside of the cap 571 and the sheath 38 is filled with a refractive index matching medium, for example, water, in advance, and if necessary, the refractive index matching medium is supplied from the rear end side on the side at hand, it flows into the balloon 575B side through the communication path 577 of the cap main body 575A and, therefore, the pliable film portion of the balloon 575B can be evaginated.

The present embodiment has the following effects.

Other than the effects similar to those in the tenth embodiment, the balloon 575B can be formed with ease only by fitting the cap 571, refractive indices between the prism 551 and the cap 571 and between the cap 571 and the sample are matched by the refractive index matching medium. Therefore, undesirable effects of reflection can be reduced, and the image quality of the OCT image can be improved.

Figure 54A:
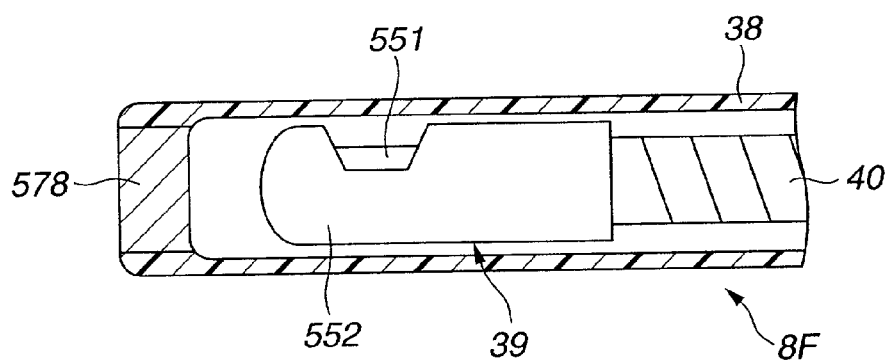
FIG. 54A and FIG. 54B relate to a twelfth embodiment according to the present invention.
Figure 54B:
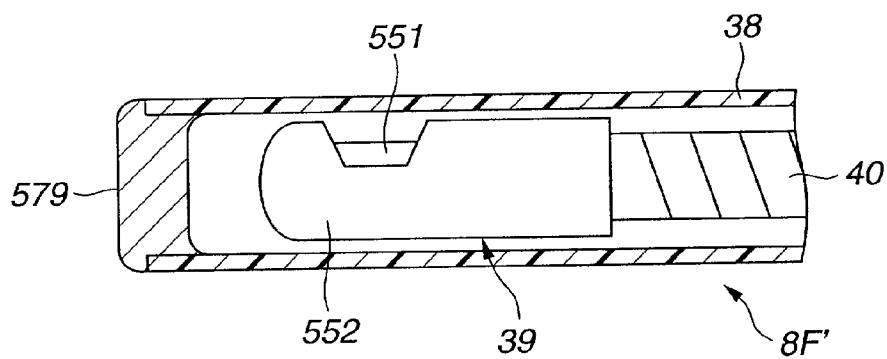

Twelfth Embodiment:

The twelfth embodiment according to the present invention will be described below with reference to FIG. 54A and FIG. 54B. FIG. 54A and FIG. 54B show the configuration of the tip side of an optical probe 8F according to the twelfth embodiment of the present invention.

As shown in FIG. 54A, the neighborhood of the probe tip is composed of a housing 552, to which a prism 551 is fixed, a flexible shaft 40 connected to the housing 552, a transparent sheath 38, which is made of a resin and which covers it, and a metal piece 578 which is fixed to the tip of the sheath 38 and which has a radiopacity function. The rear end side of this sheath has a configuration similar to that in the second embodiment.

According to such a configuration, when the optical probe device 8F is inserted into narrow lumen organs, for example, bile•pancreatic ducts, blood vessels, and bronchi, under radioscopy, the metal piece 578 at the tip becomes an X-ray photography portion and, therefore, the tip portion can be detected with ease.

In the configuration, the tip portion may be sealed with a metal cap 579 as an optical probe device 8F' shown in FIG. 54B.

The metal piece at the tip or the metal cap may be composed of a material unlikely to transmit X-ray, for example, a resin containing a metal powder, other than a metal.

The present embodiment has the following effects.

It is possible that the tip portion can be detected with reliability under radioscopy and, therefore, operating ease can be improved. Other effects are similar to those in the second embodiment.

Figure 55:
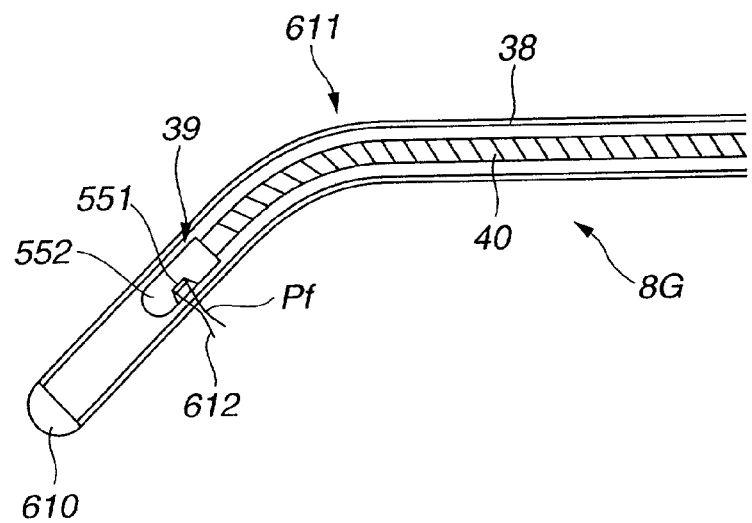
FIG. 55 to FIG. 57 relate to a thirteenth embodiment according to the present invention.
Figure 56:
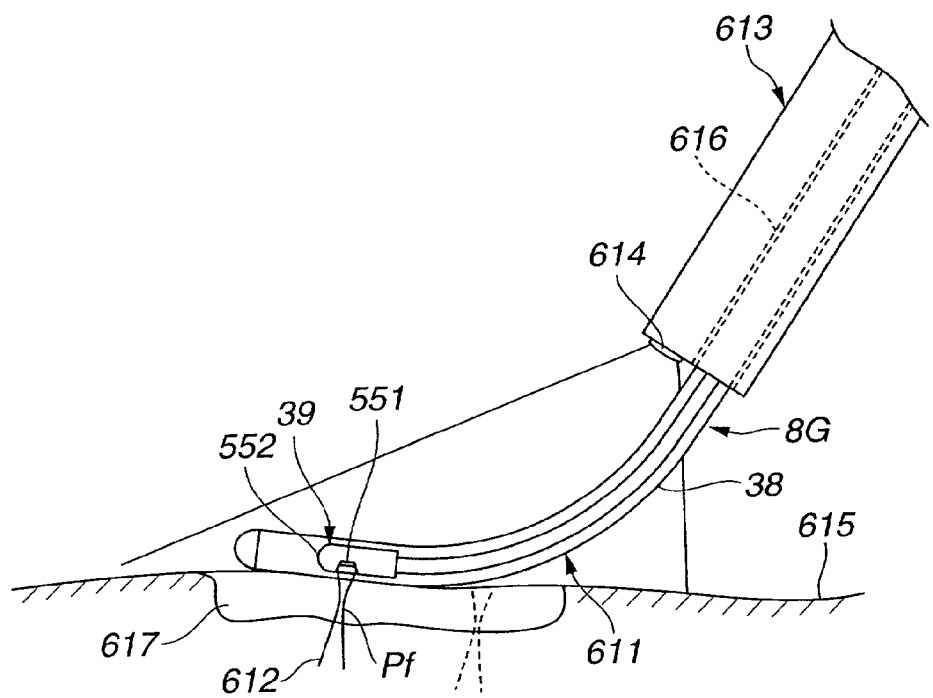

Thirteenth Embodiment:

The thirteenth embodiment according to the present invention will be described below with reference to FIG. 55 and FIG. 56. FIG. 55 shows the configuration of the tip side of an optical probe 8G according to the thirteenth embodiment of the present invention, and FIG. 56 shows an example of use.

As shown in FIG. 55, the optical probe 8G includes a sheath 38 which is made of a resin and in which the tip portion is blocked with a tip cap 610 and at least the tip portion is transparent, a housing 552 for holding a tip unit 39, for example, a prism 551, provided in a lumen on the tip side of this sheath 38, and a flexible shaft 40 joined to the root portion of this housing 552.

In the present embodiment, a curved portion 611 which has property of curving in the predetermined direction is provided on the side nearer to the rear end than is the part containing the housing 552 while keeping some distance in the sheath 38. This curved portion 611 can be made linear with ease by an external force.

The focus position Pf of an observation beam 612 made to exit from the prism 551 is designed to be outside the sheath 38 and in the neighborhood of the outer perimeter surface thereof. For example, the focus position Pf is adjusted at on the order of 0.5 to 1 mm from the outer perimeter surface of the sheath.

According to such a configuration shown in FIG. 55, since the focus position is set in the neighborhood of the sheath, the focus position can be adjusted at the observation part by contacting the sheath 38 with the specimen.

For example, as shown in FIG. 56, when observation is performed by insertion of the sheath portion (probe portion) of the optical probe 8G through a channel 616 from a forceps insertion hole, although not shown in the drawing, while a specimen 615 is ascertained with an endoscope 613 under the illumination of the tip portion thereof and an observational optical system 614, by the curved portion 611 provided in the sheath 38, an OCT image can be produced with ease by exit of the observation beam 612, while the part on the side nearer to the tip than is the curved portion 611 is contacted with the surface tissue and, therefore, the focus position pf is set at a lesion portion 617, etc., without pressing the probe against the surface tissue of the specimen 615.

The present embodiment has the following effects.

Positioning of the light exit•entrance portion on the tip side of the optical probe 8G relative to the specimen can be performed with reliability and ease and, therefore, stability of image quality and operating ease are improved.

Since observation can be performed while the tip side of the optical probe 8G is in contact with the specimen without being pressed against the specimen, information of the specimen can be gained more precisely or faithfully (with no pressure deformation) than that in the conventional manner.

Since it is possible to observe while the tip side of the optical probe 8G is in contact with the specimen without being pressed against the specimen, it is possible to use for a fragile tissue•lesion portion.

Figure 57:
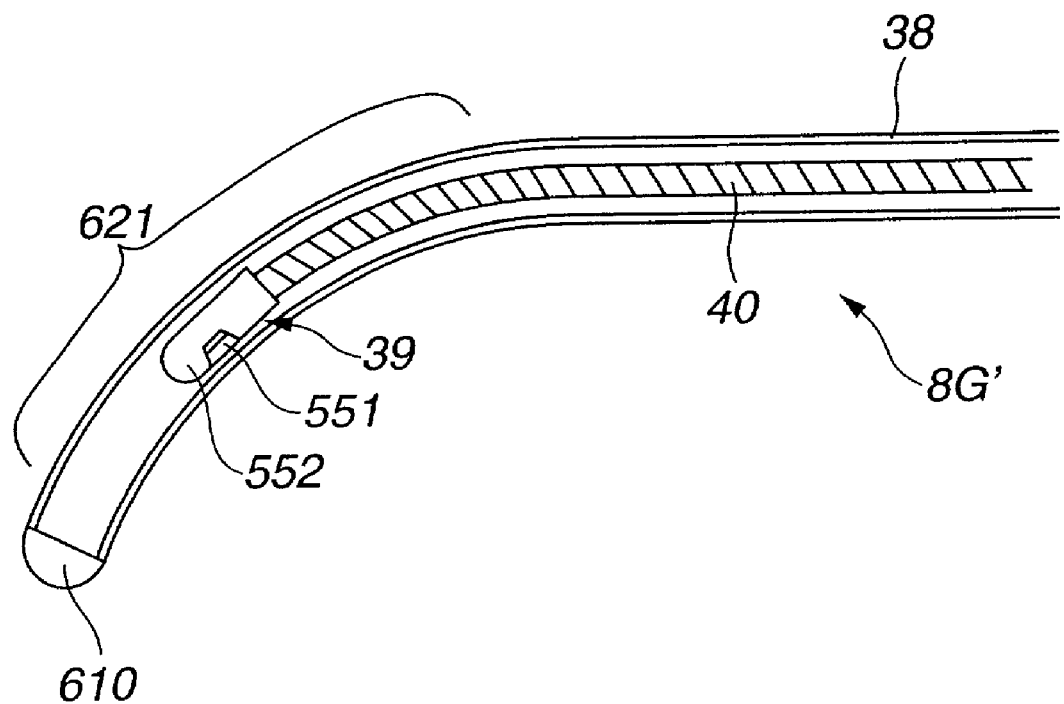

FIG. 57 shows the tip side of an optical probe 8G' of a modified example. In this optical probe 8G', a curved portion 621 due to property of curving of the sheath 38 is provided on the side nearer to the tip than is in the case shown in FIG. 55, that is, in order that the part containing the housing 552 is included, for example, the part from the sheath tip portion toward the rear side is curved over an appropriate distance range.

Other configuration is similar to that shown in FIG. 55.

According to the configuration shown in FIG. 57, when this optical probe 8G' is used by being inserted through the channel 616 of the endoscope 613 shown in FIG. 56, the amount of bending of the sheath tip side can be adjusted by changing the protrusion length of the sheath protruded from the tip of the channel 616.

Therefore, by changing the sheath protrusion length in accordance with the angle between the axis direction of the tip side of the endoscope 613 and the surface of the observation target part of the specimen, observation can be performed while the sheath portion outside the prism 551 is in contact with the surface of the observation target part.

Regarding the present embodiment, in addition to the effects similar to those in the thirteenth embodiment, positioning of the probe relative to the specimen can be set in the wide range and, therefore, operating ease is improved.

Figure 58:
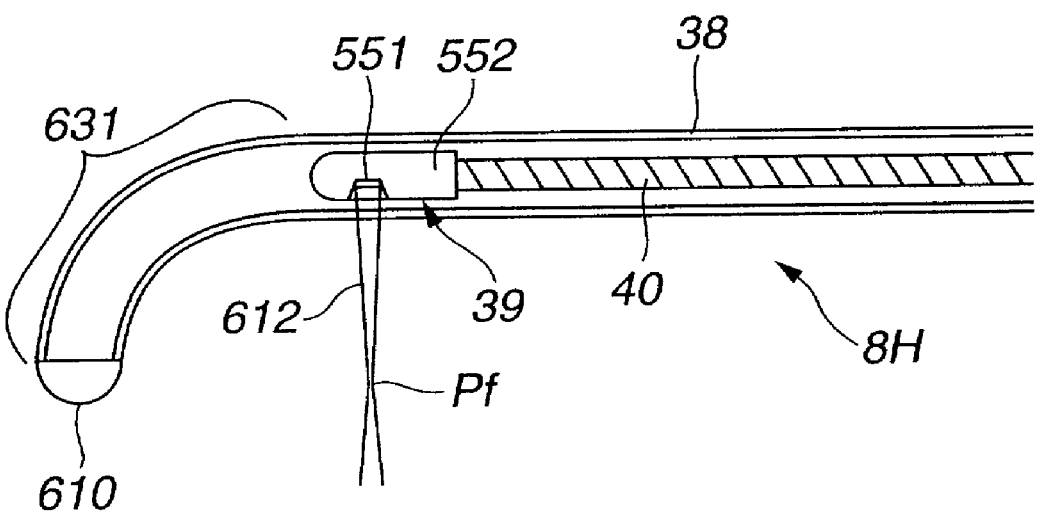
FIG. 58 to FIG. 60 relate to a fourteenth embodiment according to the present invention.
Figure 59:
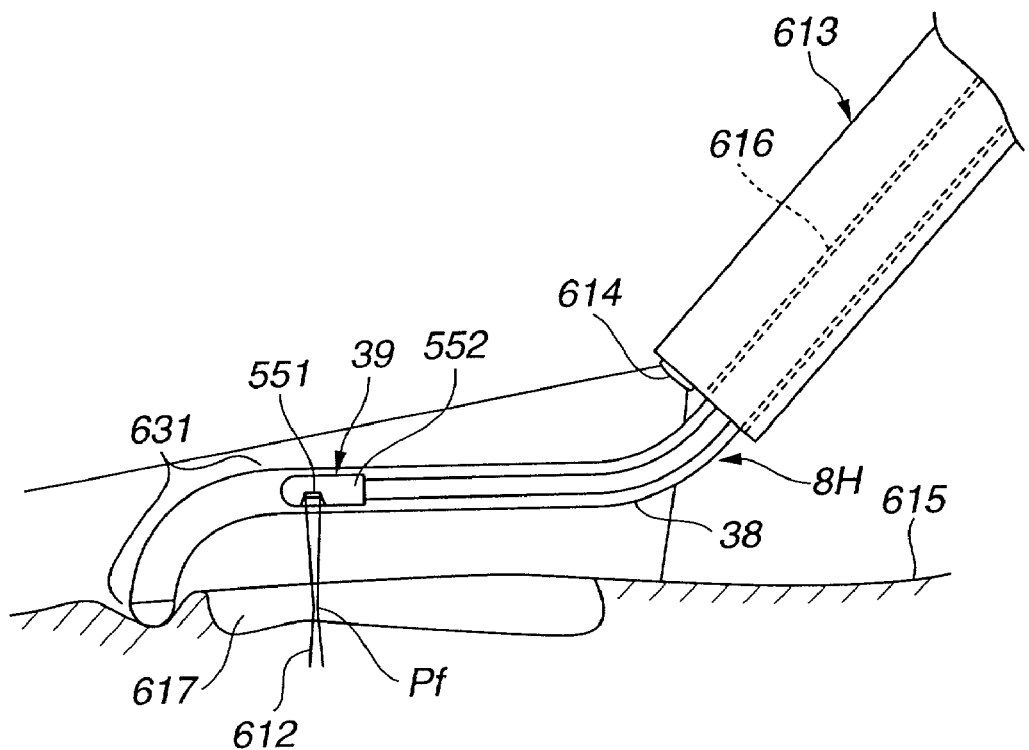

Fourteenth Embodiment:

The fourteenth embodiment according to the present invention will be described below with reference to FIG. 58 and FIG. 59. FIG. 58 shows the configuration of the tip side of an optical probe 8H according to the fourteenth embodiment of the present invention, and FIG. 59 shows an example of use.

Although in FIG. 55, the curved portion 611 has been provided on the side rearward of the position at which the housing 552 has been contained, in the optical probe 8H shown in FIG. 58, a curved portion 631 is provided while having a curved shape from the tip of the sheath 38 to the neighborhood of the position immediately in front of the position at which the housing 552 is contained.

The focus position Pf of the observation beam 612 is designed to be somewhat far from the outer perimeter surface of the sheath. The focus position Pf is adjusted at 1.5 to 3.0 mm from the outer perimeter surface of the sheath. The configuration is similar to that in the thirteenth embodiment except the aforementioned points.

According to such a configuration, it is better to observe while some distance is put between the specimen and the outer perimeter surface of the probe in order that the focus position Pf of the observation beam 612 can be adjusted at the specimen.

For example, as shown in FIG. 59, when observation is performed while the tip cap 610 of the sheath tip is pressed against the part adjacent to the observation target part (for example, a lesion portion 617) in the specimen 615, it is possible to produce an OCT image while the focus position Pf of the observation beam 612 is easily set to be kept constant at the observation target part in the specimen 615. The observation can be performed without pressing the optical probe 8H against the observation target part in the specimen 615.

Figure 60:
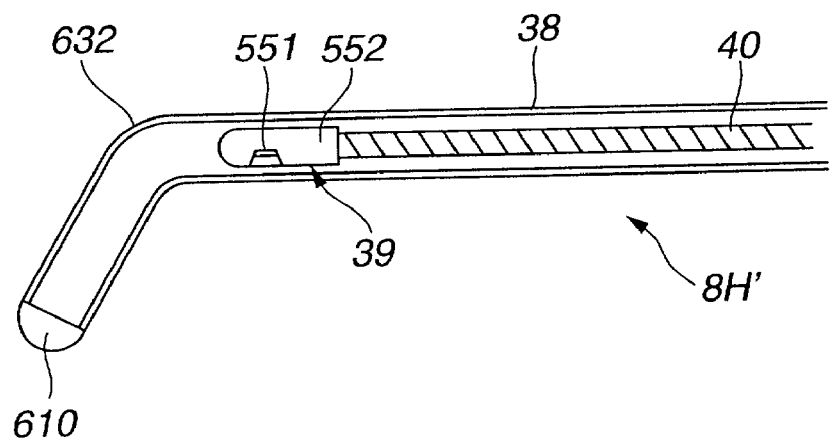

In FIG. 58, the curved portion 631 has been formed by bending the sheath 38 into the shape of an arc. However, not limited to this, as shown in FIG. 60, a curved portion 632 may be formed by folding at the position on the side nearer to the tip than is the tip of the housing 552.

The present embodiment has the following effects.

Since the focus position of the observation beam relative to the specimen can be kept constant with ease, stability of the image quality and operating ease are improved.

Since it is possible to set that the tip side of the optical probe 8H does not contact with the observation part in the specimen, precise information of the specimen can be gained.

Fifteenth Embodiment:

The fifteenth embodiment according to the present invention will be described below with reference to FIG. 61.

An optical probe 8I shown in FIG. 61 adopts a sheath using a multi-lumen tube 643 having two holes 641 and 642, large and small. The main body portion of the optical probe is inserted into the large hole 641, and a connector potion 9 at the rear end thereof is connected to an observation device, although not shown in the drawing, while being free to attach or detach.

A flexible wire 644, which is made of a metal and in which the tip portion is imparted with property of curving, is inserted into the small hole 642.

The rear end side of this wire 644 is extended from a divarication portion 645 to the outside. When the degree of insertion of the wire 644 is adjusted using a ring 646 at the rear end of the wire 644, a curving mechanism which curves the sheath tip portion, as indicated by alternate long and short dashed lines or a chain double-dashed line, from a linear condition can be imparted.

Likewise, when a curved portion due to property of curving is provided at the sheath tip portion, and a wire made of a metal is used without provision of property of curving at the tip, the curving mechanism can be imparted.

The present embodiment has the following effects.

In the case where, for example, insertion is performed into blood vessels and other small diameter tracts having many curves and divarications, by operating the rear end side of the wire 644, a curving angle, etc., at the tip side of the optical probe 8I can be adjusted and, therefore, insertion into a desired small diameter tract can be performed with ease by this curving mechanism. That is, operating ease is improved.

By imparting the curving mechanism, the actions•effects of the thirteenth embodiment or fourteenth embodiment can be exhibited only when the operator judges them necessary during observation and, therefore, operating ease of the probe is further improved.

FIG. 62 shows an optical probe 8I' of a modified example. In this optical probe 8I', the tip of the wire 644 inserted into the small hole 642 is fixed to the sheath tip portion 651. A soft raw material likely to be elastically deformed is used for the tip side of the multi-lumen tube 643 and, therefore, a soft portion 652 is formed. A hard raw material relatively unlikely to be elastically deformed is used for the side rearward of this soft portion 652 and, therefore, a hard portion 653 is formed.

By pulling the ring 646, the neighborhood of the small hole 642 of the soft portion 653 is contracted in the longitudinal direction and, therefore, the soft portion 652 can be curved in order that the side, at which the small hole 642 has been formed, is made to be the inner side.

Effects of this modified example have effects nearly similar to those in the fourteenth embodiment.

Sixteenth Embodiment:

Only the part different from that in the first embodiment will be described with reference to FIG. 63 to FIG. 64.

In the present embodiment, as shown in FIG. 63, at the tip of the optical probe 8A, a pointed portion 201 is provided at the tip of the housing 552, a dent portion 202 is provided at the inner surface of a seal member 38c, the pointed portion 201 and the dent portion 202 are made to contact with each other by point contact, friction due to rotation is prevented and, furthermore, the rear end surface of the housing 552 is in contact with the locking member 38d.

As shown in FIG. 64, at the rear end of the optical probe 8A, a shaft stopping member 203, to which the rear end of the flexible shaft 40 is connected, is provided, pins 204 provided on the outer perimeter surface of the shaft stopping member 203 are fitted into rectangular holes 205 formed in the rotation transfer connector 42 while being able to slide and, therefore, rotation is transferred to the flexible shaft 40, and movement distance of the shaft stopping member 203 in the longitudinal axis direction is regulated.

In the present embodiment thus configured, by the rectangular holes 205 and the pins 204, the rotation is transferred to the flexible shaft 40, and the movement distance of the shaft stopping member 203 is regulated. Even when the optical probe 8A is curved during use of the optical probe 8A, positional relationship between the optical sheath 38 and the flexible shaft 40 is changed and, therefore, a force which moves tip housing 552 is applied, since movement of the tip housing 552 is fixed by contact of the pointed portion 201 and the dent portion 202 at the tip side and by contact of the rear end surface of the tip housing 552 and the locking member 38d at the rear end side, the amount of movement thereof is absorbed by sliding of the shaft stopping member 203 on the side at hand.

The interval between the valley of the dent portion 202 and the locking member 38d may be set slightly larger than the interval between the pointed portion 201 and the rear end surface of the tip housing 552 within the range of assembly error, etc. The tip housing 552 may be contacted at one of between the pointed portion 201 and the dent portion 202 and between the rear end surface of the tip housing 552 and the locking member 38d.

Consequently, in the present embodiment, the tip housing 552 is rotated at the same position relative to the probe longitudinal direction on all occasions. Since it is not necessary to apply tension to the flexible shaft 40 in advance in contrast to the first embodiment, assembly is simplified and productivity is improved.

In the present embodiment as well, as shown in FIG. 7, the tip bearings 151 made of a rigid resin, for example, Derlin and polycarbonate, may be interposed between the rear end surface of the tip housing 552 and the locking member 38d.

Seventeenth Embodiment:

Only the part different from that in the first embodiment will be described with reference to FIG. 65 and FIG. 66.

In the present embodiment, as shown in FIG. 65, a biopsy unit 300 is provided on the tip sheath 38a, and a tube 301 is extended from the biopsy unit 300 along the optical sheath 38 and, therefore, an optical probe 8A is configured.

Regarding the biopsy unit 300, an opening portion 302 is provided at the light radiation position from housing 552, and inside the biopsy unit 300 of the opening portion 302, a slide edge 304 is provided while being regulated by an edge guide 305 and being able to slide in the longitudinal axis direction by a wire 306.

The wire 306 is inserted through the tube 301, and is extended from a biopsy operation portion 307 provided at the base end of the tube 301 to the outside through an O-ring 308 with watertightness while being able to slide. On the biopsy operation portion 307, a connection hole 309 is provided in order to connect to a suction device and a syringe described below.

In the present embodiment thus configured, as shown in FIG. 66, the suction device 310 is connected to the connection hole 309. When a lesion is found out with the optical probe 8A, the tissue is suctioned through the opening portion 303 by the use of the suction device 310, resection is performed with the slide edge 304 by the operation of the wire 306, and the tissue is stored in the biopsy unit 300. Subsequently, the optical probe 8A is taken out of the body cavity, the syringe, although not shown in the drawing, is connected to the connection hole 309, a physiological salt solution, etc., is feed and, therefore, the tissue stored is taken out through the opening portion 303 and biopsy is performed.

As described above, regarding the present embodiment, in addition to the effects in the first embodiment, since biopsy can be performed at the same time with observation, operating ease and diagnostic performance are improved.

It is needless to say that the present embodiment can be applied to the optical probe 8A according to the sixteenth embodiment.

The aforementioned embodiments may be performed in combination with each other. For example, when the probe tip configurations according to the second embodiment to the sixth embodiment are combined with the sixteenth embodiment, similar friction reduction effect of the probe tip can be achieved. By combining the fifth and sixth embodiments with the second embodiment to the fourth embodiment, it becomes easier to make the tip clearance of the probe always zero and, therefore, the rotation position of the tip housing is further stabilized.

When the configuration of the seventeenth embodiment is applied to all embodiments, it becomes possible to perform biopsy with ease at the same time with observation of the living body.

When the tip sheath 38a of the first, sixteenth, and seventeenth embodiments have the configuration, in which attachment and detachment can be performed freely, as in the tenth embodiment, in the case where the outer perimeter surface of the tip sheath 38a is damaged, it is possible to exchange for a new one with ease and, therefore, labor hour•cost for repair of the probe can be omitted.

Regarding the second embodiment, the configuration may only include elements shown in FIG. 13, or only include elements shown in FIG. 9 to FIG. 12 and FIG. 14.

Regarding the third embodiment, the configuration may only include elements shown in FIG. 15, or only include elements shown in FIG. 16 to FIG. 19.

Regarding the fourth embodiment, the configuration may only include elements shown in FIG. 20A and FIG. 20B, or only include elements shown in FIG. 21.

In the present invention, it is clear that different embodiments can be configured in wide range based on the present invention without departing from the spirit or scope of the invention. The present invention is not limited to specified embodiments thereof other than those defined in the appended claims.

The invention claimed is:

1. An optical probe comprising:
a sheath in which at least a tip side is transparent and flexible, and a tip thereof is blocked;
a light exit•entrance portion provided in a lumen in the neighborhood of the sheath tip;
a housing for holding the light exit•entrance portion;
a flexible shaft which is connected to a rear end of the housing and which transfers torque; and
a base end portion to which a rear end side of the flexible shaft and a rear end side of the sheath are connected, wherein the base end portion comprises a pipe which slidably engages the sheath;
a watertight mechanism provided on an inner perimeter surface near a tip of the pipe; and
a relative distance adjustment mechanism capable of adjusting the relative distance between the housing and the sheath tip which is provided on the side nearer to the base end of the pipe than the watertight mechanism.

2. The optical probe according to claim 1,
wherein the relative distance adjustment mechanism comprises a sheath length adjustment mechanism capable of adjusting the protrusion length of the sheath from the base end portion.

3. The optical probe according to claim 2,
wherein the sheath length adjustment mechanism comprises a sheath attachment and detachment mechanism in which the sheath is free to attach to or detach from the base end portion.

4. The optical probe according to claim 2,
comprising a housing position keeping mechanism for keeping the housing at a predetermined position on the sheath tip.

5. The optical probe according to claim 4,
wherein the housing position keeping mechanism is a friction prevention mechanism which is provided between the sheath tip inner surface and the housing tip and which prevents friction during rotation of the housing.

6. The optical probe according to claim 5,
wherein the sheath tip inner surface and the housing tip are in contact with each other with the friction prevention mechanism therebetween.

7. The optical probe according to claim 4,
wherein the housing position keeping mechanism comprises a locking portion which is formed in the sheath lumen and which is provided facing the base end surface of the housing.

8. The optical probe according to claim 7,
wherein the base end surface of the housing and the locking portion are in contact with each other.

9. The optical probe according to claim 7,
wherein a friction prevention mechanism is provided between the base end surface of the housing and the locking portion.

10. The optical probe according to claim 1,
wherein the relative distance adjustment mechanism comprises a flexible shaft length adjustment mechanism capable of adjusting the protrusion length of the flexible shaft from the base end portion.

11. The optical probe according to claim 10,
wherein the flexible shaft length adjustment mechanism comprises a shaft connection portion which connects the flexible shaft to the base end portion, and a shaft connection distance keeping mechanism which can adjust the connection length of the shaft connection portion with respect to the base end portion and which can fix at a desired position.

12. The optical probe according to claim 11,
comprising a housing position keeping mechanism for keeping the housing at a predetermined position on the sheath tip.

13. The optical probe according to claim 12,
wherein the housing position keeping mechanism is a friction prevention mechanism which is provided between the sheath tip inner surface and the housing tip and which prevents friction during rotation of the housing.

14. The optical probe according to claim 13,
wherein the sheath tip inner surface and the housing tip are in contact with each other with the friction prevention mechanism therebetween.

15. The optical probe according to claim 12,
wherein the housing position keeping mechanism comprises a locking portion which is formed in the sheath lumen and which is provided facing the base end surface of the housing.

16. The optical probe according to claim 15,
wherein the base end surface of the housing and the locking portion are in contact with each other.

17. The optical probe according to claim 15,
wherein a friction prevention mechanism is provided between the base end surface of the housing and the locking portion.

18. The optical probe according to claim 10,
wherein the flexible shaft length adjustment mechanism comprises a shaft connection portion which connects the flexible shaft to the base end portion, and a shaft connection portion sliding mechanism which is free to slide the shaft connection portion in the longitudinal direction and which transfers rotation from a driving unit provided in the base end portion to the shaft connection portion.

19. The optical probe according to claim 18,
comprising a housing position keeping mechanism for keeping the housing at a predetermined position on the sheath tip.

20. The optical probe according to claim 19,
wherein the housing position keeping mechanism comprises a friction prevention mechanism which is provided between the sheath tip inner surface and the housing tip and which prevents friction during rotation of the housing, and a locking portion which is formed in the sheath lumen and which is provided facing the base end surface of the housing.

21. The optical probe according to claim 20,
wherein the sheath tip inner surface and the housing tip are in contact with each other with the friction prevention unit therebetween, and the base end surface of the housing and the locking portion are in contact with each other.

22. The optical probe according to claim 20,
wherein the sheath tip inner surface and the housing tip are in contact with each other with the friction prevention mechanism therebetween, or the base end surface of the housing and the locking portion are in contact with each other.

23. The optical probe according to claim 20,
wherein the friction prevention mechanism is provided between the base end surface of the housing and the locking portion.

24. The optical probe according to claim 1,
comprising a housing position keeping mechanism for keeping the housing at a predetermined position on the sheath tip.

25. The optical probe according to claim 24,
wherein the housing position keeping mechanism comprises a contact portion provided on the housing, and the locking portion provided on the sheath.

26. The optical probe according to claim 25,
wherein the friction prevention mechanism is provided between the contact portion and the locking portion.

27. The optical probe according to claim 26,
wherein the friction prevention mechanism is based on point contact between the contact portion and the locking portion.

28. The optical probe according to claim 26,
wherein the friction prevention mechanism is a bearing provided between the contact portion and the locking portion.

29. The optical probe according to claim 25,
wherein the contact portion and the locking portion are in contact with each other.

30. The optical probe according to claim 29,
wherein the relative distance adjustment mechanism comprises a shaft connection portion which connects the flexible shaft to the base end portion, and a shaft connection portion sliding mechanism which is free to slide the shaft connection portion in the longitudinal direction and which transfers rotation from a driving mechanism provided in the base end portion to the shaft connection portion.

31. The optical probe according to claim 30,
wherein the contact portion is provided at each of the housing tip and the base end surface, and the locking portions are provided at the sheath tip inner surface and at the position facing the base end surface of the housing.

32. The optical probe according to claim 30,
wherein the contact portion is provided at the tip of the housing, and the locking portion is provided at the sheath tip inner surface.

33. The optical probe according to claim 30,
wherein the contact portion is provided at the housing base end surface, and the locking portion is provided at the position facing the base end surface of the housing.

34. The optical probe according to claim 29,
wherein the contact between the contact portion and the locking portion is pressure contact.

35. The optical probe according to claim 34,
wherein an energizing mechanism is provided for pressure contact of the contact portion and the locking portion.

36. The optical probe according to claim 35,
wherein the energizing mechanism comprises a combination of the flexible shaft and the relative distance adjustment mechanism.

37. The optical probe according to claim 36,
wherein the contact portion is provided at the housing tip, the locking portion is provided at the sheath tip inner surface, the contact portion and the locking portion are pressure-contacted by compression energization of the flexible shaft with the relative distance adjustment mechanism.

38. The optical probe according to claim 37,
wherein the relative distance adjustment mechanism comprises a sheath length adjustment mechanism capable of adjusting the protrusion length of the sheath from the base end portion.

39. The optical probe according to claim 38,
wherein the sheath length adjustment mechanism comprises a sheath attachment and detachment mechanism in which the sheath is free to attach to or detach from the base end portion.

40. The optical probe according to claim 37,
wherein the relative distance adjustment mechanism comprises a flexible shaft length adjustment mechanism capable of adjusting the protrusion length of the flexible shaft from the base end portion.

41. The optical probe according to claim 37,
wherein the relative distance adjustment mechanism comprises a sheath length adjustment mechanism capable of adjusting the protrusion length of the sheath from the base end portion, and a flexible shaft length adjustment mechanism capable of adjusting the protrusion length of the flexible shaft from the base end portion.

42. The optical probe according to claim 41,
wherein the sheath length adjustment mechanism comprises a sheath attachment and detachment mechanism in which the sheath is free to attach to or detach from the base end portion.

43. The optical probe according to claim 36,
wherein the contact portion is provided at the base end surface of the housing, and the locking portion is provided at the position facing the base end surface of the housing, and the contact portion and the locking portion are pressure-contacted by tension energization of the flexible shaft with the relative distance adjustment mechanism.

44. The optical probe according to claim 43,
wherein the relative distance adjustment mechanism comprises a sheath length adjustment mechanism capable of adjusting the protrusion length of the sheath from the base end portion.

45. The optical probe according to claim 44,
wherein the sheath length adjustment mechanism comprises a sheath attachment and detachment mechanism in which the sheath is free to attach to or detach from the base end portion.

46. The optical probe according to claim 43,
wherein the relative distance adjustment mechanism comprises a flexible shaft length adjustment mechanism capable of adjusting the protrusion length of the flexible shaft from the base end portion.

47. The optical probe according to claim 43,
wherein the relative distance adjustment mechanism comprises a sheath length adjustment mechanism capable of adjusting the protrusion length of the sheath from the base end portion, and a flexible shaft length adjustment mechanism capable of adjusting the protrusion length of the flexible shaft from the base end portion.

48. The optical probe according to claim 47,
wherein the sheath length adjustment mechanism comprises a sheath attachment and detachment mechanism in which the sheath is free to attach to or detach from the base end portion.

49. The optical probe according to claim 35,
wherein the energizing mechanism is an elastic member provided at the sheath tip inner surface.

50. The optical probe according to claim 49,
wherein the elastic member is a coil spring.

51. The optical probe according to claim 1,
comprising a resection mechanism capable of resecting living-body tissue in the neighborhood of the position where the low-coherence light exiting from the light exit•entrance portion enters.

* * * * *